US012678514B2

(12) United States Patent
Wang et al.

(10) Patent No.: US 12,678,514 B2
(45) Date of Patent: Jul. 14, 2026

(54) ALGAE-BASED MICROROBOT FOR DRUG DELIVERY

(71) Applicant: The Regents of the University of California, Oakland, CA (US)

(72) Inventors: Joseph Wang, La Jolla, CA (US); Liangfang Zhang, La Jolla, CA (US); Fangyu Zhang, La Jolla, CA (US); Jia Zhuang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 279 days.

(21) Appl. No.: 18/614,193

(22) Filed: Mar. 22, 2024

(65) Prior Publication Data

US 2024/0316211 A1      Sep. 26, 2024

Related U.S. Application Data

(60) Provisional application No. 63/491,877, filed on Mar. 23, 2023.

(51) Int. Cl.
| | |
|---|---|
| *A61K 47/69* | (2017.01) |
| *A61K 9/00* | (2006.01) |
| *A61K 31/496* | (2006.01) |
| *A61K 31/704* | (2006.01) |
| *A61K 47/54* | (2017.01) |
| *A61P 31/04* | (2006.01) |
| *A61P 35/00* | (2006.01) |

(52) U.S. Cl.
CPC .......... *A61K 47/6901* (2017.08); *A61K 9/007* (2013.01); *A61K 31/496* (2013.01); *A61K 31/704* (2013.01); *A61K 47/545* (2017.08); *A61K 47/6937* (2017.08); *A61P 31/04* (2018.01); *A61P 35/00* (2018.01)

(58) Field of Classification Search
CPC .................................................. A61K 47/6901
See application file for complete search history.

(56) References Cited

U.S. PATENT DOCUMENTS

2013/0337066 A1    12/2013   Zhang

FOREIGN PATENT DOCUMENTS

ID            S202202786 A  *  10/2022

OTHER PUBLICATIONS

Zhang et al., Nanoparticle-modified microrobots for in vivo antibiotic delivery to treat acute bacterial pneumonia, Nature Materials 21, 1324-1332 (2022) doi: 10.1038/s41563-022-01360-9, Sep. 22, 2022.
Zhang et al., Gastrointestinal tract drug delivery using algae motors embedded in a degradable capsule, Science Robotics 7, eabo4160 (2022), Sep. 28, 2022.

* cited by examiner

*Primary Examiner* — Qiuwen Mi
(74) *Attorney, Agent, or Firm* — Meunier Carlin & Curfman LLC

(57)                    ABSTRACT

Microalgae combined with antibiotic-loaded neutrophil membrane-coated polymeric nanoparticles provide a hybrid microrobot having robust locomotion in the lungs in vivo toward effective treatment of pulmonary and gastrointestinal tract infections. The algae-nanoparticle hybrid microrobots are provided in methods of treatment of disease or conditions by administration for active in vivo delivery of therapeutics to the lungs or gastrointestinal tract. The microrobot system can be applied to treat a wide range of diseases, including viral pneumonia.

21 Claims, 20 Drawing Sheets

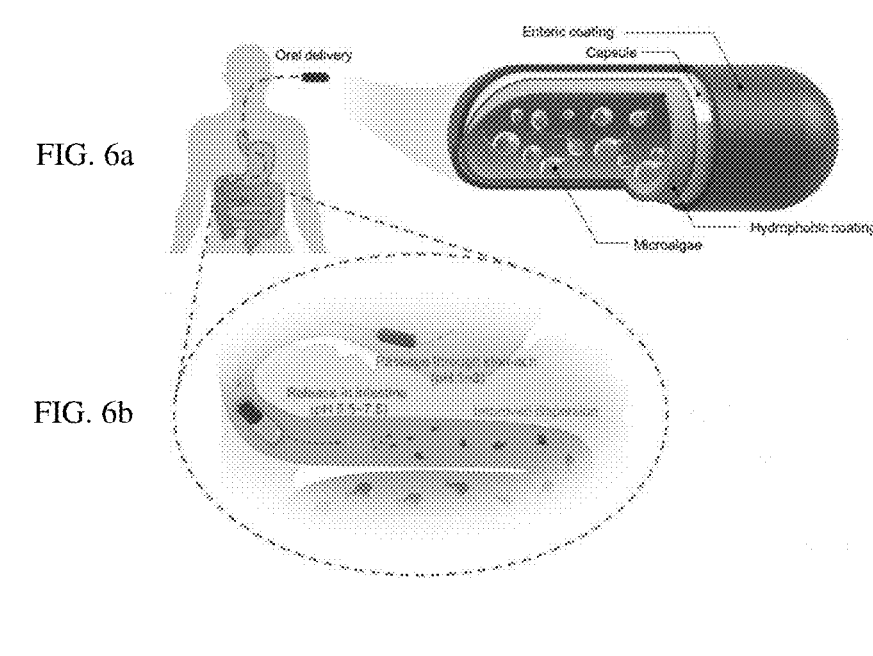
FIG. 6a
FIG. 6b
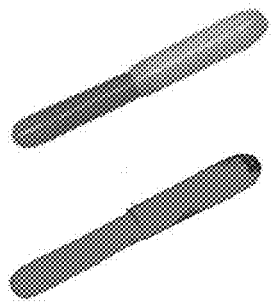
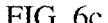
FIG. 6c
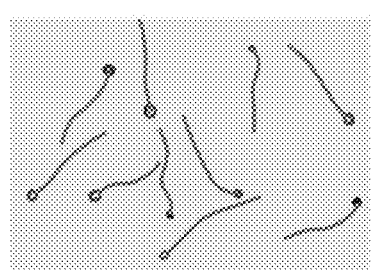
FIG. 6d
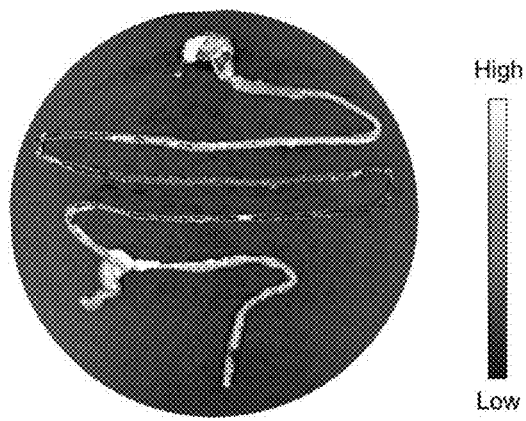
FIG. 6e

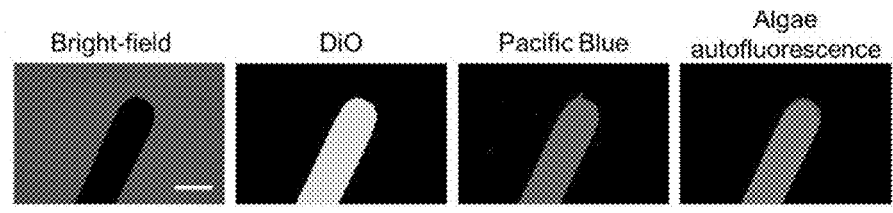
FIG. 8a
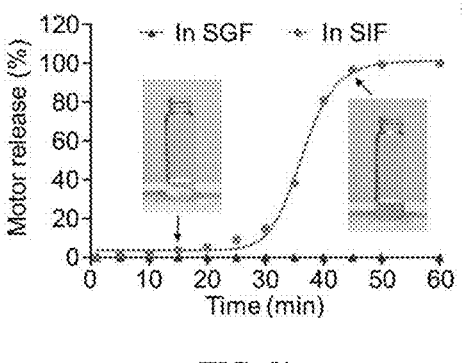
FIG. 8b
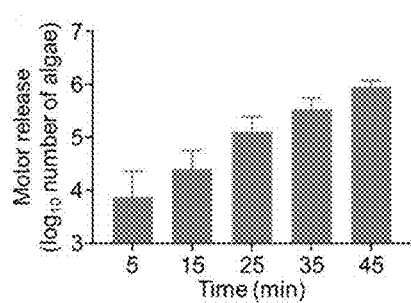
FIG. 8c
Algae in capsule
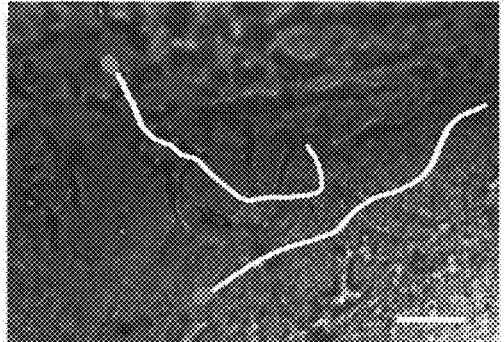
Released algae
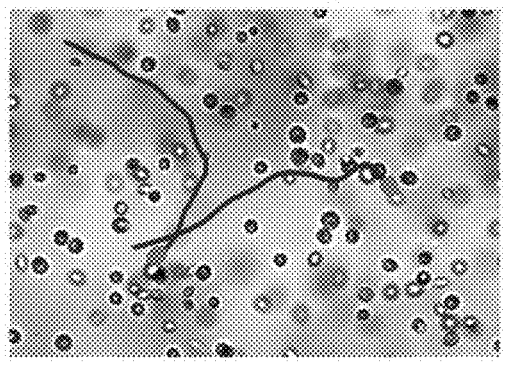
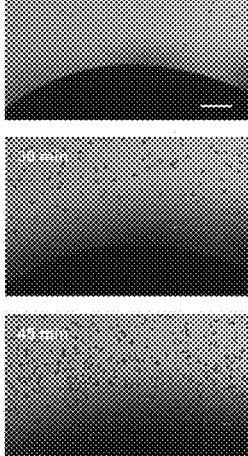
FIG. 8d
FIG. 8e

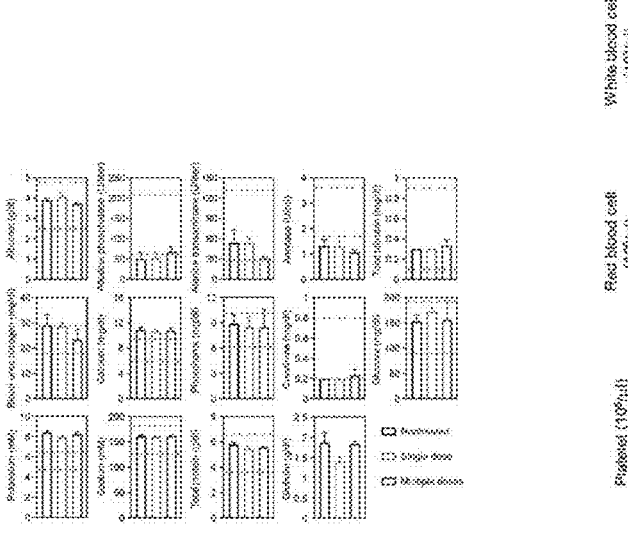
FIG. 12a
FIG. 12b
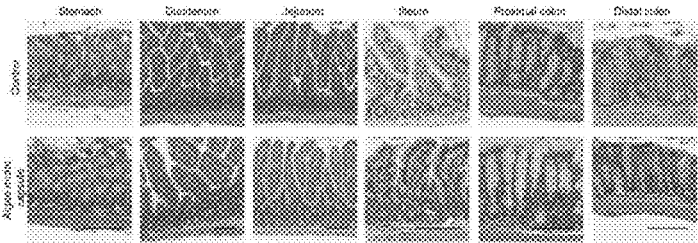
FIG. 12c
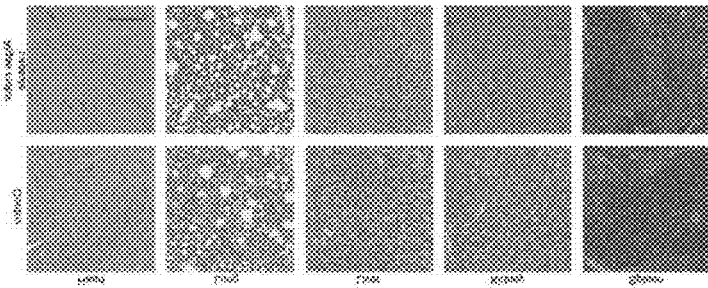
FIG. 12d

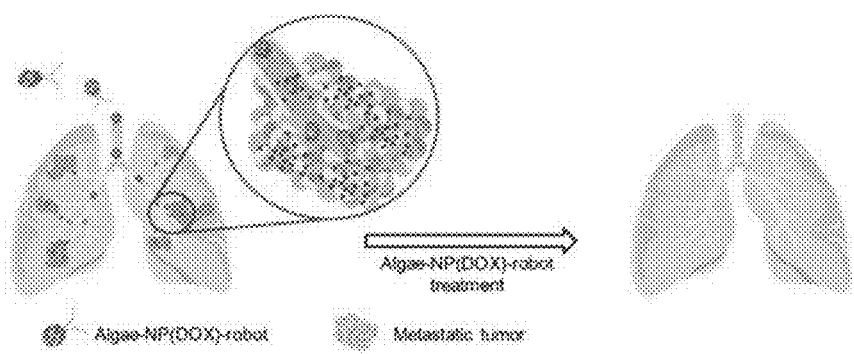
FIG. 13a
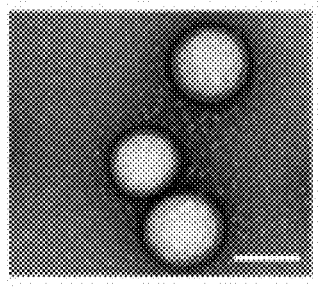
FIG. 13b
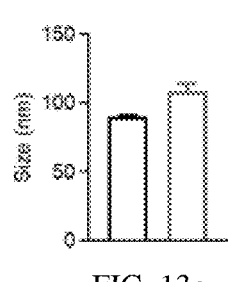
FIG. 13c
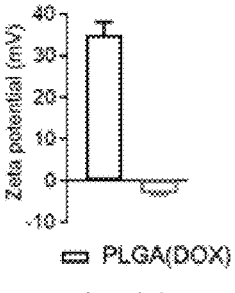
FIG. 13d
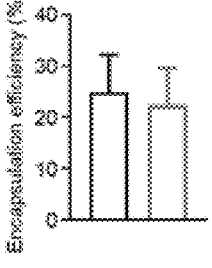
FIG. 13e
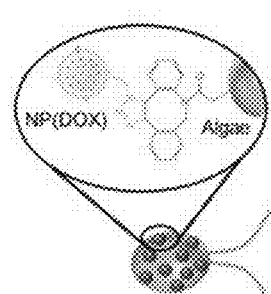
FIG. 13f
FIG. 13g FIG. 17a                    FIG. 17b

ALGAE-BASED MICROROBOT FOR DRUG DELIVERY

CROSS REFERENCE TO RELATED APPLICATIONS

This application claims the priority benefit of U.S. Provisional Application No. 63/491,877, filed Mar. 23, 2023, which application is incorporated herein by reference.

GOVERNMENT SPONSORSHIP

This invention was made with government support under CA200574 and AI175904 awarded by the National Institutes of Health and under HDTRA-21-1-0010 awarded by the Defense Threat Reduction Agency DOD/DTRA). The government has certain rights in the invention.

TECHNICAL FIELD

The present invention relates to an algae-based microrobot for drug delivery.

BACKGROUND

The potential of micro/nanorobots for biomedical applications has been explored extensively over the last decade[1-3]. While early microrobot designs, consisting primarily of rigid metallic or polymeric structures, allowed for various in vitro applications, novel platforms based on biocompatible and deformable materials have offered some unique advantages towards in vivo operations, including improved drug delivery, deep tissue imaging, and precision microsurgery[4-6] The reported in vivo applications of these microrobots were typically restricted to few body locations because of limitations related to the availability of natural fuels, accessibility to certain organs and tissues, and potential toxicity issues. For example, biodegradable zinc and magnesium-based microrobots have been used for drug delivery in the gastrointestinal (GI) tract[7,8]. Magnetically powered microrobots have demonstrated deep penetration in the vitreous humor[6] and actuation in the peritoneal cavity[9,10]. Achieving active propulsion and delivery in other body locations is difficult, but if successful, would offer unprecedented benefits for the treatment of important diseases.

Biohybrid microrobots, which combine the motility of natural organisms with the multifunctionality of synthetic components, have been proposed recently as an attractive alternative to synthetic microrobots towards therapeutic and diagnostic applications[11,12] For instance, *Magnetococcus marinus* magneto-aerotactic bacteria, which swim along local magnetic fields and toward low oxygen concentrations, were used for transporting drugs into tumor hypoxic regions[13]. The natural movement of sperm has been leveraged to construct hybrid microrobots with distinct advantages toward assisted fertilization[14].

*C. reinhardtii*-based microswimmers have been recently used as the microcarriers of synthetic cargo, demonstrating efficient movement and biocompatibilityl[15,16]. They can be facilely cultured and offer self-propulsion based on flagella beating ($\geq 110$ m s$^{-1}$), intrinsic autofluorescence, phototactic guidance and a long lifespan[17]. Neutrophil membrane-coated NPs are used because of their unique cell-mimicking properties, including shielding payloads from biological environments, reducing immune clearance and enabling specific binding with target pathogens[18].

SUMMARY OF THE INVENTION

In embodiments, the invention provides a bioinspired microrobot platform comprising nanoparticle-modified algae for active therapeutic delivery to treat disease. In embodiments, the invention provides active therapeutic delivery to treat disease in the lungs in vivo. In embodiments, the invention provides active therapeutic delivery to treat disease in the gastrointestinal (GI) tract. In embodiments, the invention utilizes the fast, long-lasting swimming behavior of natural microalgae in intestinal fluid to prolong local retention of therapeutic agents within the GI tract.

In embodiments, the present invention provides a hybrid microrobot comprising an algae combined with therapeutic agent-loaded membrane-coated polymeric nanoparticles. In embodiments, the invention provides that the algea is naturally occurring or chemically or genetically modified. In embodiments, the invention provides that the algae is a microalgae such as *C. reinhardtii* algae.

In embodiments, the invention provides that the membrane is a neutrophil membrane or a red blood cell membrane.

In embodiments, the invention provides that the therapeutic agent is an antibiotic agent. In embodiments, the invention provides that the therapeutic agent is ciprofloxacin. In embodiments, the invention provides that the therapeutic agent is an antiviral agent. In embodiments, the invention provides that the therapeutic agent is an anticancer agent. In embodiments, the invention provides that the therapeutic agent is doxorubicin.

In embodiments, the invention provides that the therapeutic agent-loaded nanoparticles are attached onto a surface of the microalgae via click chemistry. In embodiments, the invention provides that the click chemistry comprises an azido-PEG$_4$-NHS ester.

In embodiments, the invention provides that the hybrid microrobot inhibits growth of target bacteria. In embodiments, the invention provides that the hybrid microrobot has locomotive ability of at least 110 $\mu$m s$^{-1}$ in the lungs in vivo. In embodiments, the invention provides that the hybrid microrobot has a tissue retention time of at least 2 days.

In embodiments, the invention provides a method of treating a pulmonary disease or condition comprising administering to a subject in need an effective amount of a hybrid microrobot as described herein. In embodiments, the invention provides that the pulmonary disease is due to an infection by a virus or bacteria. In embodiments, the invention provides that the bacteria is *Pseudomonas aeruginosa*. In embodiments, the invention provides that the disease is caused by a viral pneumonia. In embodiments, the invention provides that the pulmonary disease is caused by a cancer.

In embodiments, the invention provides that the administration is to the lungs of the subject. In embodiments, the invention provides that the administration is intratracheal.

In embodiments, the invention provides a method of treating a gastrointestinal (GI) disease or condition comprising administering to a subject in need an effective amount of a hybrid microrobot as described herein. In embodiments, the invention provides that the GI disease is due to an infection by a virus or bacteria. In embodiments, the invention provides that the bacteria is *Pseudomonas aeruginosa*. In embodiments, the invention provides that the GI disease is caused by a cancer.

In embodiments, the invention provides that the administration is to the gastrointestinal (GI) tract of the subject. In embodiments, the invention provides that the administration is intraesophageal or endogastric.

In embodiments, the invention provides a composition comprising a hybrid microrobot as described herein and a pharmaceutically acceptable carrier.

In embodiments, the invention provides a method of manufacture of a composition for therapeutic use comprising producing the hybrid microrobot by the methods described herein. In embodiments, the invention provides that the therapeutic use is to treat a pulmonary disease or condition, or a GI disease or condition.

BRIEF DESCRIPTION OF THE DRAWINGS

FIGS. 1a-1g show the preparation and structural characterization of the algae-nanoparticle hybrid microrobot (denoted "algae-NP-robot"). FIG. 1a shows a schematic depicting the use of algae-NP-robot for the treatment of a bacterial lung infection. C. reinhardtii algae is modified with drug-loaded NPs and then administered in vivo for the treatment of P. aeruginosa lung infection. The NP is consisting of neutrophil membrane-coated poly(lactic-co-glycolic) (PLGA) core. FIG. 1b shows a schematic of the functionalization of C. reinhardtii with drug-loaded NP using click chemistry. FIG. 1c shows Brightfield and fluorescent images of the NP, in which the PLGA cores are labeled with DiO (green color) and the neutrophil membranes are labeled with DiD (red color). Scale bar: 1 μm. FIG. 1d shows pseudo-colored scanning electron microscopy images of an unmodified algae (left) and an algae-NP-robot (right). Scale bar: 2 μm. FIG. 1e shows a flow cytometric analysis of algae before (left) and after (right) functionalization with DiO-labeled NP. Figure if shows Brightfield and fluorescent images of algae-NP-robot. Autofluorescence of natural algae chloroplast in Cy5 channel; DiO-labeled PLGA cores in GFP channel; DiD-labeled cell membranes in RFP channel. Scale bar: 20 μm. FIG. 1g shows merged images from (f). Cy5 and GFP channels (left); GFP and RFP channels (center); all three channels (right). Scale bar: 20 μm.

FIGS. 3a-3f, Comparison of the speed of bare algae (FIGS. 2a-2b) and algae-NP-robot (d,e) in simulated lung fluid (SLF) at room (RT, 22° C.) and body (37° C.) temperatures (red and blue bars, respectively) (n=6; mean+s.d.). Optical tracking trajectories of the motion of bare algae (FIG. 2c) and algae-NP-robot (f) in SLF (BT, 37° C.) over 1 s (obtained at 0, 15, and 60 min: red, yellow, and orange, respectively). FIGS. 2g-2l show representative trajectories (FIGS. 2g, 2i, and 2k) corresponding to 0 s, 1 s, and 2 s, respectively, and mean speed distribution (FIGS. 2h, 2j, and 2l) of algae-NP-robot in SLF at body temperature (37° C.) after 0 min (FIGS. 2g and 2h), 15 min (FIGS. 2i and 2j), and 60 min (FIGS. 2k and 2l). Scale bar: 50 μm.

FIGS. 3a-3g show 1Lung distribution of algae-NP-robot. FIG. 3a shows ex vivo fluorescent imaging of lungs at various timepoints after intratracheal administration with tris-acetate-phosphate (TAP) medium, algae-NP-robot, or static algae-NP as a negative control (H, high signal; L, low signal). FIG. 3b shows Normalized intensity per gram of tissue of lung samples collected in a (n=3; mean+s.d.). FIG. 3c shows BF and fluorescence microscopy images of representative algae-NP-robot incubated with macrophages at various stages of their interaction. Scale bar, 10 μm. Independent experiments (n=3) were performed with similar results. FIG. 3d shows Macrophage phagocytosis of static algae-NP or algae-NP-robot over time (n=3; mean+s.d.). FIG. 3e shows Relative fluorescence intensity of algae-NP-robot or static algae-NP over time after incubation with macrophage cells in vitro (n=3; mean+s.d.). FIG. 3f shows Representative flow cytometry dot plots of algae-NP-robot (left) and static algae-NP (right) uptake by alveolar macrophages (CD11c+ Siglec-F+) at various timepoints after intratracheal administration in vivo. FIG. 3g shows Comparison of algae-NP-robot and static algae-NP uptake in alveolar macrophages at various timepoints after intratracheal administration in vivo (n=3; mean+s.d.).

FIGS. 4a-4f show in vivo therapeutic efficacy of algae-NP-robot. FIG. 4a, Quantification of Cip loading on different numbers of algae (n=6; mean+s.d.). FIG. 4b, Cumulative drug release profile of NP(Cip) and algae-NP(Cip)-robot (n=3; mean+s.d.). FIG. 4c, Optical density at 600 nm (OD600) measurements of P. aeruginosa treated with the control TAP medium, free Cip, NP(Cip), static algae-NP (Cip) and algae-NP(Cip)-robot (n=3; mean+s.d.). FIG. 4d, In vitro antibacterial activity of free Cip, NP(Cip), static algae-NP(Cip) and algae-NP(Cip)-robot against P. aeruginosa (n=3; geometric mean+s.d.). FIGS. 4e, 4f, In vivo antibacterial efficacy of the control TAP medium, NP(Cip), static algae-NP(Cip) and algae-NP(Cip)-robot with a dosage of 500 ng by intratracheal (IT) administration and free Cip with the same dosage of 500 ng as used in intratracheal administration and a clinical dosage of 1.64 mg by IV administration in P. aeruginosa-infected mice, as determined by bacterial enumeration (n=6; geometric mean+s.d.) (FIG. 4e) and survival (n=12 per group) (FIG. 4f) studies. FIG. 4g, Quantification of bacterial load in the lungs at 24, 48, 72 and 168 h after the algae-NP(Cip)-robot treatment (n=6; geometric mean+s.d.). UD, undetectable. FIGS. 4h 4,i, Experimental timeline (FIG. 4h) and data (FIG. 4i) for the enumeration of bacterial load in the lungs of mice treated with algae-NP(Cip)-robot at different times after challenge with P. aeruginosa (n=6; geometric mean+s.d.). One-way analysis of variance for FIGS. 4e, 4g and 4i and log-rank (Mantel-Cox) test for f.

FIG. 5a, Comprehensive blood chemistry panel taken 24 h after the intratracheal administration of TAP medium or 24, 72 and 168 h after that of algae-NP(Cip)-robot (n=3; mean+s.d.). ALB, albumin; ALP, alkaline phosphatase; ALT, alanine transaminase; AMY, amylase; TBIL, total bilirubin; BUN, blood urea nitrogen; CA, calcium; PHOS, phosphorus; CRE, creatinine; GLU, glucose; NA+, sodium; K+, potassium; TP, total protein; GLOB, globulin. FIG. 5b, Counts of various blood cells 24 h after the intratracheal administration of TAP medium or 24, 72 and 168 h after that of algae-NP(Cip)-robot (n=3; geometric mean+s.d.). WBC, white blood cells; RBC, red blood cells; PLT, platelets. c-e, Haematoxylin and eosin staining of histology sections from major organs 24 h (FIG. 5c), 72 h (FIG. 5d) and 168 h (FIG. 5e) after the intratracheal administration of TAP medium or algae-NP(Cip)-robot. Scale bars, 250 km. Independent experiments (n=3) were performed with similar results. Cytokines, including TNF-α (FIG. 5f), IL-1β (FIG. 5g) and IL-6 (FIG. 5h), measured in the BALF from healthy control mice or 24, 72 and 168 h after the intratracheal administration of algae-NP(Cip)-robot (n=3; mean±s.d.) FIG. 5i, Representative images of haematoxylin and eosin staining on lung histology sections taken from healthy control mice or 24, 72 and 168 h after the intratracheal administration of algae-NP(Cip)-robot. Scale bar, 100 μm. Independent experiments were performed (n=3) with similar results.

FIGS. 6a-6e. Schematic of algae motors in a capsule for GI tract delivery. (FIG. 6a) Algae motors loaded within protective capsules containing an inner hydrophobic coating layer and an outer enteric coating layer can be used for oral delivery applications. (FIG. 6b) The algae motor-loaded capsule first enters the stomach, where the enteric coating protects it from degradation at acidic gastric pH. Upon entering the intestines, the enteric coating is dissolved in the nearly neutral pH and the capsule is degraded, leading to complete release of the algae motors. (FIG. 6c) Bright-field (top) and fluorescent (bottom) images of an algae motor-loaded capsule. Scale bar, 2 mm. (FIG. 6d) Representative tracking trajectories demonstrating the autonomous movement of algae motors in simulated intestinal fluid. (FIG. 6e) Representative biodistribution of fluorescently labeled algae motors in the GI tract 5 hours after administration in a capsule by oral gavage.

(FIG. 7a) Speed of algae motors and Mg motors in SIF during 12 hours of operation (n=5, means±SD). (FIG. 7b) The percentage of motile motors in SIF during a 12-hour period (n=5, means+SD). Time-lapse snapshots and trajectories of algae motors (FIG. 7c) and Mg motors (FIG. 7d) over a span of 2 s at different time points during operation. Scale bars, 50 μm. Time-lapse images showing trajectories over a span of 1 s and corresponding speed distributions of unmodified algae (FIGS. 7e and 7f), fluorescein-labeled algae motors (FIGS. 7g and 7h), and algae motors carrying DiIloaded RBC membrane-coated NPs (FIGS. 7i and 7j) (n=100). Scale bars, 20 μm.

FIG. 8a-8g. Loading and release of algae motors in a capsule in vitro. (FIG. 8a) Bright-field and fluorescence microscopy images of autofluorescence of algae motors (red greyscales) in a capsule formulation fabricated with a DiO-labeled OTMS inner coating (green greyscales) and a Pacific Blue-labeled enteric outer coating (blue greyscales). Scale bar, 1 mm. (FIG. 8b) Release profile of algae motors from a capsule in SGF (blue greyscales line) and SIF (red greyscales line). Inset images correspond to t=15 min (left) and t=45 min (right). (FIG. 8c) Quantification of algae release from capsules over time in SIF (n=3, means+SD). (FIG. 8d) Time-lapse images (t=15, 30, and 45 min) showing the release of algae motors from a capsule in SIF. Scale bar, 100 μm. (FIG. 8e) Representative tracking lines of encapsulated algae motors in TAP medium and released algae motors in SIF. Scale bar, 50 μm. Speed distribution of the encapsulated algae motors (FIG. 8f) and released algae motors (FIG. 8g) from (FIG. 8e) (n=100).

(FIG. 9a) Speed of algae motors and Mg motors at 37° C. in SIF during 12 hours of operation (n=5, means±SD). (FIG. 9) Percentage of motile algae motors and Mg motors at 37° C. in SIF during 12 hours of operation (n=5, means±SD). (FIG. 9c) Representative images of the GI tracts of mice 5 hours after oral administration of fluorescein-labeled algae motors in a capsule (left) or Mg motors in a capsule (right). (FIG. 9d) Quantitative analysis of total fluorescence intensity within the small intestine from the images in (FIG. 9c) (n=3, means+SD). Student's two-tailed t test, **P<0.01.

(FIG. 10a) Representative ex vivo fluorescence images of GI tissues of mice 5 hours after oral administration with TAP medium as a negative control, free algae without a capsule, static algae in a capsule, and algae motors in a capsule. (FIG. 10b) Quantitative analysis of the mean fluorescence from the experiment in (FIG. 10a) (n=3, means+SD). One-way ANOVA, *P<0.001 and **P<0.0001.

(FIG. 11a) Schematic illustration of the fabrication process for the algae-NP(Dox) motor. (FIG. 11b) Bright-field and fluorescence microscopy images visualizing the autofluorescence of algae chloroplasts (red greyscales) and DiO-labeled RBC membrane (green greyscales) to demonstrate the loading of Dox-loaded NPs onto an algae motor. Scale bar, 5 μm. (FIG. 11c) SEM image of an algae motor loaded with NP(Dox). Scale bar, 2.5 μm. Inset shows a zoomed-in view corresponding to the dashed red box. Scale bar, 200 nm. (FIG. 11d) Quantification of drug loading amount and loading efficiency of 1×106 algae-NP(Dox) at different Dox inputs (n=3, means±SD). Mean (Figure lie) and median (FIG. 11f) speed of algae-NP(Dox) motor and bare algae. The speed was measured from 100 individual alga. (FIG. 11g) The cumulative drug release profiles from the algae-NP(Dox) motor and NP(Dox) (n=3, means±SD). (FIG. 11h) Viability of B16-F10 cancer cell lines after 24, 48, and 72 hours of incubation with blank solution, bare algae, NP(Dox), and algae-NP(Dox) motor (n=3, means±SD). (FIG. 11i) Quantification of the total Dox content per small intestine at different times after administration of the algae-NP(Dox) motor and NP(Dox) in a capsule (n=3, means+SD). Student's multiple t test, *P<0.05, P<0.01, and *P<0.001.

FIGS. 12a-12d. In vivo safety analysis of algae motors after oral administration. Comprehensive blood chemistry panel (FIG. 12a) and blood cell counts (FIG. 12b) taken from non-treated mice, mice with single-dose treatment, and mice with multiple-dose treatment (n=3, means+SD). For single-dose evaluation, mice were orally administered with one algae motor capsule on day 0, and blood samples were collected on day 1. For multiple-dose evaluation, mice were orally administered with one algae motor capsule on days 0, 2, 4, and 6. Blood samples were collected on day 7. The green dashed lines indicate the mouse reference ranges of each analyte. (FIG. 12c) Representative H&E stained histological sections from different sections of the GI tract from nontreated mice and mice treated with the algae motors in a capsule 24 hours after oral administration. Scale bars, 100 μm. (FIG. 12d) H&E-stained histological sections of major organs, including the heart, lungs, liver, kidneys, and spleen, from nontreated mice and mice treated with the algae motors in a capsule 24 hours after oral administration. Scale bar, 250 μm.

FIGS. 13a-13l. Preparation and characterization of algae-NP(DOX)-robot. FIG. 13a, Schematic depicting the use of algae-NP(DOX)-robot for the treatment of melanoma lung metastasis. FIG. 13b, TEM image of red blood cell membrane-coated DOX-loaded nanoparticles (denoted "NP (DOX)"). Scale bar, 100 nm. Size (FIG. 13c) and surface zeta potential (FIG. 13d) of NP(DOX) and bare DOX-loaded polymeric nanoparticles (denoted "PLGA(DOX)") (n=3; mean+s.d.). Drug loading yield (FIG. 13e) and encapsulation efficiency (f) of NP(DOX) and PLGA(DOX) (n=3; mean+s.d.). FIG. 13g, Schematic illustration of algae-NP (DOX)-robot, in which NP(DOX) is covalently conjugated onto algae via click chemistry. FIG. 13h, Representative bright-field (BF) and fluorescent images of an algae-NP (DOX)-robot. Autofluorescence of algae chloroplast in the Cy5 channel; NP(DOX) in the RFP channel. Scale bar, 10 m FIG. 13i, Pseudo-colored SEM image of an algae-NP (DOX)-robot. Algae in green greyscales; NP(DOX) in orange greyscales. Scale bar, 2 μm. FIG. 13j, Optical absorption spectrum of algae-NP(DOX)-robot compared with bare algae and NP(DOX). FIG. 13k, Quantification of DOX loading on 1×10$^6$ algae at various initial drug inputs (n=3; mean±s.d.). FIG. 13l, Representative flow cytometry histograms of algae before (grey) and after (red) functionalization with NP(DOX) at a 25-μg drug input. DOX is measured on the PE channel.

Figures 14A, 14B, 14C, 14D, 14E, 14F, 14G, 14H, 14I, 14J, 14K:
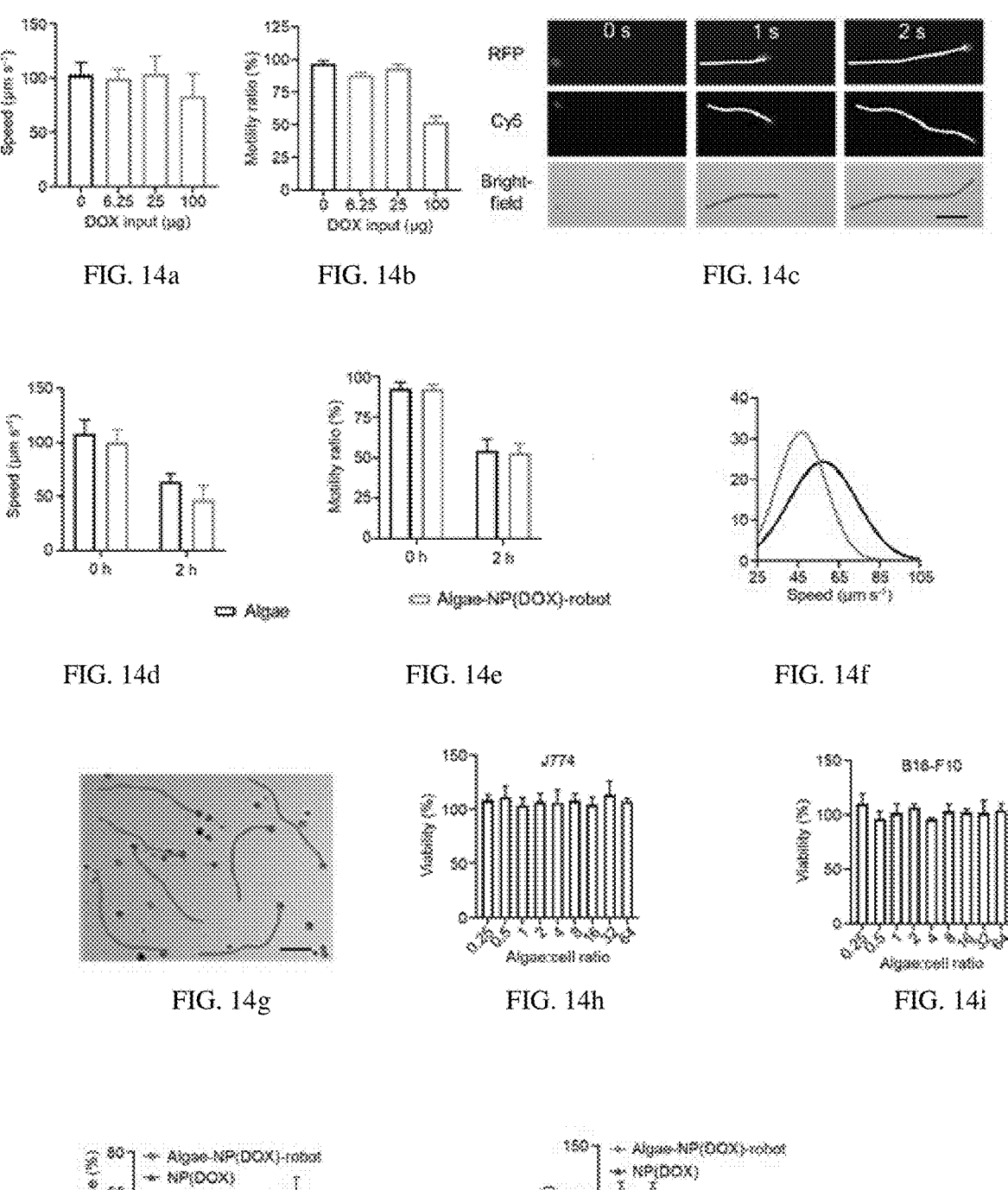

FIGS. 14a-14k. Motion behavior and in vitro characterizations of algae-NP(DOX)-robot. Speed (FIG. 14a) and motility ratio (FIG. 14b) of algae-NP(DOX)-robot at different drug inputs in water at 22° C. (n=10 for a and n=5 for b; mean+s.d.). FIG. 14c, Snapshot of self-propelled motion of algae-NP(DOX)-robot over 2 s in water at 22° C. under fluorescence and optical microscopes. NP(DOX) in the RFP channel; autofluorescence of algae chloroplast in the Cy5 channel. Scale bar, 50 μm. Speed (FIG. 14d) and motility ratio (FIG. 14e) of bare algae and algae-NP(DOX)-robot before and after 2 h of motion in simulated lung fluid (SLF) at 37° C. (n=10 for d and n=5 for e; mean+s.d.). FIG. 14f, Swimming velocity analyses of bare algae and algae-NP(DOX)-robot after 2 h of motion in SLF at 37° C. FIG. 14g, Swimming trajectories of algae-NP(DOX)-robot over 5 s in SLF at 37° C. Scale bar, 50 km. Viability of J774 macrophages (FIG. 14h) and B16-F10 cancer cells (FIG. 14i) after 24 h of incubation with NP-functionalized algae without DOX at varying algae-to-cell ratios (n=3; mean+s.d.). FIG. 14j, Drug release profiles of algae-NP(DOX)-robot and NP(DOX) (n=3; mean±s.d.). FIG. 14k, In vitro anticancer activity of NP(DOX) and algae-NP(DOX)-robot against B16-F10 melanoma cells after 24 h of incubation (n=3; mean±s.d.).

Figures 15A, 15B, 15C, 15D, 15E, 15F, 15G, 15H, 15I:
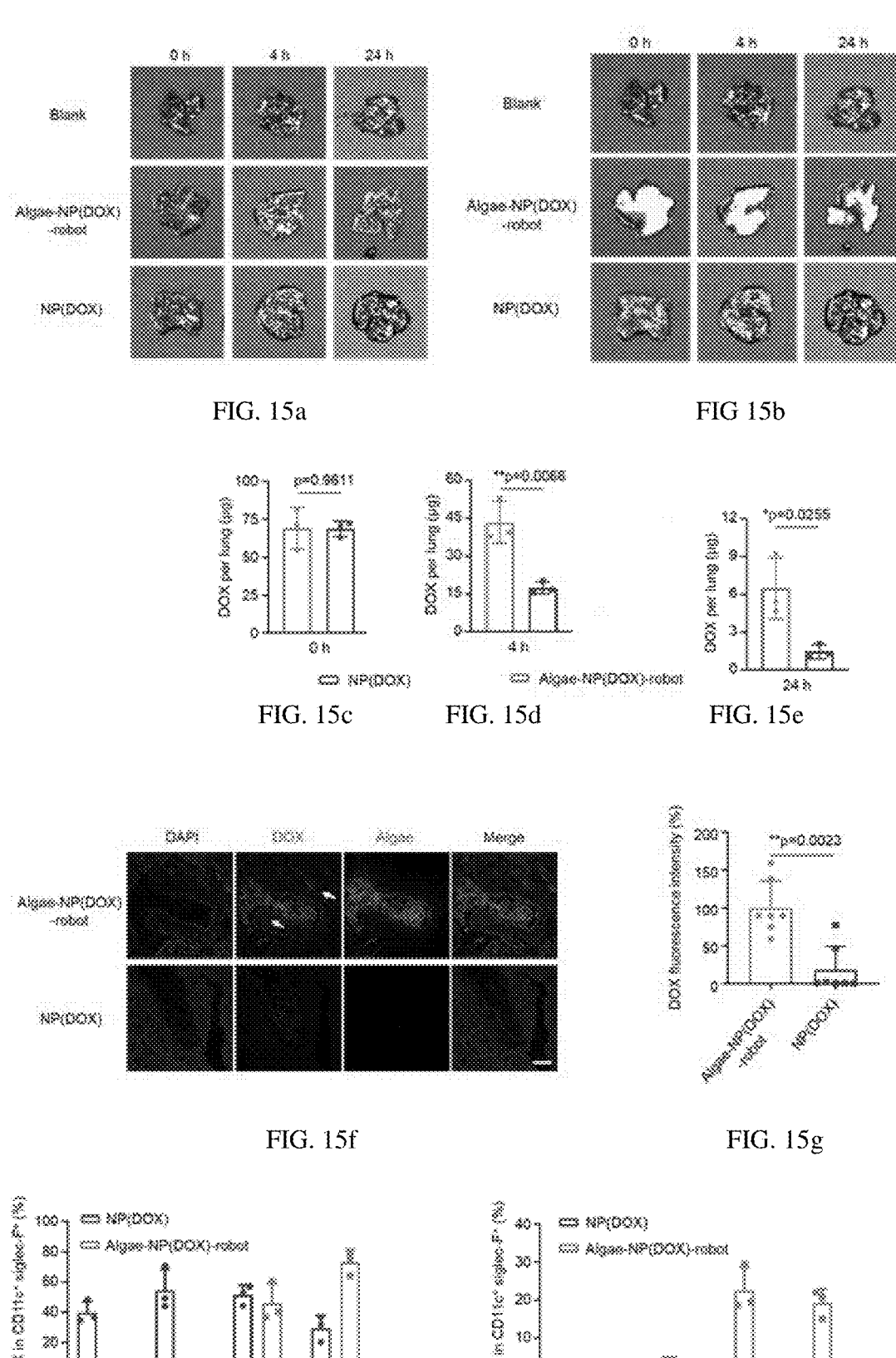

FIGS. 15a-15i. In vivo biodistribution and drug retention of algae-NP(DOX)-robot. Lung distribution of DOX (FIG. 15a) and microalgae (FIG. 15b) examined by ex vivo fluorescence imaging at various timepoints after intratracheal administration of algae-NP(DOX)-robot or NP(DOX). Drug accumulation in the lungs at 0 h (FIG. 15c), 4 h (FIG. 15d), and 24 h (FIG. 15e) after intratracheal administration of algae-NP(DOX)-robot or NP(DOX) (n=3; mean±s.d.). FIG. 15f, Representative lung tissue section showing DOX distribution at 24 h after intratracheal administration of algae-NP(DOX)-robot or NP(DOX). White arrows indicate the signal from DOX penetrated the deep lung tissue. Scale bar, 200 μm. FIG. 15g, Lung drug retention based on the quantification of total DOX fluorescence intensity in histological sections (n=7; mean+s.d.). DOX (FIG. 15h) and algae (FIG. 15i) uptake in alveolar macrophage at various timepoints after intratracheal administration of algae-NP(DOX)-robot or NP(DOX) (n=3; mean+s.d.). Student's t-test for FIGS. 15c-15e and 15g, *p<0.05 and **p<0.01.

Figure 16A:
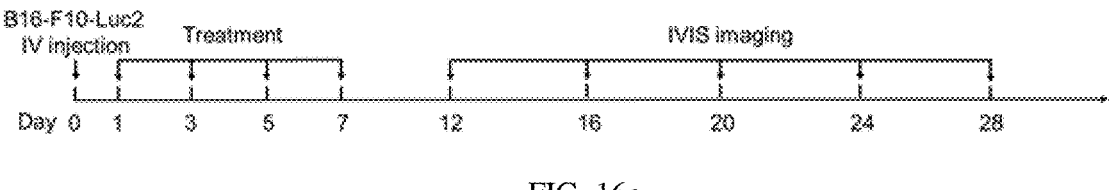
Figure 16B:
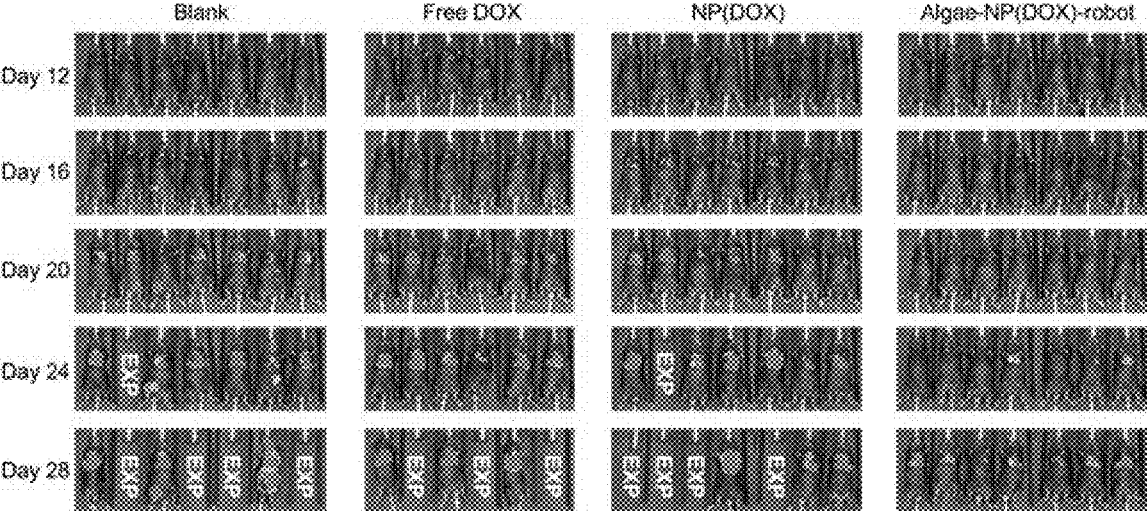
Figure 16C:
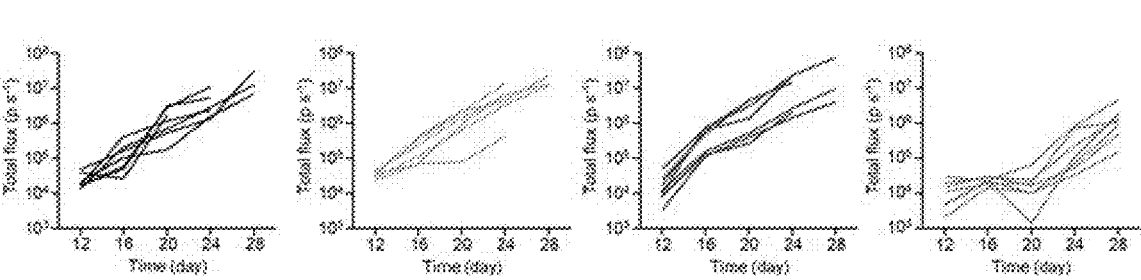
Figures 16D, 16E, 16F, 16G:
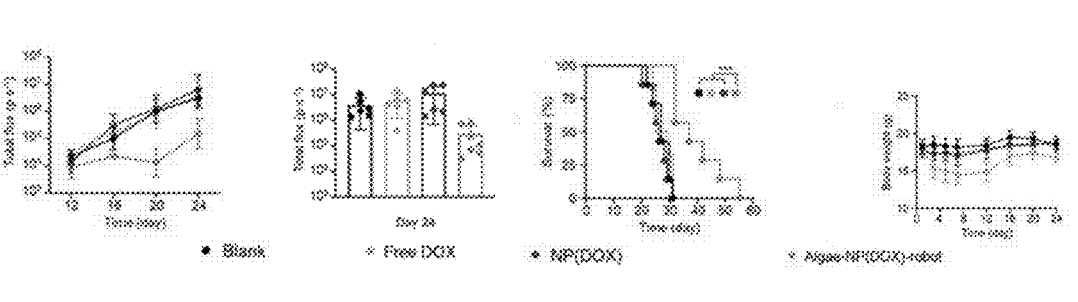

FIGS. 16a-16g. Therapeutic efficacy of algae-NP(DOX)-robot against melanoma lung metastasis. FIG. 16a, Schematic diagram showing the experimental timeline; mice were treated with free DOX, NP(DOX), or algae-NP(DOX)-robot. FIG. 16b, Bioluminescence images of mice at different timepoints. FIG. 16c, Quantification of bioluminescence intensity of individual mice over time (n=6 or 7). FIG. 16d, Quantification of total bioluminescence intensity over time (n=6 or 7; mean±s.d.). FIG. 16e, Comparison of total bioluminescence intensity on day 24 (n=6 or 7; mean±s.d.). FIG. 16f, Survival after treatment (n=6 or 7). FIG. 16g, Body weight over time (n=6 or 7; mean±s.d.). Log-rank (Mantel-Cox) test for f, ***p<0.001 (compared to algae-NP(DOX)-robot).

Figure 17C:
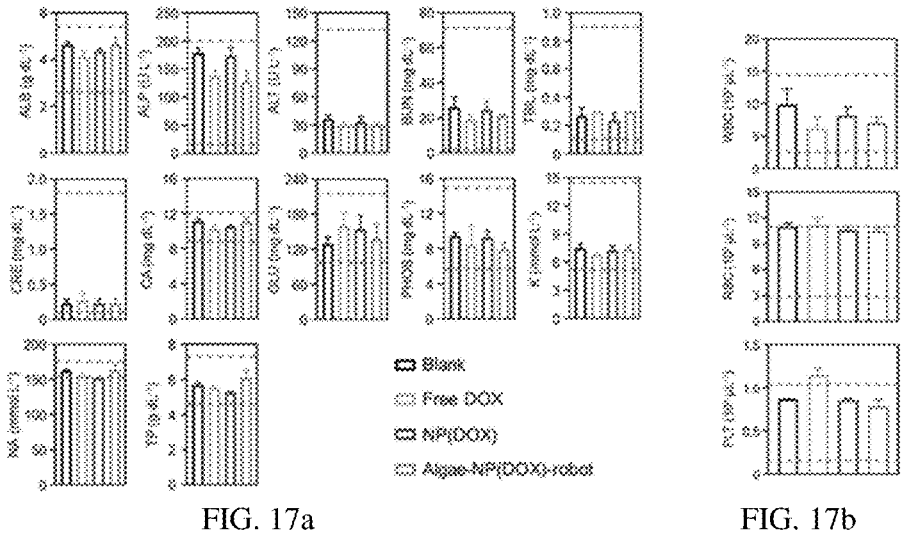
Figure 17C:
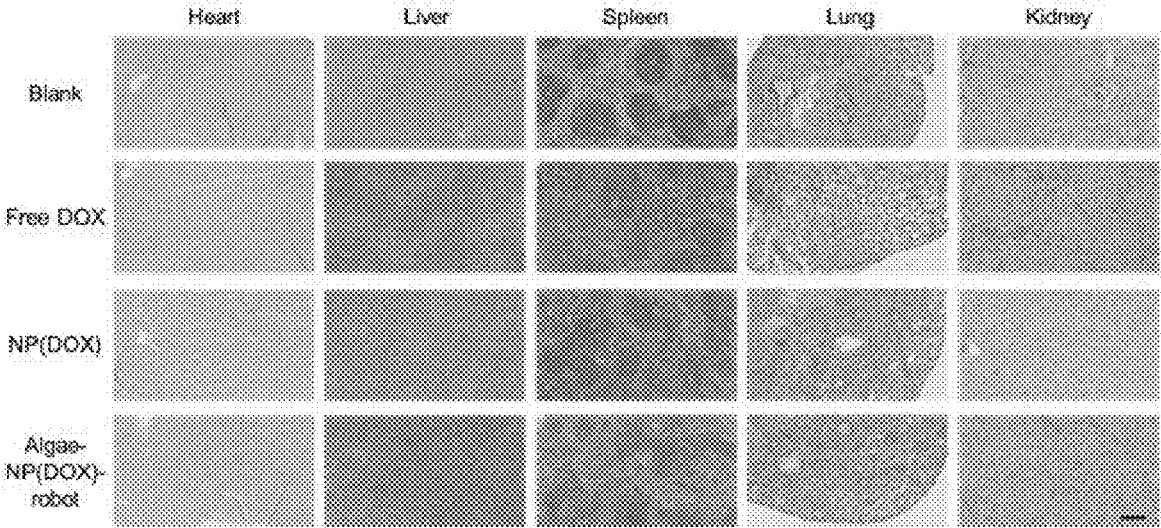

FIGS. 17a-17c show in vivo safety evaluation of algae-NP(DOX)-robot. Comprehensive blood chemistry panel (FIG. 17a) and blood cell counts (FIG. 17b) of untreated mice, as well as mice administered intratracheally with free DOX, NP(DOX) or algae-NP(DOX)-robot on days 0, 2, 4, and 6 (n=3; mean±s.d.); blood samples were collected 24 h after the last dose. ALB, albumin; ALP, alkaline phosphatase; ALT, alanine transaminase; BUN, blood urea nitrogen; TBIL, total bilirubin; CRE, creatinine; CA, calcium; PHOS, phosphorus; K, potassium; NA, sodium; TP, total protein. The grey dashed lines represent the mouse reference ranges for each parameter. FIG. 17c, H&E-stained histological sections of major organs, including the heart, liver, spleen, lungs, and kidneys, from untreated mice and mice administered intratracheally with free DOX, NP(DOX) or algae-NP(DOX)-robot on days 0, 2, 4, and 6; tissue samples were collected 24 h after the last dose. Scale bar, 200 km.

DETAILED DESCRIPTION

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

The present disclosure expressly incorporates by reference herein in its entirety the publications: Zhang et al., Nanoparticle-modified microrobots for in vivo antibiotic delivery to treat acute bacterial pneumonia, Nature Materials 21, 1324-1332 (2022) doi: 10.1038/s41563-022-01360-9, 22 Sep. 2022; and Zhang et al., Gastrointestinal tract drug delivery using algae motors embedded in a degradable capsule, Science Robotics 7, eabo4160 (2022), 28 Sep. 2022.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a hybrid microrobot, a pharmaceutical composition, and/or a method that "comprises" a list of elements (e.g., components, features, or steps) is not necessarily limited to only those elements (or components or steps), but may include other elements (or components or steps) not expressly listed or inherent to the hybrid microrobot, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a hybrid microrobot, pharmaceutical composition, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The terms "subject," "patient" and "individual" are used interchangeably herein to refer to a vertebrate, preferably a mammal, more preferably a human. Tissues, cells, and their progeny of a biological entity obtained in vivo or cultured in vitro are also encompassed. A "subject," "patient" or "individual" as used herein, includes any animal that can be treated with the hybrid microrobot, compositions, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

The hybrid microrobots and pharmaceutical compositions of the disclosure may be administered in a number of ways depending upon whether local or systemic treatment is desired. The hybrid microrobots or pharmaceutical compositions are typically suitable for oral, buccal, nasal, pulmonary or parenteral administration. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal, intravenous, intranasal, intratracheal, gastrointestinal, intraarterial, intrathecal, intraventricular, intraurethral, intracranial, intratumoral, intraocular, intradermal, intrasynovial injection or infusions, intra-tumoral; and kidney dialytic infusion techniques. In some embodiments, the immune cells, or pharmaceutical compositions of the present disclosure comprise intravenous administration. In some embodiments, the hybrid microrobots, or pharmaceutical compositions of the present disclosure comprise intra-tumoral administration.

In embodiments, the present invention provides a hybrid microrobot comprising a motile algae conjugated with a therapeutic agent-loaded membrane-coated polymeric nanoparticle. In embodiments, the invention provides that the algae is naturally occurring or chemically or genetically modified. In embodiments, the invention provides that the algae is a microalgae such as *Chlamydomonas reinhardtii* algae.

In embodiments, the invention provides that the membrane is a cellular membrane. In embodiments, the cellular membrane is a neutrophil membrane. In embodiments, the invention provides that the membrane is a red blood cell membrane. Membrane coated nanoparticles can be constructed as described in US Patent Publication US2013/0337066, which is incorporated herein by reference.

In embodiments, the invention provides that the membrane-coated polymeric nanoparticle comprises a) an inner core comprising a non-cellular material; and b) an outer surface comprising a cellular membrane derived from a cell or a membrane derived from a virus.

In certain embodiments, the inner core of the nanoparticle comprises a biocompatible and/or a synthetic material including but not limited to, poly(lactic-co-glycolic acid), polylactic acid, polyglycolic acid, polycaprolactone, polylysine, polyglutamic acid, and any other suitable synthetic material or the like. In embodiments, the invention provides that the polymeric nanoparticle comprises poly(lactic-co-glycolic acid) (PLGA).

In certain embodiments, the outer surface of the nanoparticle comprises cellular membrane comprising plasma membrane or an intracellular membrane derived from a unicellular (e.g. a bacterium or fungus) or multicellular organism (e.g., a plant, an animal, a non-human mammal, vertebrate, or a human). In certain embodiments, the outer surface of the nanoparticle comprises a naturally occurring cellular or viral membrane and/or further comprises a synthetic membrane.

In certain embodiments, the cellular membrane of the outer surface of the nanoparticle is derived from a blood cell (e.g., red blood cell (RBC), white blood cell (WBC), or platelet). In certain embodiments, the cellular membrane of the nanoparticle is derived from a cell of the same species of the subject or is derived from a cell of the subject. In certain embodiments, the cellular membrane of the nanoparticle used for the inventive method is derived from a red blood cell of the same species of the subject and the red blood cell has the same blood type of the subject. In other embodiments, the cellular membrane of the outer surface is derived from an immune cell (e.g., macrophage, monocyte, B-cell, or T-cell), a tumor or cancer cell, and other cells, such as an epithelial cell, an endothelial cell, or a neural cell. In other embodiments, the cellular membrane of the outer surface is derived from a non-terminally differentiated cell, such as a stem cell, including a hematopoietic stem cell, a bone marrow stem cell, a mesenchymal stem cell, a cardiac stem cell, a neural stem cell. The non-terminally differentiated cell can be isolated in a pluripotent state from tissue or induced to become pluripotent. In yet other embodiments, the cell membrane is derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

In certain embodiments, the present invention further provides that the nanoparticle comprises a releasable therapeutic cargo that can be located in any place inside or on the surface of the nanoparticle. A trigger for releasing the releasable cargo from the inventive nanoparticle includes, but is not limited to, contact between the nanoparticle and a target cell, tissue, organ or subject, or a change of an environmental parameter, such as the pH, ionic condition, temperature, pressure, and other physical or chemical changes, surrounding the nanoparticle. In certain embodiments, the releasable cargo comprises one or more therapeutic agent, prophylactic agent, diagnostic or marker agent, prognostic agent, e.g., an imaging marker, or a combination thereof. In yet certain other embodiments, the releasable cargo is a metallic particle, a polymeric particle, a dendrimer particle, or an inorganic particle.

The present nanoparticle can have any suitable shape. For example, the present nanoparticle and/or its inner core can have a shape of sphere, square, rectangle, triangle, circular disc, cube-like shape, cube, rectangular parallelepiped (cuboid), cone, cylinder, prism, pyramid, right-angled circular cylinder and other regular or irregular shape. The present nanoparticle can have any suitable size. The present invention further provides that in certain embodiments the inventive nanoparticle has a diameter from about 10 nm to about 10 μm. In certain embodiments, the diameter of the invention nanoparticle is about 50 nm to about 500 nm. In other embodiments, the diameter of the nanoparticle can be about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 μm, 2 μm, 3 μm, 4 μm, 5 μm, 6 μm, 7 μm, 8 μm, 9 μm, and 10 μm, or any suitable sub-ranges within the about 10 nm to about 10 μm range, e.g., a diameter from about 50 nm to about 150 nm. In certain embodiments, the inner core supports the outer surface.

The present invention further provides that the nanoparticle substantially lacks constituents of the cell from which the cellular membrane is derived or constituents of the virus from which the viral membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the constituents of the cell from which the cellular membrane is derived or constituents of the virus from which the viral membrane is derived.

In yet certain other embodiments, the nanoparticle of the present invention substantially maintains natural structural integrity or activity of the cellular membrane, the membrane derived from a virus or the constituents of the cellular membrane or viral membrane. The structural integrity of the cellular membrane includes primary, secondary, tertiary or quaternary structure of the cellular membrane, the membrane derived from a virus or the constituents of the cellular membrane or viral membrane, and the activity of the cellular membrane includes, but is not limited to, binding activity, receptor activity, signaling pathway activity, and any other activities a normal naturally occurring cellular membrane, the membrane derived from a virus or the constituents of the cellular membrane or viral membrane, would have. In certain embodiments, the nanoparticle of the present invention is biocompatible and/or biodegradable. For example, the present nanoparticle can maintain, in terms of types and/or quantities, at least 10%, 20%, 30%, 40%, 50%, 60%, 70%, 80%, 90%, 95%, 96%, 97%, 98%, 99% or 100% of the natural structural integrity or activity of the cellular membrane, the membrane derived from a virus or the constituents of the cellular membrane or viral membrane.

In certain embodiments, the nanoparticle of the present invention comprises the cellular plasma membrane derived from a red blood cell and an inner core comprising poly (lactic-co-glycolic acid) (PLGA), wherein the nanoparticle substantially lacks hemoglobin. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the hemoglobin of the red blood cell from which the plasma membrane is derived.

Such inventive nanoparticle has a half-life in blood circulation in vivo at least about 2-5 times of a half-life of a polyethylene glycol (PEG)-coated, comparable nanoparticle. In certain embodiments, such inventive nanoparticle has a half-life in blood circulation in vivo for at least about 5 to about 40 hours or longer.

In certain embodiments, the invention nanoparticle substantially lacks immunogenicity to a species or subject from which the cellular membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the immunogenicity to a species or subject from which the cellular membrane is derived.

In embodiments, the invention provides that the therapeutic agent is an antibiotic agent. In embodiments, the invention provides that the therapeutic agent is ciprofloxacin. In embodiments, the invention provides that the therapeutic agent is an antiviral agent. In embodiments, the invention provides that the therapeutic agent is an anticancer agent. In embodiments, the invention provides that the therapeutic agent is doxorubicin.

In embodiments, the invention provides that the therapeutic agent-loaded nanoparticles are attached onto a surface of the microalgae via click chemistry. In embodiments, the invention provides that the click chemistry comprises an azido-PEG$_4$-NHS ester. In embodiments, the invention provides that the algae has a surface modified with azido-PEG$_4$-N-hydroxysuccinimide (NHS) ester, and is conjugated with dibenzocyclooctyne (DBCO)-PEG$_4$-NHS ester modified membrane-coated polymeric nanoparticles.

In embodiments, the invention provides that the hybrid microrobot is embedded inside a pH-sensitive capsule for gastrointestinal delivery.

In embodiments, the invention provides that the hybrid microrobot inhibits growth of target bacteria. In embodiments, the invention provides that the hybrid microrobot has locomotive ability of at least 110 $\mu$m s$^{-1}$ in the lungs in vivo. In embodiments, the invention provides that the hybrid microrobot has a tissue retention time of at least 2 days.

In embodiments, the invention provides a method of treating a pulmonary disease or condition comprising administering to a subject in need an effective amount of a hybrid microrobot as described herein. In embodiments, the invention provides that the pulmonary disease is due to an infection by a virus a bacteria or a cancer. In embodiments, the invention provides that the bacteria is *Pseudomonas aeruginosa*. In embodiments, the invention provides that the disease is caused by a viral pneumonia. In embodiments, the invention provides that the disease is caused by a cancer.

In embodiments, the invention provides that the administration is to the lungs of the subject. In embodiments, the invention provides that the administration is intratracheal.

In embodiments, the invention provides a method of treating a gastrointestinal (GI) disease or condition comprising administering to a subject in need an effective amount of a hybrid microrobot as described herein. In embodiments, the invention provides that the GI disease is due to an infection by a virus or bacteria. In embodiments, the invention provides that the bacteria is *Pseudomonas aeruginosa*. In embodiments, the invention provides that the GI disease is caused by a cancer.

In embodiments, the invention provides that the administration is to the gastrointestinal (GI) tract of the subject. In embodiments, the invention provides that the administration is intraesophageal or endogastric.

In embodiments, the invention provides treatments, prevention, diagnosis and/or prognosis of any diseases, disorders, or physiological or pathological conditions, including, but not limited to, an infectious disease, a parasitic disease, a neoplasm, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.

In embodiments, the invention provides a composition comprising a hybrid microrobot as described herein and a pharmaceutically acceptable carrier.

In embodiments, the invention provides a method of manufacture of a composition for therapeutic use comprising producing the hybrid microrobot by the methods described herein. In embodiments, the invention provides that the therapeutic use is to treat a pulmonary disease or condition, or a GI disease or condition.

Various further aspects and embodiments of the disclosure are provided by the following description. Before further describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description. All of the compositions and methods of production and application and use thereof disclosed herein can be made and executed without undue experimentation in light of the present disclosure.

EXAMPLES

Figure 1A:
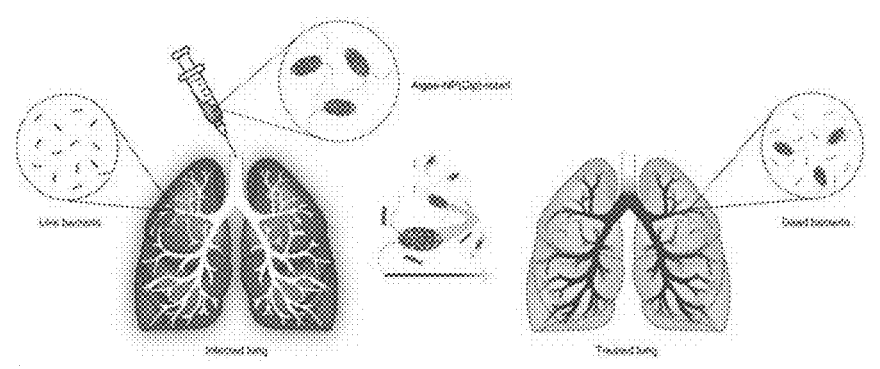

Example 1: Nanoparticle-Modified Microrobots for In Vivo Antibiotic Delivery to Treat Acute Bacterial Pneumonia This example provides a bioinspired microrobot platform comprising nanoparticle (NP)-modified algae for active therapeutic delivery. The example provides a biohybrid microrobot comprising natural *Chlamydomonas reinhardtii* microalgae modified with neutrophil membrane-coated drug-loaded polymeric nanoparticles (denoted 'algae-NP-robot') for in vivo treatment of lung infection (FIG. 1a). In the present example, the unique properties of natural algae are combined with the engineering versatility and drug-carrying capacity of biomimetic nanoparticles to construct a hybrid microrobot platform capable for active drug delivery.

Among the numerous applicable conditions, this example tested the algae-NP-robot for in vivo antibiotic delivery to treat bacterial lung infections. Specifically, ventilator-associated pneumonia (VAP) is an acute and potentially fatal infection characterized by onset 48 h after the initiation of mechanical ventilation in intensive care unit (ICU) settings[19]. VAP represents one of the most common infections among hospital patients, affecting between 10% and 25% of those who are intubated[21], resulting in considerable mortality, prolonged ICU stays and an increased number of days on ventilation[21-23]. Multidrug-resistant pathogens such as *Pseudomonas aeruginosa* are becoming increasingly prevalent as antibiotics continue to be indiscriminately used and with waning effectiveness[24]. Pulmonary antibiotic delivery efficiency could benefit from the deep tissue penetration and prolonged drug retention enabled by the algae-NP-robot system in an experimental model of VAP.

To transform the microalgae into algae-NP-robot active delivery system, the algae surface was first modified with azido N-hydroxysuccinimide (NHS) ester[25, 26], followed by conjugation with dibenzocyclooctyne (DBCO)-modified neutrophil membrane-coated polymeric nanoparticles through efficient click chemistry (FIG. 1b). Such click chemistry has been used for cell modification towards cell-cell conjugation[27], targeted immunomodulation of dendritic cells in vivo[28], and engineered hematopoietic stem cell delivery[29]. The motion and cargo-carrying behavior of the resulting algae-NP-robot in simulated lung fluid (SLF), combined with their uniform distribution, effective inhibition of macrophage phagocytosis and prolonged retention in lung tissue, was verified and highlights the considerable promise for in vivo drug delivery. The significant therapeutic efficacy and safety of the drug-loaded algae-NP-robot are demonstrated using a murine model of *P. aeruginosa* lung infection.

Figure 1D:
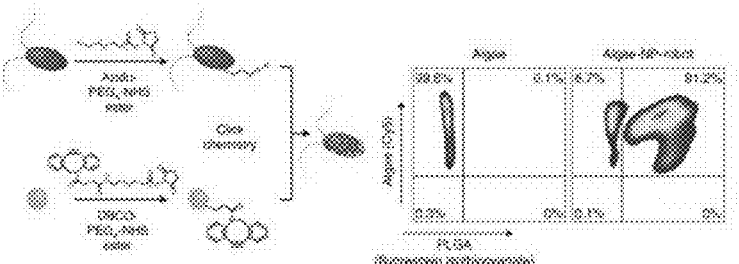
Figure 1D:
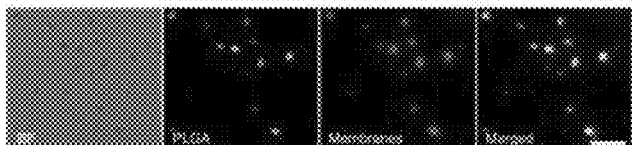
Figure 1E:
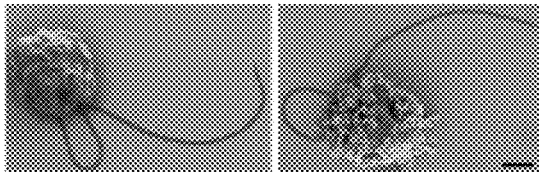
Figure 1F:
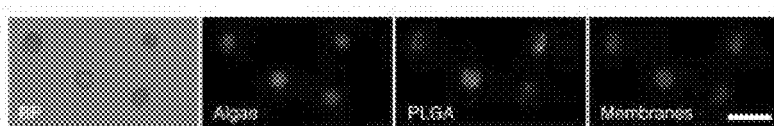
Figure 1G:
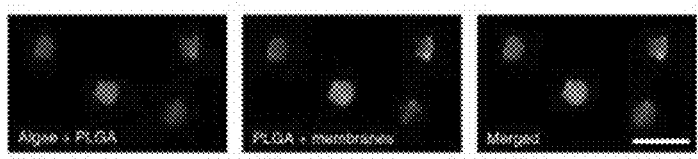

Preparation of algae-NP-robot. Natural *C. reinhardtii* green algae were cultivated in Tris-acetate-phosphate (TAP) medium for further modification. For further modification, the algae were conjugated with azido-PEG$_4$-NHS ester, which reacts with primary amines on the algal surface. The algae functionalization was confirmed, and negligible cytotoxicity was observed. We then fabricated neutrophil membrane-coated poly(lactic-co-glycolic acid) (PLGA) NPs[30] for use as a therapeutic payload. For visualization, the hydrophobic dyes 1,1'-dioctadecyl-3,3,3',3'-tetramethylindocarbocyanine perchlorate (DiI) and 3,3'-dioctadecyloxacarbocyanine perchlorate (DiO) were loaded into the PLGA cores and neutrophil membranes, respectively. The overlap of both fluorescence signals indicated the successful association of the two components (FIG. 1c). The NPs were further characterized by dynamic light scattering, transmission electron microscopy (TEM) and immunostaining, verifying their core-shell structure and right-side-out membrane orientation. The surface of the NPs was further reacted with DBCO-PEG$_4$-NHS ester, and successful modification was qualitatively confirmed by fluorescence microscopy using an azide-functionalized dye. Conjugation to the algal surface was achieved through click chemistry by incubating the azido-modified algae with DBCO-modified NPs. Scanning electron microscopy (SEM) imaging confirmed the formation of NP-modified algae (FIG. 1d). By optimizing the NP input concentration, 91.2% of the algae population could be conjugated with NPs (FIG. 1e). Fluorescence microscopy was used to confirm that the NPs were firmly attached to the algal surface after multiple washing steps (FIGS. 1f, 1g).

Figures 2A, 2B, 2C, 2D, 2E, 2F, 2G, 2H, 2I, 2J, 2K, 2L:
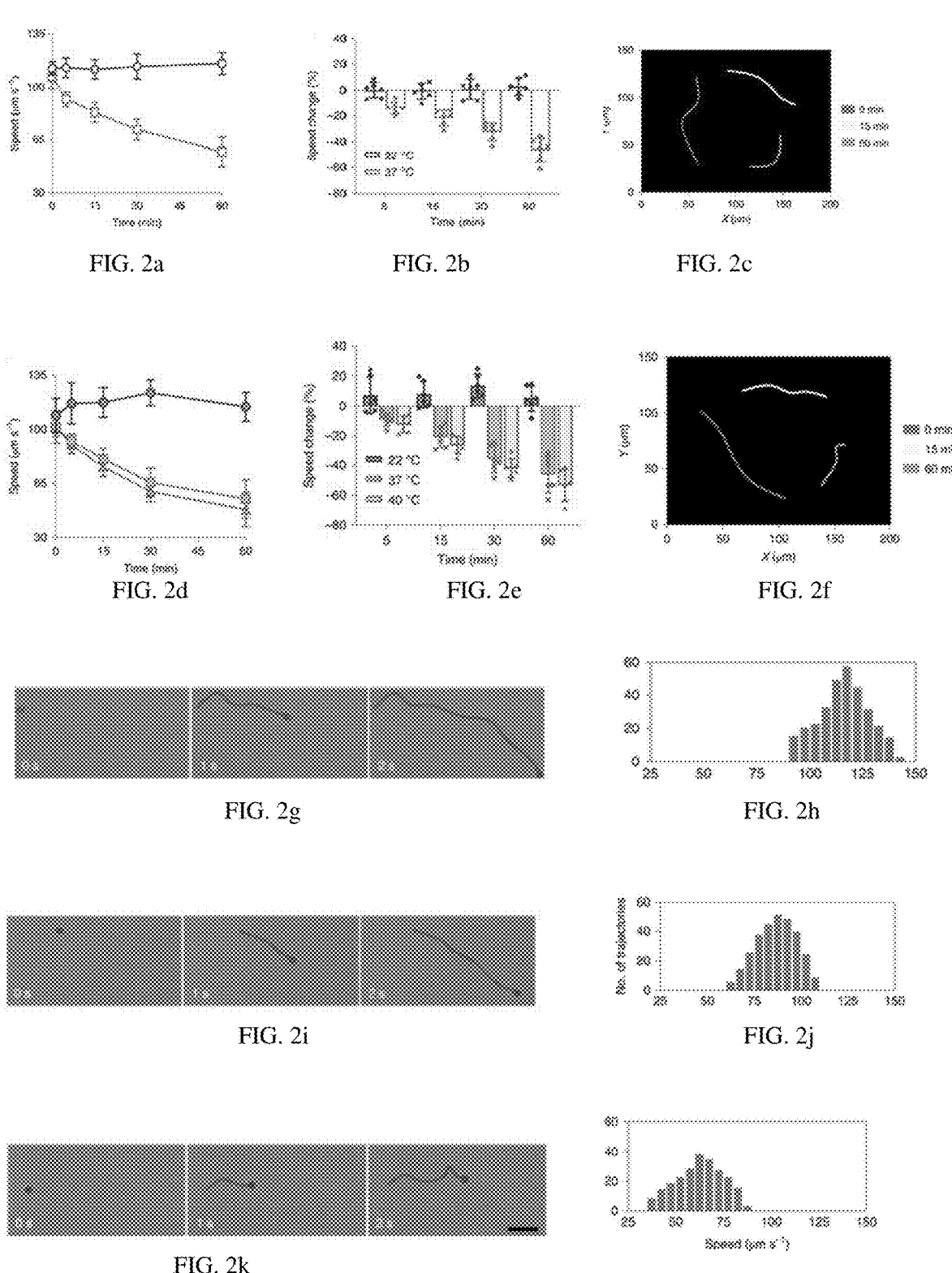
FIGS. 2a-2l show motion behavior of algae-NP-robot.

Motion behavior of algae-NP-robot. The binding stability and motion behavior of the resulting algae-NP-robot were investigated in their optimal growth conditions (TAP medium at 22° C.) and were compared to those of the bare algae. The speed of algae-NP-robot (104.6±11.2 μm s$^{-1}$) was similar to that of the bare algae (115.5±11.8 μm s$^{-1}$), suggesting that coupling of NP to the algae had a negligible effect on the algae motility. As we sought to leverage the in vivo propulsion of algae-NP-robot for deep lung delivery, their propulsion characteristics in a simulated lung fluid (SLF)[31] were first evaluated. The motion behavior of bare algae at room temperature (RT, 22° C.) and at body temperature (BT, 37° C.) was compared in SLF (FIGS. 2a-c). The bare algae maintained a steady speed of ~115 m s$^{-1}$ (11.5 body lengths per second) over 1 h at RT but displayed a gradual decrease in speed from ~101 to ~55 m s$^{-1}$ at BT, indicating that higher temperatures could impact algal motion[32]. The growth rate of bare algae was monitored at both temperatures, and an inhibition of growth was observed at BT[33]. Algae-NP-robot demonstrated similar trends in their motion (FIGS. 2d-2f). To mimic the elevated BT of patients with VAP, an additional test was carried out at 40° C., and no significant differences were observed compared with algae-NP-robot at BT. FIGS. 2g-2l show the representative tracking trajectories of individual algae-NP-robot over 0, 1 and 2 s intervals and the corresponding mean speed distribution in SLF at different operation times at BT. It is important to note that 95% of the algae remained viable after 1 h of motion in SLF, reflecting the good adaptivity of algae under these conditions. At longer timepoints of 12 and 24 h, approximately 85% and 60% of the algae-NP-robot, respectively, remained motile when exposed to SLF in the dark at BT; this percentage further decreased to less than 20% after 48 h of exposure. Algae-NP-robot did not exert cytotoxicity when incubated with different cell types, and their capacity for phototaxis was unaffected. Overall, these results demonstrate that modification with NPs has a negligible effect on the intrinsic motion behaviour of algae, allowing algae-NP-robot to be employed as an active delivery platform in physiological conditions.

In vivo distribution, retention and clearance in the lungs. The lung distribution of algae-NP-robot was examined after intratracheal administration[34]. Leveraging autofluorescence from the algae's chloroplasts, the distribution was visualized by ex vivo fluorescence imaging of the excised lungs at various timepoints (FIG. 3a). Fluorescence from the algae-NP-robot permeated throughout the lung tissue within 1 h, and the strong signal was retained for at least 24 h. In contrast, NP-modified deflagellated algae (denoted as 'static algae-NP'), incapable of moving, were characterized by SEM and used as a control. The signal of static algae-NP sharply decreased within 4 h and nearly disappeared after 12 h, highlighting the role of active motion in promoting robust lung distribution and retention. To quantitatively compare algal retention, we homogenized the lungs and measured the fluorescence intensity. The total fluorescence of the algae-NP-robot slowly decreased over the course of 72 h and was significantly higher than that of the static algae-NP up to 48 h. After 72 h, the fluorescence intensity returned to near the baseline for both groups. The normalized fluorescence data further verified the slower clearance of algae-NP-robot, as 86% and 65% of the original signal were present at 4 and 24 h, respectively (FIG. 3b). In comparison, static algae-NP exhibited greatly reduced signals, with 24% and 8% remaining at 4 and 12 h, respectively. Overall, these data indicate that the motion behavior of algae-NP-robot greatly improved their lung retention.

To better understand the greatly reduced clearance of algae-NP-robot compared with static algae-NP, we sought to elucidate the potential role of macrophages, an abundant cell population in the lung alveoli capable of clearing exogenous species by phagocytosis[35]. Algae-NP-robot and static algae-NP were mixed with murine J774 macrophages at a 1:1 ratio and incubated at 37° C. in the dark. FIG. 3c displays the different stages of the algae-NP-robot phagocytosis by macrophages. Algae-NP-robot showed strong autofluorescence from the algae before binding and on contacting the macrophage (0 min). After being taken up by the macrophages via phagocytosis, the algae-NP-robot was gradually degraded, as indicated by a progressive decrease in autofluorescence (15-75 min). By counting the numbers of unbound algae-NP-robot and macrophages at different timepoints, the uptake of algae-NP-robot over time was quantified. As shown in FIG. 3d, static algae-NP were internalized significantly faster than their active counterparts, indicating that active motion facilitates escape from macrophage uptake. A cryo-treated algae-NP-robot, incapable of moving, was also taken up faster by macrophages compared with algae-NP-robot, confirming that the physical presence of flagella is not a major factor in the inhibition of phagocytosis. Quantification of the total fluorescence intensity showed that the signal of the algae-NP-robot was consistently higher than that of the static control during 72 h of incubation. Compared with the uptake profiles (FIG. 3d), the relative fluorescence profiles of the algae were reversed (FIG. 3e). It should be noted that the optical absorbance and fluorescence of the algae-NP-robot without the macrophages was constant, further supporting that macrophage phagocytosis was an important reason for the observed lung-clearance kinetics.

Figure 3G:
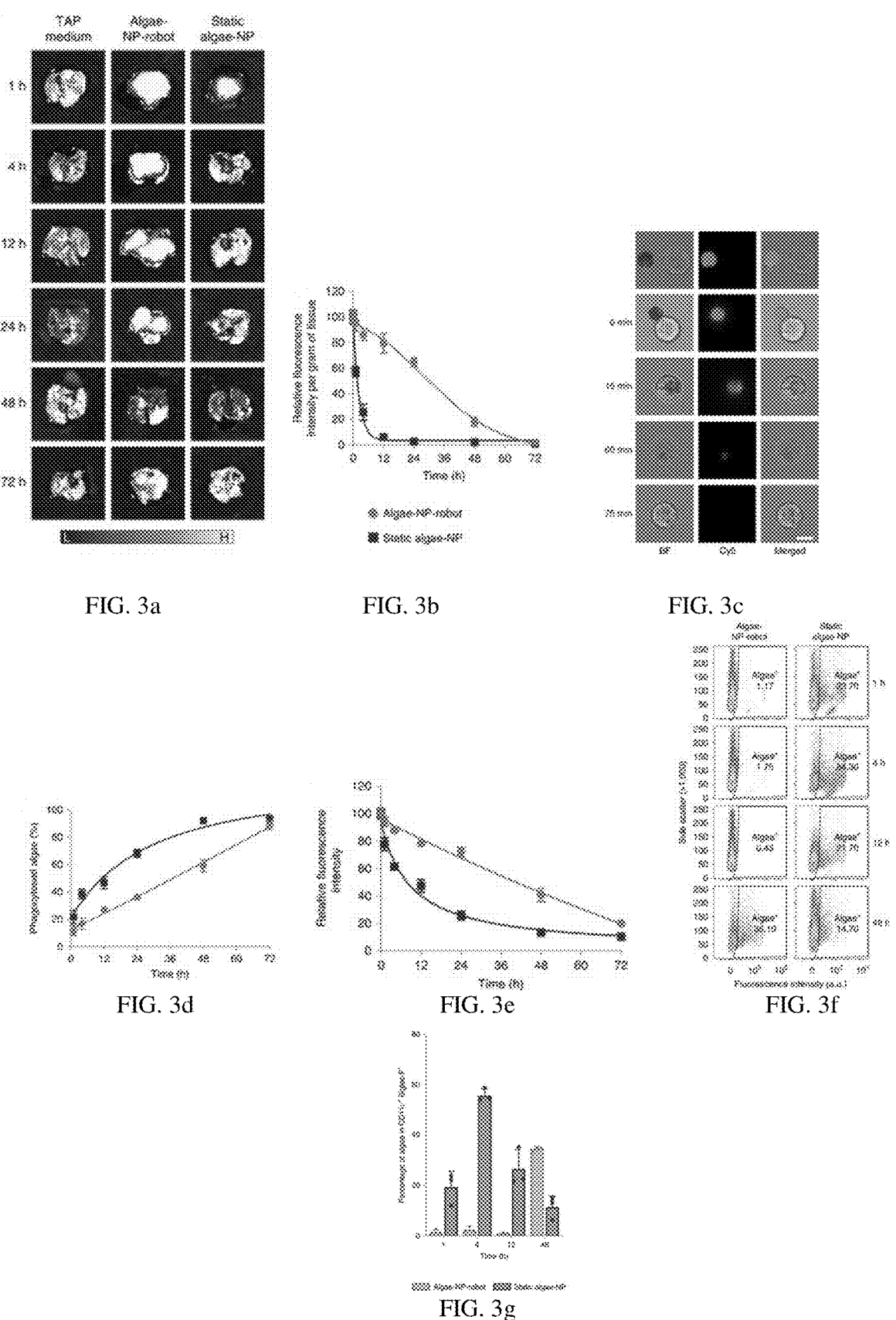

To better understand the clearance mechanism in vivo, flow cytometry analysis of the macrophage uptake was performed at different timepoints after intratracheal administration in mice (FIGS. 3f, 3g). A minimal uptake of algae-NP-robot by alveolar macrophages was observed within the first 12 h, and a large increase of uptake was observed at 48 h. In comparison, approximately 20% of the macrophages were positive for static algae-NP uptake after only 1 h, with the uptake peaking at 4 h post-administration before decreasing at later timepoints. The decreased signal is attributed to the degradation of algae after uptake, which destroys their autofluorescence (FIG. 3c). These results indicate that alveolar macrophage uptake is a major clearance mechanism for algae in the lungs. The delayed in vivo uptake of the algae-NP-robot by alveolar macrophages corroborates the in vitro findings and could explain the enhanced lung retention that was observed.

Drug loading and in vivo antibacterial efficacy. Based upon the uniform lung distribution and prolonged retention, it was postulated that the algae-NP-robot may serve as an effective drug carrier for treating infection in the lower respiratory tract. In the study, ciprofloxacin (Cip), a common antibiotic drug for *P. aeruginosa*, was encapsulated into NP (denoted 'NP(Cip)'). The drug loading was optimized to meet the therapeutic threshold for *P. aeruginosa*[36].

Figure 4D:
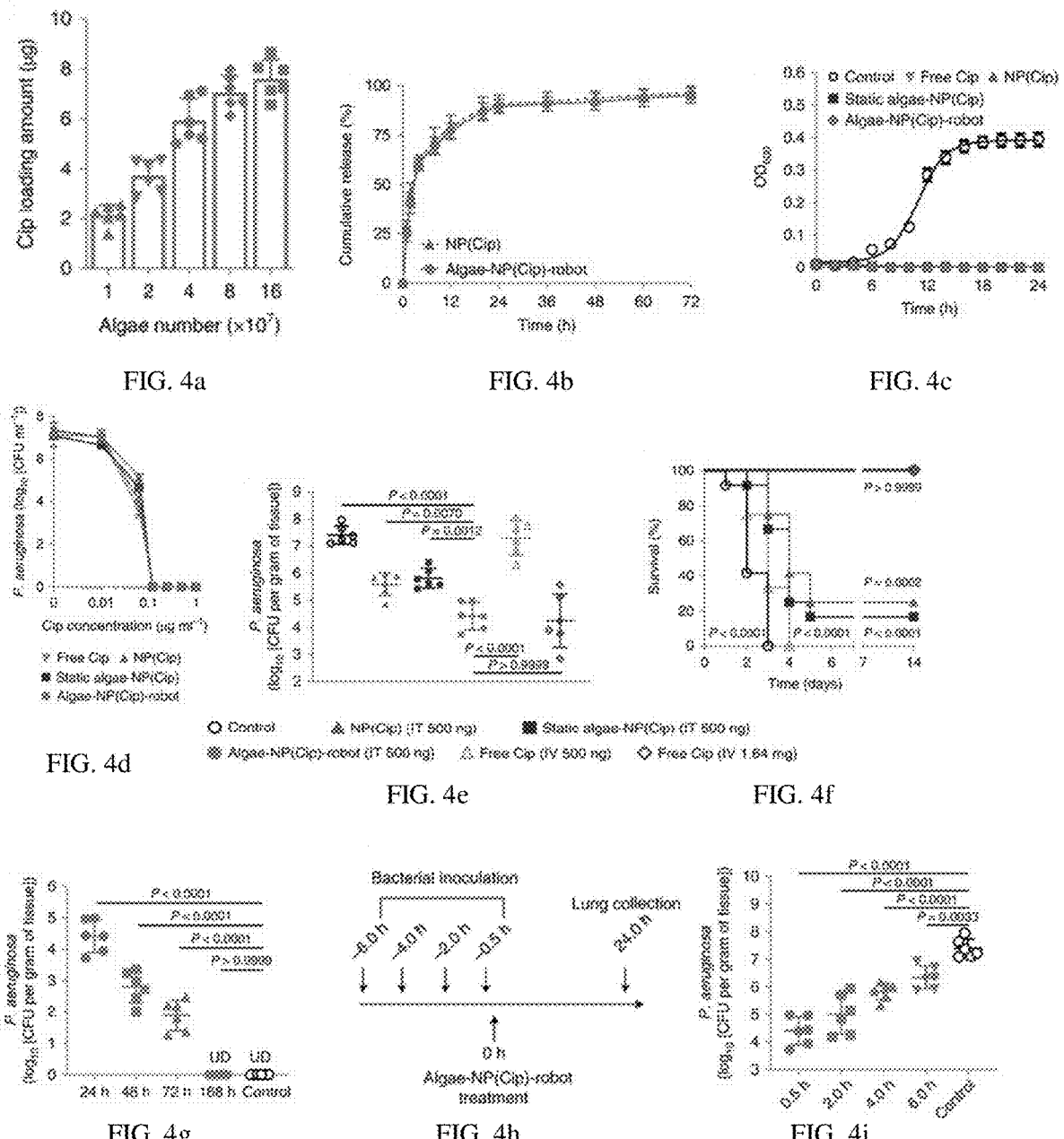

The same fabrication method was used to conjugate drug-loaded NP to the algae surface (denoted 'algae-NP (Cip)-robot'). We then evaluated the Cip loading yield onto the algae (FIG. 4a). Using a constant drug initial input, the total amount of drug loaded increased linearly with the algae number up to approximately $4 \times 10^7$ algae and then slowly saturated. The formulation of 6 µg Cip on $4 \times 10^7$ algae was thus selected for subsequent in vitro and in vivo efficacy studies. Similar to NP(Cip), the algae-NP(Cip)-robot demonstrated an initial burst release over the initial 20 h, followed by a slow release up to 96% by 72 h (FIG. 4b). The minimal inhibitory concentration (MIC) against *P. aeruginosa* was evaluated. Bacterial growth was inhibited at a Cip concentration of 62.5 ng ml$^{-1}$ for all the groups (FIG. 4c), consistent with what has been previously reported[37]. FIG. 4d shows the enumerated bacterial colony-forming units (CFU) after treatment with algae-NP(Cip)-robot and with other controls, enabling us to establish the minimal bactericidal concentration. Algae-NP(Cip)-robot had a comparable inhibitory efficacy to free Cip, and the minimal bactericidal concentration of both was determined to be 125 ng ml$^{-1}$. Bare algae and NPs had negligible effects on the bacteria, supporting the fact that the inhibitory efficacy of algae-NP (Cip)-robot was solely due to the loaded Cip. An in vitro study was also performed to confirm that the algae-NP-robot is able to bind to *P. aeruginosa*. After 24 h of incubation, a signal from the Hoechst 33342-stained DNA of the bacteria co-localized with that of the DiI-labelled NPs, demonstrating effective binding between the two. The binding efficiency was further quantified by the enumeration of unbound bacteria, revealing that 95% of the initial bacterial input was bound to algae-NP-robot. Such binding is thought to be mediated by protein receptors present on the surface of the NPs[38]. To further verify the unique binding properties of the NPs, PLGA NP cores without membrane coating and liposomes were used, and neither control bound effectively to the bacteria.

Next, the ability of algae-NP(Cip)-robot to treat acute lung infection in vivo was examined. *P. aeruginosa* was first inoculated to characterize the bacterial dispersion within the lungs. The data demonstrated that the bacteria disseminated throughout the entirety of the lungs within 1 h after intratracheal inoculation, suggesting that algae-NP-robot could be used to efficiently treat conditions like VAP. To investigate the antibacterial efficacy against *P. aeruginosa* pneumonia, algae-NP(Cip)-robot or control samples were intratracheally administered 30 min after bacterial inoculation. An antibiotic dose of 500 ng Cip was administered per mouse. The lungs were then collected, followed by homogenization for bacterial enumeration 24 h after administration. As illustrated in FIG. 4e, the bacterial burden after the algae-NP(Cip)-robot treatment was quantified as $2.6 \times 10^4$ CFU g$^{-1}$, representing a three orders of magnitude reduction compared with the negative control ($2.6 \times 10^7$ CFU g$^{-1}$), and a significant reduction compared with static algae-NP(Cip) ($6.5 \times 10^1$ CFU g$^{-1}$) and NP(Cip) ($3.8 \times 10^1$ CFU g$^{-1}$). A survival study was conducted using the same experimental setup (FIG. 4f). The algae-NP(Cip)-robot treatment of infected mice resulted in 100% survival over the entire duration of the 14-day study (P<0.0001, n=12). In stark contrast, all the untreated mice died within three days. The survival rates of mice treated with NP(Cip) or static algae-NP(Cip) were 25.0% and 16.7%, respectively. It was concluded that the prolonged lung retention and sustained release characteristics of algae-NP(Cip)-robot enabled the significant improvement in survival compared with the control groups. Subsequently, the efficacy of algae-NP(Cip)-robot was compared with the conventional treatment of intravenous (IV) Cip. The algae-NP(Cip)-robot treatment significantly outperformed IV Cip at the same drug dosage (500 ng per mouse) and achieved similar efficacy compared with IV Cip at a more clinically relevant dosage (1.644 mg per mouse). Additional experiments were performed to quantify the lung bacterial burden at later timepoints following algae-NP(Cip)-robot treatment, revealing a progressive decrease over time and complete clearance after one week (FIG. 4g). To verify the effectiveness of algae-NP (Cip)-robot with delayed treatment, we performed an additional study in which mice were treated at progressively longer intervals after a lethal *P. aeruginosa* challenge (FIGS. 4h, 4i). Although the therapeutic efficacy decreased as the treatment interval increased, a significant reduction was still observed even with a 6 h delay.

Figures 5A, 5B, 5C, 5D, 5E, 5F, 5G, 5H, 5I:
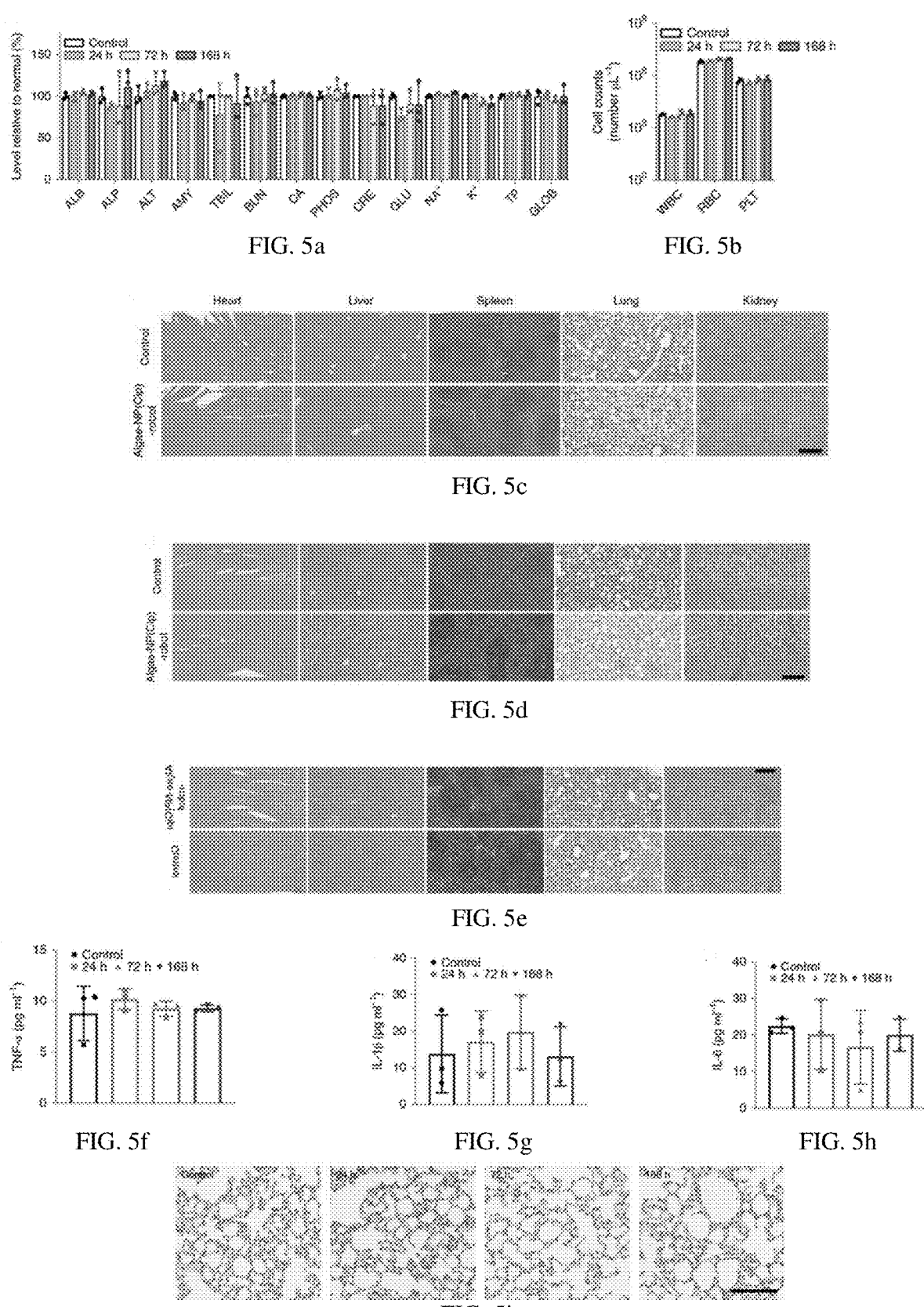
FIGS. 5a-5i show in vivo safety evaluation of algae-NP(Cip)-robot.

Biosafety evaluation. Last, to verify the biosafety of algae-NP(Cip)-robot, a comprehensive analysis of blood chemistry and major blood cell populations was conducted 24, 72 and 168 h after administration into the lungs (FIGS. 5a, 5b). Compared with mice administered only with the TAP medium, little difference was observed for all the blood parameters. The heart, liver, spleen, lungs and kidneys were also processed by haematoxylin and eosin staining (FIGS. 5c-5e). The overall structural integrity of all the tissues was nearly identical to those from mice administered with the TAP medium, demonstrating no signs of acute toxicity and further supporting the safety of algae-NP(Cip)-robot. To further evaluate for potential inflammatory responses in the lungs, different cytokines (tumour necrosis factor alpha (TNF-$\alpha$), interleukin (IL)-13 and IL-6) were analysed 24, 72 and 168 h after the intratracheal administration of algae-NP (Cip)-robot into the lungs. No significant difference in cytokine levels was observed for the algae-NP(Cip)-robot treatment compared with the control group (FIGS. 5f-5h). Histological sections of lung tissues collected over time at 24, 72 and 168 h after administration revealed negligible leucocyte infiltration, normal structures of the lung tissue and no signs of inflammation (FIG. 5i). Further in vitro studies verified that algae-NP-robot, in contrast to bacterial flagellin[39], did not trigger the significant production of proinflammatory cytokines by innate immune cells. Together, these data suggest the favourable safety profile of the algae-NP-robot delivery platform.

Conclusions. The biohybrid microrobot platform described in this work creates new opportunities for active drug delivery to the lungs of ventilated ICU patients. This is due to its distinct advantages in terms of facile large-scale production, autonomous motion and long lifespan in localized environments, intrinsic autofluorescence for easy in vivo observation and potential targeting functionality.

The invention contemplates that different delivery methods, such as by inhalation or IV administration, or leveraging the inherent phototaxis properties of algae, may expand the scope of the platform across a wider range of applications. Although the treatment of acute pneumonia using algae-NP-robot probably benefited from uniform dispersion throughout the lungs, biohybrid microrobots can also be integrated with sensory and targeting functionalities for situations in which more precise delivery is required. For example, optogenetics technology that locally induces the light emission of target cells with photoreceptors[40] can be introduced to trigger the inherent phototaxis of algae[41], thus enabling site-specific targeting[42]. The algae can also be genetically engineered with functional proteins on their surface to introduce additional functionalities[43]. Besides algae, other microorganisms with specific sensory or targeting capabilities[13-44] could also be used in the development of autonomous drug delivery vehicles for treating pulmonary diseases.

Methods

Algae CULTURE. Green *C. reinhardtii* algae (strain CC-125 wild-type mt+) were obtained from the *Chlamydomonas* Resource Center. The algae were transferred from the agar plate to Tris-acetate-phosphate (TAP) medium (Thermo Fisher Scientific) and cultivated at room temperature under cycles of 12 h sunlight and 12 h dark.

Neutrophil cell culture. Human neutrophil-like cells (HL-60, American Type Culture Collection, ATCC CCL-240) were cultured in RPMI 1640 medium (11875135, Gibco) supplemented with 10 v/v % fetal bovine serum (SH30541.03, Hyclone) and 1 v/v % penicillin-streptomycin (15140122, Gibco). Cells were maintained at 37° C. in a humidified incubator with 5% $CO_2$ and regularly tested for *mycoplasma* contamination.

Neutrophil cell membrane derivation. Plasma membrane of HL-60 cells was harvested following a previously published protocol[31]. Briefly, frozen cells were thawed and washed with 1×PBS three times by centrifugation at 800 g. Cells were then suspended in a hypotonic lysing buffer containing 30 mM Tris-HCl (pH=7.5), 75 mM sucrose, 225 mM D-mannitol, 0.2 mM ethylene glycol-bis(β-aminoethyl ether)-(N,N,N',N'-tetraacetic acid (EGTA), and protease and phosphatase inhibitor cocktails (Sigma Aldrich). Cells were then subjected to 20 passes using a Kinematica Polytron PT 10/35 probe homogenizer. The cell suspension was centrifuged (800 g, 5 min, 4° C.) and the pellet was suspended in the hypotonic lysing buffer and homogenized again with 20 passes. The solution was combined with supernatant from the first homogenate and centrifuged at 20,000 g for 25 min at 4° C. The supernatant was then centrifuged at 100,000 g for 35 min at 4° C. The supernatant was discarded and the pellet was washed twice with 0.2 mM ethylenediaminetetraacetic acid (EDTA, 46-034-CI, Corning) in water. Membrane content was quantified by using a BCA kit (Pierce) in comparison with bovine serum albumin (BSA) protein standards. The purified membrane was suspended with 0.2 mM EDTA at a protein concentration of 10 mg ml$^{-1}$ and stored at −80° C. for subsequent studies.

Synthesis of polymeric cores. Drug loaded polymeric cores were synthetized following a reported method with slight modifications[30]. Briefly, 50 µl of 25 mg ml$^{-1}$ ciprofloxacin (HCl salt, Sigma Aldrich) solution was emulsified in 500 µl chloroform solution containing 50 mg ml$^{-1}$ poly (lactic-co-glycolic acid) (50:50 PLGA, 0.67 dl g$^{-1}$, Lactel Absorbable Polymers) using an ultrasonic probe sonicator (Fisher Scientific) operating at a power of 10 W. The sonication lasted for 2 min with alternating cycles of 2 s power on and 2 s power off inside an ice bath. Then the emulsion was transferred to 10 ml of aqueous solution and sonicated for another 2 min. The emulsion was stirred for 4 h to completely evaporate the chloroform. All the samples were centrifuged at 16,100 g for 5 min, washed twice with ultrapure water, and lyophilized for future use. The 3,3'-dioctadecyloxacarbocyanine perchlorate (DiO, $\lambda_{ex}/\lambda_{em}$=484 nm/501 nm; ThermoFisher Scientific)-loaded nanoparticles were synthesized by replacing ciprofloxacin with 1 mg ml$^{-1}$ of the dye and then following the same method.

Synthesis of neutrophil membrane-coated nanoparticles. Neutrophil membrane-coated nanoparticles were synthesized by a membrane cloaking technique[31]. Briefly, the neutrophil membrane was mixed with PLGA cores with a 1:1 polymer to membrane protein weight ratio. The mixture was sonicated in a bath sonicator (Fisher Scientific FS30D) for 3 min. The resulting membrane-coated nanoparticles were separated from the solution by 5 min centrifugation at 16,100 g and washed twice with ultrapure water.

Characterization of neutrophil membrane-coated nanoparticles. Neutrophil membrane-coated nanoparticles were measured for hydrodynamic size and surface zeta potential by dynamic light scattering (ZEN 3600 Zetasizer, Malvern). To examine the morphology, nanoparticles were stained with uranyl acetate (0.2 wt %) and visualized using transmission electron spectroscopy (FEI 200 kV Sphera). Bright-field and fluorescent images of 1,1'-dioctadecyl-3,3,3',3'-tetramethylindodicarbocyanine, 4-chlorobenzenesulfonate salt (DiD, $\lambda_{ex}/\lambda_{em}$=644 nm/665 nm; ThermoFisher Scientific)-labeled neutrophil membrane and DiO-loaded PLGA core were taken on a fluorescence microscopy (EVOS FL).

Preparation of algae-NP-robot. Green algae were washed three times with ultrapure water to remove TAP buffer and then resuspended in ultrapure water. Then, 1×10$^7$ algae were treated with 20 µM azido-PEG$_4$-NHS ester (Click Chemistry Tools) for 45 min at room temperature. To examine the effective binding of azido groups on the algae surface, the resulting algae were incubated with BDP FL DBCO (Lumiprobe) for 30 min and then subjected to flow cytometry analysis (1×10$^4$ events were collected for analysis). Then neutrophil membrane-coated PLGA nanoparticles (denoted 'NP') were modified with N3 bonds for the click chemistry. Here, NP were incubated with 40 µM DBCO-PEG$_4$-NHS ester for 1 h at room temperature. The presence of triple bonds on the NP surface was confirmed by adding FAM azide, 5-isomer (Lumiprobe) and visualized by fluorescence microscopy. Both of the resulting algae and NP were washed five times with ultrapure water, removing unreacted NHS ester for the following conjugation. To optimize the binding efficiency, we used different concentrations of NP at 0.04 mg ml$^{-1}$, 0.2 mg ml$^{-1}$, and 1 mg ml$^{-1}$ for conjugation. During the conjugation, DBCO-modified NP were incubated with azido-functionalized algae for 45 min. After 3 min centrifugation at 300 g and three washes with TAP medium, the resulting algae-NP-robot were collected for further characterization.

Characterization of algae-NP-robot. To perform scanning electron microscopy (SEM) characterization, algae-NP-robots were first fixed with 2.5% glutaraldehyde overnight at 4° C. and washed three times with ultrapure water. After overnight drying, algae-NP-robots were coated with palladium for SEM characterization using an acceleration voltage of 3 KV (Zeiss Sigma 500 SEM instrument). The bare algae and static algae-NP were treated and examined using the same methodology. The attachment of NP to algae was captured by fluorescence microscopy (EVOS FL) with three individual fluorescence channels, Cy5, RFP and GFP, which corresponded to the autofluorescence of algae, the DiD-labeled neutrophil membrane, and the DiO-loaded PLGA cores, respectively.

Algae viability study. To evaluate algae viability, algae were stained with 5 µM SYTOX green fluorescent probe (Thermo Fisher). After 10 min incubation at room temperature in the dark, the bright green fluorescence of dead algae was examined by fluorescence microscopy. Based on previously reported methods[29], the solution was measured for SYTOX fluorescence intensity ($\lambda_{ex}/\lambda_{em}$=504 nm/523 nm) using a plate reader. No washing steps were required due to the specific staining of the nucleic acid of dead algae.

Motion analysis. The motion of algae-NP-robot and bare algae control was evaluated in simulated lung fluid (SLF). The composition of SLF was shown in Supplementary Table 1. The movies of the motion were captured by an inverted optical microscope (Nikon Eclipse Instrument Inc. Ti-S/L 100) coupled with different microscope objectives (4×, 10×, and 20×), a Hamamatsu digital camera C11440, and NIS Elements AR 3.2 software. An NIS Element tracking module was used to measure the corresponding algae speed in SLF.

Ex vivo lung imaging and retention quantification. All animal experiments were performed in accordance with National Institutes of Health (NIH) guidelines and approved by the Institutional Animal Care and Use Committee of the University of California San Diego. Male CD-1 mice (Charles River Labs) were placed under anesthesia with a cocktail of ketamine (Pfizer) at 100 mg/kg and xylazine (Lloyd Laboratories) at 20 mg kg$^{-1}$. They were subsequently intratracheally administrated with TAP buffer, 5×10$^6$ algae-NP-robot, or 5×10$^6$ static algae-NP. After certain timepoints (1, 4, 12, 24, 48, and 72 h), the mice were euthanized, and their lungs were excised for analysis. Ex vivo fluorescence images of the lungs were obtained using a Xenogen IVIS 200 system. The lung samples were subsequently homogenized and fluorescence values were quantified using a BioTek Synergy Mx microplate reader.

In vitro macrophage phagocytosis. J774A.1 macrophage cells (ATCC) were first cultured in Dulbecco's modified Eagle medium (Invitrogen). The cells were seeded at 1×10$^6$ cells/well in a 24-well plate. Algae-NP-robots were then added at a robot/macrophage ratio of 1:1 and incubated at 37° C. After certain timepoints (1, 4, 12, 24, 48, and 72 h), the mixture was analyzed by fluorescence microscopy and fluorescence values were quantified using a BioTek Synergy Mx microplate reader. The static algae-NP control was tested and quantified following the same method.

Ciprofloxacin (Cip) loading and release measurement. A total of 1 ml of algae at different concentrations (1×10$^7$ ml$^{-1}$, 2×10$^7$ ml$^{-1}$, 4×10$^7$ ml$^{-1}$, 8×10$^7$ ml$^{-1}$, and 16×10$^7$ ml$^{-1}$) was conjugated with 1 mg NP(Cip) by click chemistry, followed by removal of free NP(Cip) by three washes at 300 g for 2 min. Then, the algae-NP(Cip)-robots were suspended in 1 ml of TAP for further use. After fabrication of algae-NP (Cip)-robot, the solution was measured for Cip fluorescence intensity ($\lambda_{ex}/\lambda_{em}$=270 nm/440 nm). A standard calibration curve was made by measuring serial dilutions of Cip solution (0-10 µg ml$^{-1}$), and the Cip concentration was determined by comparing with the standard calibration curve. The Cip release was conducted with 1 ml of algae-NP(Cip)-robot at 37° C. within 72 h. Cip concentration was determined also by fluorescence measurement.

In vitro antibacterial activity of algae-NP(Cip)-robot. A volume of 1 ml of P. aeruginosa 01 strain (ATCC) at 5×10$^6$ CFU (colony-forming unit) ml$^{-1}$ was mixed with TAP, free Cip, NP(Cip), static algae-NP(Cip), or algae-NP(Cip)-robot at an equivalent Cip amount. To obtain the minimal inhibitory concentration (MIC) of Cip, various concentrations of Cip (31.25 ng ml$^{-1}$, 62.5 ng ml$^{-1}$, 125 ng ml$^{-1}$, 250 ng ml$^{-1}$, 500 ng ml$^{-1}$, and 1 µg ml$^{-1}$) were used. The bacterial growth was quantified by measuring their absorbance at 600 nm (OD$_{600}$).

In vivo enumeration study. P. aeruginosa was first streaked onto a Luria broth (LB; Sigma-Aldrich) agar plate and cultured overnight at 37° C. A single colony was transferred into 50 ml of liquid LB for 10 h at 37° C. with shaking. The bacteria were collected after spinning down at 5,000 g for 20 min, washing with PBS, and resuspending in PBS to a final concentration of 2×10$^8$ CFU ml$^{-1}$. Male CD-1 mice (Charles River Labs) were placed under anesthesia with a cocktail of ketamine (Pfizer) at 100 mg kg$^{-1}$ and xylazine (Lloyd Laboratories) at 20 mg kg$^{-1}$. They were intratracheally inoculated with 5×10$^6$ CFU of P. aeruginosa and subsequently intratracheally administered with TAP buffer, free Cip, NP(Cip), 5×10$^6$ algae-NP(Cip)-robot, or 5×10$^6$ static algae-NP(Cip) at an equivalent Cip amount (500 ng). After 24 h, the mice were euthanized, and their lungs were collected. The lungs were homogenized using a Biospec Mini Beadbeater, serially diluted in PBS, and plated onto agar plates with a spotting volume of 50 µl. After 24 h of culture, bacterial colonies were counted to determine the bacterial load in each lung.

In vivo survival study. Male CD-1 mice were placed under anesthesia with a cocktail of ketamine at 100 mg kg$^{-1}$ and xylazine at 20 mg kg$^{-1}$. They were intratracheally inoculated with 5×10$^6$ CFU of P. aeruginosa and then intratracheally administered with TAP buffer, free Cip, NP-Cip, 5×10$^6$ algae-NP(Cip)-robot, or 5×10$^6$ static algae-NP (Cip) at an equivalent Cip amount (500 ng). Survival of each mouse was monitored on a daily basis.

In vivo safety studies. Mice were euthanized at 24 h after intratracheal administration of TAP buffer or 5×10$^6$ algae-NP(Cip)-robot for sample collection. For the comprehensive metabolic panel, aliquots of blood were allowed to coagulate, and the serum was collected by centrifugation. To obtain blood cell counts, whole blood was collected into potassium-EDTA collection tubes (Sarstedt). Lab tests were performed by the UC San Diego Animal Care Program Diagnostic Services Laboratory. To perform the histological analysis, the major organs were sectioned and stained with H&E (Leica Biosystems), followed by imaging using a Hamamatsu Nanozoomer 2.0-HT slide scanning system.

25

REFERENCES

1. Li, J. et al. Micro/nanorobots for biomedicine: delivery, surgery, sensing, and detoxification. *Sci. Robot.* 2, eaam6431 (2017).
2. Gao, C. et al. Biomedical micro-/nanomotors: from overcoming biological barriers to in vivo imaging. *Adv. Mater.* 33, 2000512 (2020).
3. Wu, Z., Chen, Y., Mukasa, D., Pak, O. S. & Gao, W. Medical micro/nanorobots in complex media. *Chem. Soc. Rev.* 49, 8088-8112 (2020).
4. Esteban-Fernández de Ávila, B. et al. Micromotor-enabled active drug delivery for in vivo treatment of stomach infection. *Nat. Commun.* 8, 272 (2017).
5. Wu, Z. et al. A microrobotic system guided by photoacoustic computed tomography for targeted navigation in intestines in vivo. *Sci. Robot.* 4, eaax0613 (2019).
6. Wu, Z. et al. A swarm of slippery micropropellers penetrates the vitreous body of the eye. *Sci. Adv.* 4, eaat4388 (2018).
7. Gao, W. et al. Artificial micromotors in the mouse's stomach: a step toward in vivo use of synthetic motors. *ACS Nano* 9, 117-123 (2015).
8. Wei, X. et al. Biomimetic micromotor enables active delivery of antigens for oral vaccination. Nano Lett. 19, 1914-1921 (2019).
9. Servant, A., Qiu, F., Mazza, M., Kostarelos, K. & Nelson, B. J. Controlled in vivo swimming of a swarm of bacteria-like microrobotic flagella. Adv. Mater. 27, 2981 (2015).
10. Yan, X. et al. Multifunctional biohybrid magnetite microrobots for imaging-guided therapy. Sci. Robot. 2, eaaq1155 (2017).
11. Sun, L. et al. Biohybrid robotics with living cell actuation. Chem. Soc. Rev. 49, 4043-4069 (2020).
12. Ricotti, L. et al. Biohybrid actuators for robotics: a review of devices actuated by living cells. Sci. Robot. 2, eaaq0459 (2017).
13. Felfoul, O. et al. Magneto-aerotactic bacteria deliver drug-containing nanoliposomes to tumour hypoxic regions. Nat. Nanotechnol. 11, 941-947 (2016).
14. Medina-Sánchez, M., Schwarz, L., Meyer, A. K., Hebenstreit, F. & Schmidt, O. G. Cellular cargo delivery: toward assisted fertilization by sperm carrying micromotors. Nano Lett. 16, 555-561 (2015).
15. Weibel, D. B. et al. Microoxen: microorganisms to move microscale loads. Proc. Natl Acad. Sci. USA 102, 11963-11967 (2005).
16. Yasa, O., Erkoc, P., Alapan, Y. & Sitti, M. Microalga-powered microswimmers toward active cargo delivery. Adv. Mater. 30, 1804130 (2018).
17. Silflow, C. D. & Lefebvre, P. A. Assembly and motility of eukaryotic cilia and flagella. Lessons from *Chlamydomonas reinhardtii*. Plant Physiol. 127, 1500-1507 (2001).
18. Zhang, Q. et al. Neutrophil membrane-coated nanoparticles inhibit synovial inflammation and alleviate joint damage in inflammatory arthritis. Nat. Nanotechnol. 13, 1182-1190 (2018).
19. Metersky, M. L. & Kalil, A. C. Management of ventilator-associated pneumonia: guidelines. Clin. Chest Med. 39, 797-808 (2018).
20. Schreiber, M. P. & Shorr, A. F. Challenges and opportunities in the treatment of ventilator-associated pneumonia. Expert Rev. Anti Infec. Ther. 15, 23-32 (2017).

21. Muscedere, J. et al. The clinical impact and preventability of ventilator-associated conditions in critically ill patients who are mechanically ventilated. Chest 144, 1453-1460 (2013).
22. Melsen, W. G. et al. Attributable mortality of ventilator-associated pneumonia: a meta-analysis of individual patient data from randomized prevention studies. Lancet Infect. Dis. 13, 665-671 (2013).
23. Kharel, S., Bist, A. & Mishra, S. K. Ventilator-associated pneumonia among ICU patients in WHO Southeast Asian region: a systematic review. PLoS ONE 16, e0247832 (2021).
24. Vincent, J.-L., de Souza Barros, D. & Cianferoni, S. Diagnosis, management and prevention of ventilator-associated pneumonia. Drugs 70, 1927-1944 (2010).
25. Kerschgens, I. P. & Gademann, K. Antibiotic algae by chemical surface engineering. ChemBioChem 19, 439-443 (2018).
26. Szponarski, M. et al. On-cell catalysis by surface engineering of live cells with an artificial metalloenzyme. Commun. Chem. 1, 84 (2018).
27. Shi, P. et al. Spatiotemporal control of cell-cell reversible interactions using molecular engineering. Nat. Commun. 7, 13088 (2016).
28. Wang, H. et al. Metabolic labeling and targeted modulation of dendritic cells. Nat. Mater. 19, 1244-1252 (2020).
29. Hu, Q. et al. Conjugation of haematopoietic stem cells and platelets decorated with anti-PD-1 antibodies augments anti-leukaemia efficacy. Nat. Biomed. Eng. 2, 831-840 (2018).
30. Fang, R. H. et al. Cell membrane coating nanotechnology. Adv. Mater. 30, 1706759 (2018).
31. Kumar, A. et al. A biocompatible synthetic lung fluid based on human respiratory tract lining fluid composition. Pharm. Res. 34, 2454-2465 (2017).
32. Tanaka, Y. et al. Acclimation of the photosynthetic machinery to high temperature in *Chlamydomonas reinhardtii* requires synthesis de novo of proteins encoded by the nuclear and chloroplast genomes. Plant Physiol. 124, 441-449 (2000).
33. Singh, S. P. & Singh, P. Effect of temperature and light on the growth of algae species: a review. Renew. Sust. Energ. Rev. 50, 431-444 (2015).
34. Ortiz-Munoz, G. & Looney, M. R. Non-invasive intra-tracheal instillation in mice. Bio-protocol 5, e1504 (2015).
35. Sibille, Y. & Reynolds, H. Y. Macrophages and polymorphonuclear neutrophils in lung defense and injury. Am. Rev. Respir. Dis. 141, 471-501 (1990).
36. Justo, J. A., Danziger, L. H. & Gotfried, M. H. Efficacy of inhaled ciprofloxacin in the management of non-cystic fibrosis bronchiectasis. Ther. Adv. Respir. Dis. 7, 272-287 (2013).
37. Oliver, A. et al. Hypermutation and the preexistence of antibiotic-resistant *Pseudomonas aeruginosa* mutants: implications for susceptibility testing and treatment of chronic infections. Antimicrob. Agents Chemother. 48, 4226-4233 (2004).
38. Lovewell, R. R., Patankar, Y. R. & Berwin, B. Mechanisms of phagocytosis and host clearance of *Pseudomonas aeruginosa. Am. J. Physiol. Lung Cell. Mol. Physiol.* 306, L591-L603 (2014).
39. Hayashi, F. et al. The innate immune response to bacterial flagellin is mediated by Toll-like receptor 5. Nature 410, 1099-1103 (2001).

40. Boyden, E. et al. Millisecond-timescale, genetically targeted optical control of neural activity. Nat. Neurosci. 8, 1263-1268 (2005).

41. Sineshchekov, O. A., Jung, K.-H. & Spudich, J. L. Two rhodopsins mediate phototaxis to low- and high-intensity light in *Chlamydomonas reinhardtii*. Proc. Natl Acad. Sci. USA 99, 8689-8694 (2002).

42. Akolpoglu, M. B. et al. High-yield production of biohybrid microalgae for on-demand cargo delivery. Adv. Sci. 7, 2001256 (2020).

43. Delalat, B. et al. Targeted drug delivery using genetically engineered diatom biosilica. Nat. Commun. 6, 8791 (2015).

44. Martel, S. et al. Flagellated magnetotactic bacteria as controlled MRI-trackable propulsion and steering systems for medical nanorobots operating in the human microvasculature. Int. J. Robot. Res. 28, 571-582 (2009).

Example 2: Gastrointestinal Tract Drug Delivery Using Algae Motors Embedded in a Degradable Capsule The use of micromotors for active drug delivery via oral administration has recently gained considerable interest. However, efficient motor-assisted delivery into the gastrointestinal (GI) tract remains challenging, owing to the short propulsion lifetime of currently used micromotor platforms. Provided here is an efficient algae-based motor platform, which takes advantage of the fast and long-lasting swimming behavior of natural microalgae in intestinal fluid to prolong local retention within the GI tract. Fluorescent dye or cell membrane-coated nanoparticle functionalized algae motors were further embedded inside a pH-sensitive capsule to enhance delivery to the small intestines. In vitro, the algae motors displayed a constant motion behavior in simulated intestinal fluid after 12 hours of continuous operation. When orally administered in vivo into mice, the algae motors substantially improved GI distribution of the dye payload compared with traditional magnesium-based micromotors, which are limited by short propulsion lifetimes, and they also enhanced retention of a model chemotherapeutic payload in the GI tract compared with a passive nanoparticle formulation. Overall, combining the efficient motion and extended lifetime of natural algae-based motors with the protective capabilities of oral capsules results in a promising micromotor platform capable of achieving greatly improved cargo delivery in GI tissue for practical biomedical applications.

*Chlamydomonas reinhardtii* was chosen in this example as a model microalgal swimmer for active payload delivery in the GI tract because of its many attractive properties, including cytocompatibility, cost-effective scalable production, good adaptability and motility in diverse aqueous environments, abundance of reactive surface groups for functionalization, and autofluorescence for ease of tracking in vivo (27, 32-34). *C. reinhardtii* swims by beating its two flagella synchronously at a frequency of 50 Hz (35), reaching high speeds up to about 200 μm/s (32, 36). It was demonstrated that *C. reinhardtii* display substantially longer propulsion in intestinal fluid compared with synthetic chemically powered Mg micromotors, which are the only type of self-propelled microrobot swimmers that have been reported for in vivo operation in the GI tract (19-22). To protect the algae motors from the harsh gastric environment, we embedded them inside a protective capsule (FIG. 6a-6c), which was prepared with an inner hydrophobic coating to entrap aqueous solution for maintaining algae viability along with an outer pH-responsive enteric polymer coating. Upon release from the capsule, the algae display constant motility in intestinal fluid (FIG. 6d). Compared with the short lifetime of commonly used Mg micromotors, the algae motors remain motile for more than 12 hours at body temperature. In vivo, this prolonged movement leads to notably improved intestinal distribution (FIG. 6e), resulting in enhanced retention of a model chemotherapeutic doxorubicin (Dox) conjugated to the algae motors. Overall, the findings indicate that natural algae-based active carriers hold great promise for oral drug delivery to enhance the treatment of GI diseases.

Figure 7A:
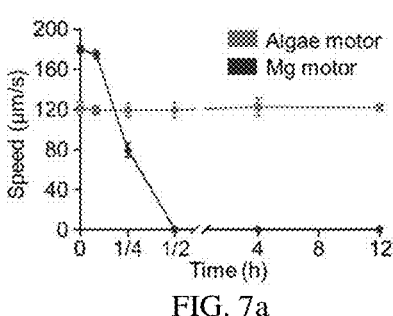
FIGS. 7a-7j. Motility of algae motors and Mg motors in SIF at room temperature.
Figure 7B:
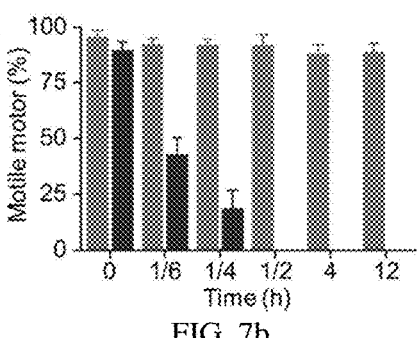
Figure 7C:
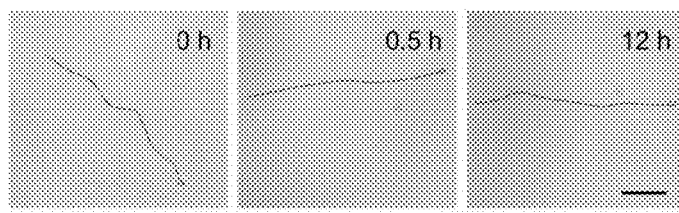
Figure 7D:
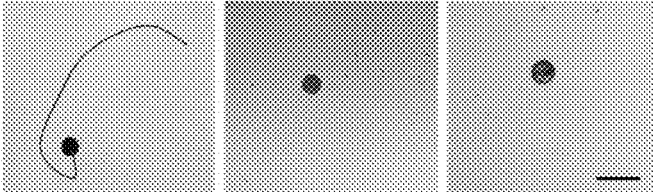

Movement of algae-based micromotors in simulated intestinal fluid. We first studied the motion properties of *C. reinhardtii*, which are commonly used as a model algal species (37), and compared them with those of Mg micromotors (FIG. 7a). Simulated intestinal fluid (SIF), mainly composed of potassium dihydrogen phosphate at pH 6.8, was used to test the movement of the algae and Mg micromotors. In SIF, the natural algae motors exhibited a stable speed profile of about 120 μm/s that lasted for a minimum of 12 hours. This consistent motile behavior is ascribed to the coordinated, self-sustained beating of algae flagella (38) even under suboptimal survival conditions, such as SIF. In contrast, the speed of Mg micromotors in SIF markedly decreased from an initial 180 to 80 μm/s after 15 min before reaching 0 μm/s after another 15 min. This sharp drop in speed reflects the rapid dissolution and depletion of the Mg engine during propulsion. The percentage of motile Mg motors also dropped to 20% after 15 min of propulsion, whereas 89% of the algae motors remained moving after 12 hours (FIG. 7b). In tracing their motion, the movement patterns of algae tracked over 2-s intervals appeared consistent over the course of 12 hours (FIG. 7c), whereas no movement was observed for Mg motors after 30 min (FIG. 7d). These data illustrated that the algae motors could self-propel efficiently in SIF and maintain consistently fast motility over long periods of time, thereby supporting their potential for active GI delivery applications.

Figure 7E:
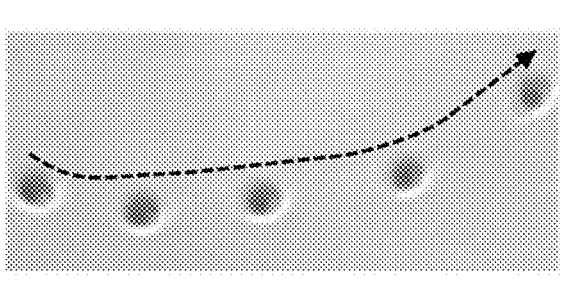
Figure 7F:
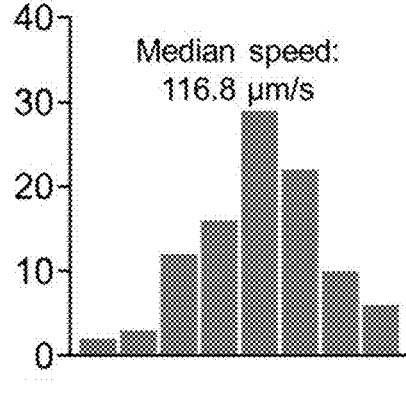
Figure 7G:
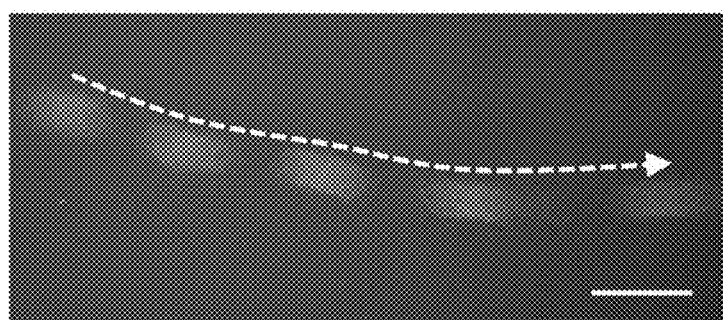
Figure 7H:
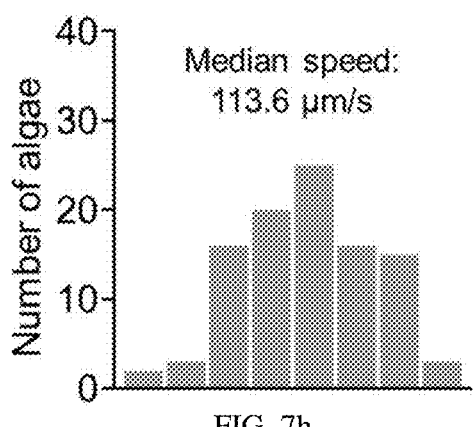
Figure 7I:
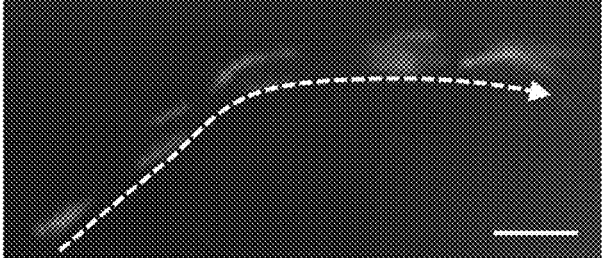
Figure 7J:
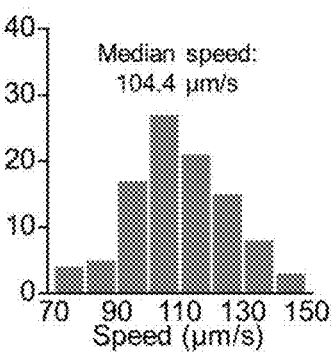

To demonstrate their potential for drug delivery, we modified the algae motors with two different cargos: a fluorescent dye and polymeric nanoparticles (NPs). The green dye fluorescein (excitation/emission=494 nm/518 nm) was first chemically conjugated to the surface of the algae (39). After dye conjugation, the algae could be fluorescently tracked (FIG. 7g, 7h), and the median speed calculated from 100 individual algae was nearly identical to that of unmodified algae (FIG. 7e, 7f) and consistent with previously reported values (32, 36). Similarly, red blood cell (RBC) membrane-coated poly(lactic-co-glycolic acid) (PLGA) NPs (40) were linked to the algae via click chemistry. To visualize the NPs on the algae, we encapsulated the fluorescent dye 1,1'-dioctadecyl-3,3,3',3'-tetramethylindocarbocyanine (DiI; excitation/emission=550 nm/567 nm) inside the PLGA core during the fabrication process. The NP-modified algae motors (denoted "algae-NP motors") exhibited a similar swimming pattern and speed distribution profile in SIF compared with unmodified algae motors (FIG. 7i, 7j). In addition, the intrinsic phototaxis of the algae was not compromised after the NP functionalization. The data here confirmed that different payloads, ranging from small molecules to NPs, can be successfully loaded onto algae motors without affecting their propulsion characteristics, further highlighting the active GI delivery potential of algae-based motor systems.

Formulation of algae motors into protective capsules. To effectively use algae motors for delivery to the GI tract in vivo, it is necessary to overcome the harsh acidic environment of the stomach, which can degrade the algae before they reach the small intestines. To address this, we modified a commercial capsule to encapsulate viable algae in an internal aqueous medium for safe passage through the stomach. First, an organosilicon solution, consisting of 4% octadecyltrimethoxysilane (OTMS) (41), was prepared to create a thin hydrophobic coating on the inside of the capsule via a thermal evaporation technique. To test the stability of a capsule with this internal coating, we encapsulated an aqueous solution containing rhodamine dye. Visually, the capsule remained unchanged, whereas notable deformation was observed for a control uncoated capsule. By changing the number of coating layers, we could modulate the degradation of the capsules, which is reflected by the release of the dye, with 10 layers of coating offering the longest delay in release in SIF. Second, the exterior surface of the capsule was coated with Eudragit L100-55, a pH-responsive polymer commonly used for protecting oral medication from harsh gastric acid conditions; previous studies have demonstrated the utility of Eudragit L100-55 as an enteric coating for enhancing the delivery of micromotors to the intestines (42). To imitate physiological conditions in the stomach, we used simulated gastric fluid (SGF) at pH 1.5, containing sodium chloride and hydrochloric acid. In our case, three layers of coating using a 7% (w/v) polymer solution offered full protection of the encapsulated cargo from SGF.

Figures 8F, 8G:
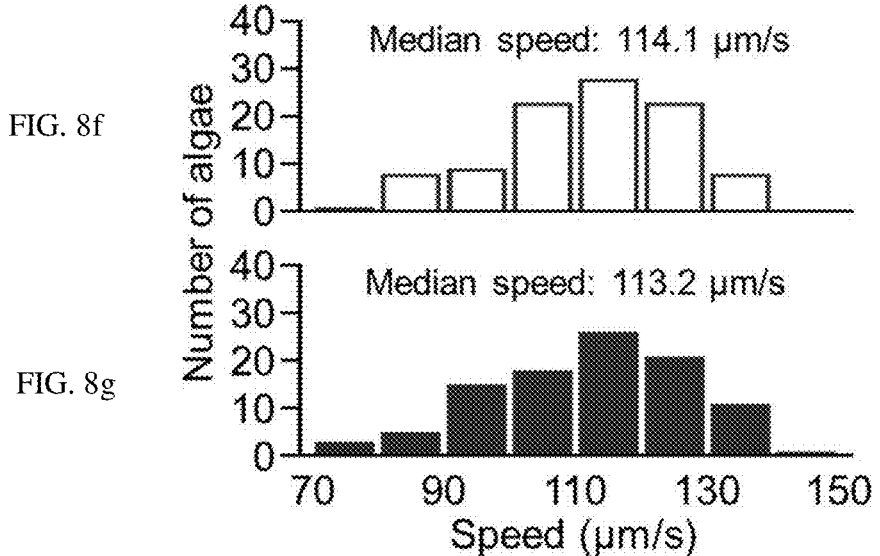

Upon changing from SGF to SIF, burst cargo release was observed within 10 min because of dissolution of the enteric coating at higher pH values. These results confirmed that it was possible to load cargo in aqueous solutions using suitably coated capsules for the GI delivery of algae motors. Next, we investigated the encapsulation of live algae into the modified capsules and their release in vitro. Algae were suspended in tris-acetate-phosphate (TAP) medium and loaded into capsules with 10 inner OTMS layers and 3 outer enteric coating layers. For visualization, the OTMS and enteric coating layers were labeled with 3',3'-dioctadecyloxacarbocyanine (DiO; excitation/emission=484 nm/501 nm) and Pacific Blue (excitation/emission=410 nm/455 nm), respectively. Under fluorescence microscopy, a strong signal was observed for both coating layers along with the autofluorescence of the algae (excitation/emission=647 nm/680 nm), confirming the successful encapsulation of algae motors into the fabricated capsule platform (FIG. 8a). In SGF, it was demonstrated that there was no release of algae from the capsules, whereas the algae motors could be released over time in SIF (FIG. 8b). The release in SIF was gradual for about 30 min, after which most of the algae was released by 45 min from the start of the experiment. The total number of released algae reached $9.15 \times 10^1$ after 45 min (FIG. 8c, 8d). Motion tracking of algae motors within the capsule and algae motors released from the capsule revealed similar patterns of movement (FIG. 8e). The median speed calculated from 100 individual algae also remained unchanged throughout the fabrication process and after release from the capsules (FIG. 8g, 8g). These data indicated that the algae motors could be effectively encapsulated and then released from the modified capsule with negligible effect on their swimming performance.

Figure 9A:
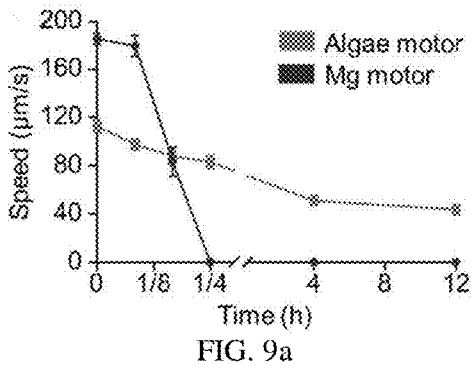
FIGS. 9a-9d. Comparison of the distribution of algae motors and Mg motors in the GI tract.
Figure 9B:
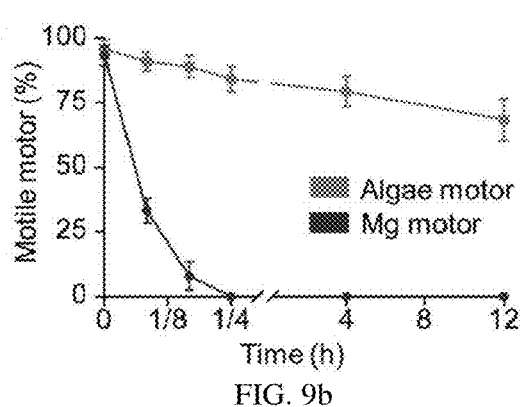

After evaluating the release of algae motors from the capsules under in vitro conditions, we investigated the delivery capabilities of the platform within the GI tract. First, mimicking the physiological conditions of the intestines, the motion behavior of algae motors and Mg motors was evaluated in SIF at 37° C. in vitro (FIG. 9a, 9b). The speed of the algae motors was affected by the elevated temperature, decreasing from 113 to 83 µm/s within 15 min of self-propulsion and further dropping to 40 µm/s after 12 hours. At the experimental endpoint, about 70% of the algae remained motile, indicating that they could survive for prolonged periods of time even under unfavorable conditions. In comparison, the conventional Mg motors rapidly lost their movement, with only 33% still propelling at a high speed of 180 µm/s after 5 min. After another 10 min, only 8% remained motile, with an average speed of 80 µm/s. This fast drop in speed and the fraction of motors displaying active motion reflected the rapid depletion of the Mg engine. The algae motors also exhibited the ability to swim in viscous simulated mucus (43) over an extended period of time, whereas the Mg motors did not. These findings illustrated the greatly improved behavior of the algae motors compared with their Mg-based counterparts for potential GI applications requiring prolonged propulsion.

Figure 9C:
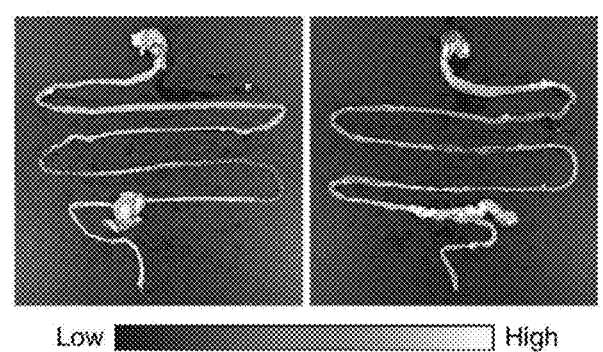
Figure 9D:
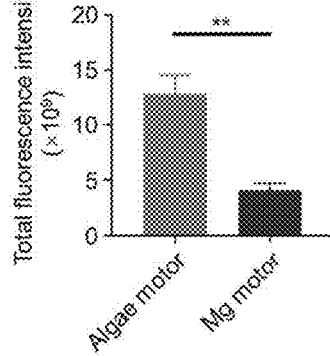

In vivo biodistribution of algae motors after oral delivery. After the in vitro tests, a study was carried out to assess the in vivo biodistribution and retention of the algae motors when delivered orally in capsule form. To facilitate imaging and quantification in biological tissue, we labeled the algae motors and Mg motors with the same fluorescent dye. The algae motors were directly conjugated with fluorescein, whereas the Mg motors were first coated with poly-L-lysine (44), then conjugated with the dye. As a result, both motors could be easily visualized under fluorescence microscopy and displayed near-identical signals that did not diminish after 6 hours in SIF at 37° C. Next, the algae motors and Mg motors were embedded in the protective capsules and administered by oral gavage to mice. At 5 hours after administration, the mice were euthanized, and their GI tracts were imaged ex vivo (FIG. 9c). Whereas a narrow distribution was observed from the fluorescent signal of the Mg motors, the signal for the algae motors was more broadly distributed through the intestines. Quantification of the total radiant efficiency within the small intestines corroborated the improved retention of the algae motors compared with the Mg motors (FIG. 9d). The observed differences in biodistribution suggested that algae, with their longlasting movement properties, could be effective at delivering drug payloads locally within the GI tract.

Figure 10A:
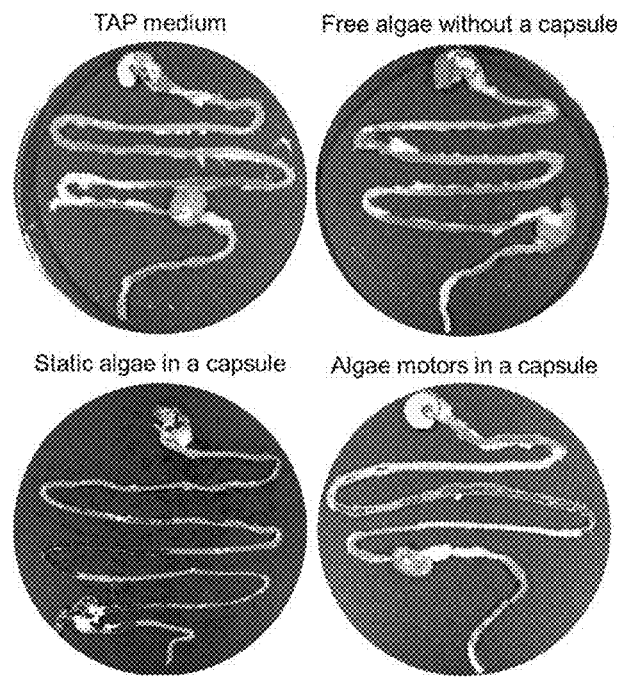
FIGS. 10a-10b. GI tract delivery of algae motors in comparison with other algae controls.
Figure 10B:
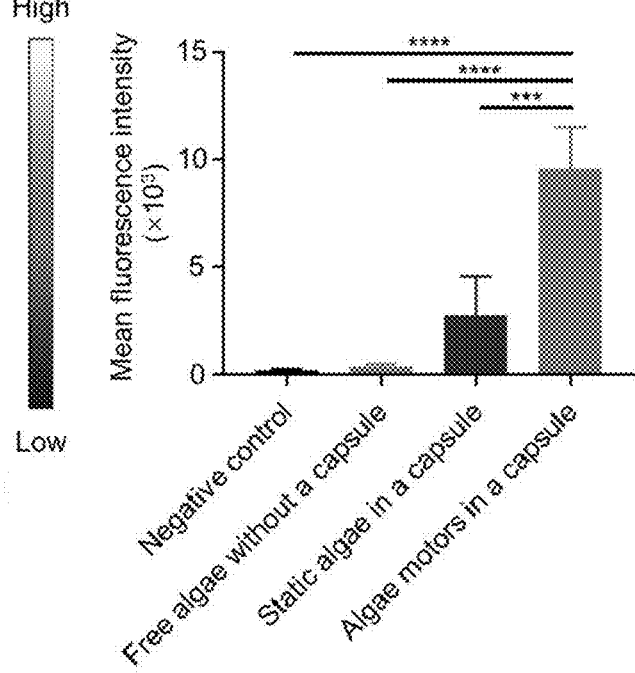

In vivo delivery of therapeutic drugs using algae motor capsules. To better understand the mechanism behind the improved biodistribution and retention of algae motors within the small intestine, we compared our algae motor capsule formulation with different control groups, including TAP medium only (negative control), free algae without a capsule, and static algae in a capsule. To prepare the static algae control, live algae were deflagellated using acetic acid and resuspended them in phosphate-buffered saline (PBS) for encapsulation. Optical visualization and scanning electron microscopy (SEM) images confirmed successful deflagellation and that the resulting static algae lost their motion capabilities in SIF at 37° C. The intrinsic fluorescence of chlorophyll a in algal chloroplasts allows for noninvasive fluorescence imaging of algae without the need for chemical modification (45). Ex vivo fluorescence imaging was performed on the GI tracts of mice receiving the various formulations with equivalent fluorescence to determine the influence of active movement and capsule protection on biodistribution (FIG. 10a). At 5 hours after oral administration, algae motors delivered inside capsules were more broadly distributed across the intestines compared with static algae that were also encapsulated. This result highlighted the importance of self-propulsion, which likely helped to increase the interaction of the algae with the intestinal wall, thus leading to enhanced retention. In addition, there was almost no signal observed in the intestines after administration of free algae, demonstrating the necessity of using the capsules to protect from the harsh stomach acid. Quantification of the fluorescent signal from each sample further supported the imaging results, as the fluorescence from the encapsulated algae motor group was 3.5-fold greater than that of the encapsulated static algae group (FIG. 10b). To control for the background signal from food contaminants within the stomach (42, 46), capsules containing algae motors labeled with Cyanine7 (Cy7; excitation/emission=750 nm/773 nm) were delivered orally, and it was confirmed that most of the algae were distributed within the intestine.

Figures 11A, 11B, 11C, 11D, 11E, 11F, 11G, 11H, 11I:
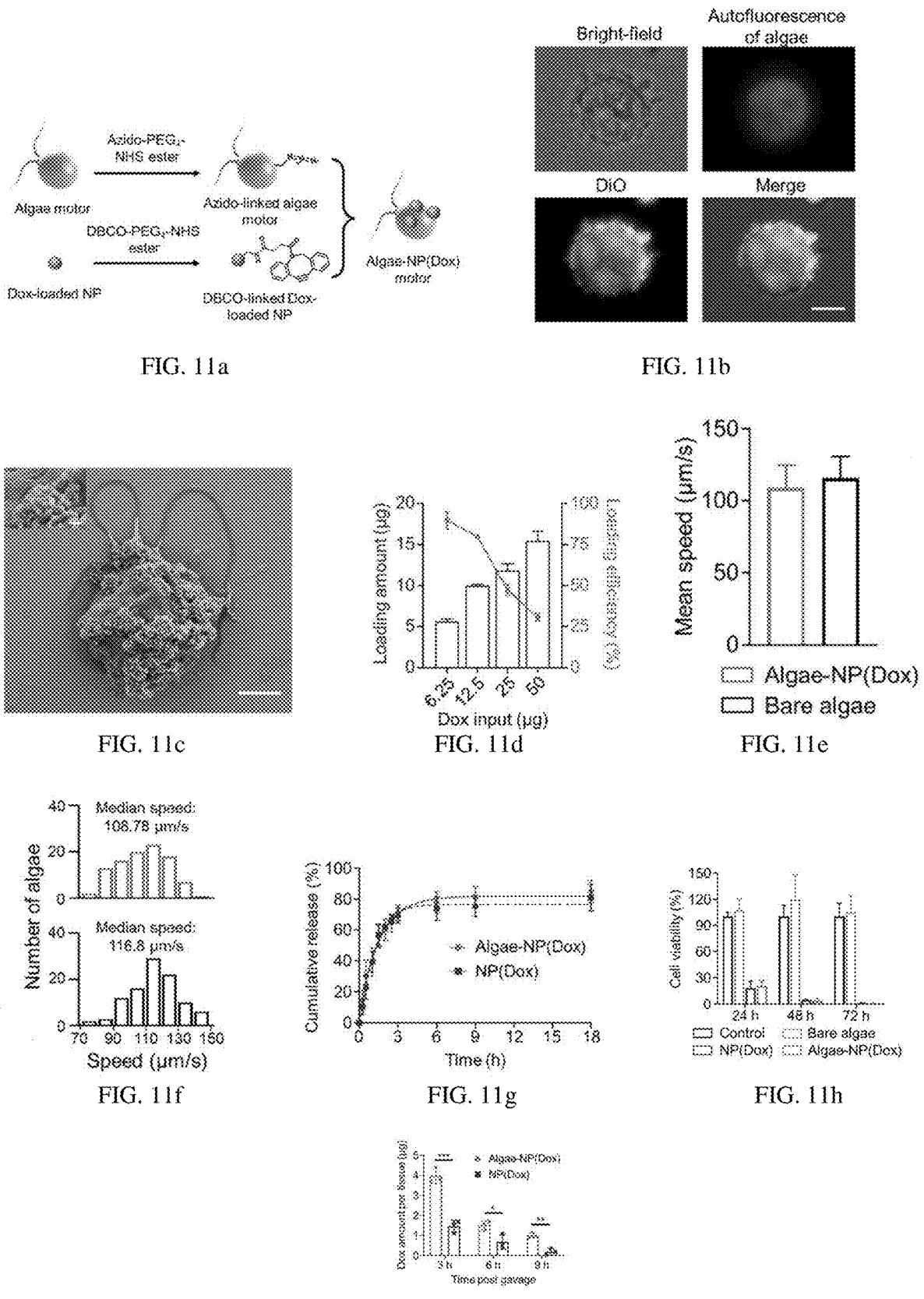
FIGS. 11a-11i. Characterization of drug-loaded algae motors.

We next explored the feasibility of using algae motors for delivering therapeutic drugs to the GI tract. Dox, a commonly used frontline chemotherapeutic agent (47), was selected as a model drug payload. First, RBC membrane-coated NPs were loaded with Dox [denoted "NP(Dox)"] via a double emulsion solvent evaporation technique (48, 49). Transmission electron microscopy (TEM) imaging confirmed the core-shell structure of the NPs. Fluorescence imaging showed colocalization of the Dox-loaded PLGA cores and the DiO-labeled RBC membrane coating, verifying successful drug loading. Next, NP(Dox) was linked to the algae [denoted "algae-NP(Dox)"] by click chemistry (FIG. 11a). Fluorescence and SEM imaging confirmed the effective binding of NP(Dox) to the algae (FIG. 11b, 11c). To test the Dox loading onto the algae, we incubated $1\times10^6$ algae with different concentrations of NP(Dox). The Dox loading yield onto the algae was measured at different NP(Dox) inputs, and the maximum loading amount (15 μg) was obtained with a 50-μg input of Dox, corresponding to a 30% loading efficiency per $10^6$ cells (FIG. 11d). It was also confirmed that Dox, either in free form or nanoparticulate form, did not influence the viability of the algae. The mean and median speed of algae-NP(Dox) measured from 100 individual algae motors were 108.69 and 108.78 μm/s, respectively, and these values were comparable with those of the bare algae (FIG. 11e, 11f). Furthermore, it was demonstrated that the drug release profile of NP(Dox) was not affected by binding to the algae motors (FIG. 11g). After loading onto algae motors, the NP(Dox) payload retained its cytotoxic activity, as it was demonstrated that algae-NP(Dox) could inhibit the growth of B16F10 melanoma cell lines in vitro (FIG. 11h). Algae-NP(Dox) and NP(Dox), both loaded into protective capsules, were then administered at the same drug dosage, followed by extraction of the intestines to quantify Dox concentration (FIG. 11i). Compared with the tissue homogenates of mice administered with NP(Dox), the samples from mice receiving algae-NP(Dox) exhibited significantly higher drug levels at all of the time points (3, 6, and 9 hours) that were tested. These data further supported the benefits of using algae motors with prolonged active self-propulsion to enhance the delivery and retention of therapeutic payloads in the small intestinal tissues. Additional applications include the use of algae motors for drug delivery to treat diseases in suitable animal models, such as for inflammatory bowel disease and bacterial gastroenteritis.

In vivo toxicity evaluation of algae motor capsules. Last, we evaluated the in vivo safety profile of the algae motor capsule platform after oral administration. A comprehensive blood chemistry panel and blood cell count were conducted 24 hours after administration (FIG. 12a, 12b). Compared with untreated control mice, the levels of all serum biochemistry markers and numbers of blood cells (RBCs, white blood cells, and platelets) in the mice receiving algae motor capsule treatment remained at normal levels. A longer-term safety study in which mice were administered with one algae motor capsule on days 0, 2, 4, and 6 also yielded the same result, whereby negligible toxicity, indicated by the minor changes in metabolic biomarkers and blood cell counts, to the mice was observed. Histological analysis of GI tract tissue sections from algae motor-treated mice stained with hematoxylin and eosin (H&E) revealed that structural integrity was preserved and that there was no immune cell infiltration into the mucosa or submucosa, indicating the lack of an inflammatory response (FIG. 12c). There was also no observable inflammation or pathological changes on H&E-stained sections from other major organs such as the heart, lungs, liver, kidneys, and spleen (FIG. 12d). Overall, these results suggested that the algae motor capsule platform is safe to use for oral drug administration.

In the present study, several key points have been considered to tackle the challenges facing algae-based active GI delivery: protection from the harsh acidic environment of the stomach en route to the intestines, selection of a suitable algal strain with long-lasting self-propulsion in intestinal fluid, and cargo/drug loading capability. By addressing these issues, we demonstrated here an algae motor capsule system for effective intestinal targeting and prolonged tissue retention. Compared with the short lifetime of current Mg-based micromotors, the algae motors displayed prolonged propulsion in GI fluid toward enhanced local delivery for the treatment of potential GI diseases and disorders. To achieve intestinal delivery, we fabricated an enteric-coated capsule modified with an inner hydrophobic organosilicon layer to effectively protect encapsulated algae from the harsh gastric fluid while maintaining their viability. The capsule fabrication, encapsulation, and release processes had a negligible effect on the viability of the algae motors. Modifying capsules in the manner described here provides an effective approach for delivering motile living organisms in aqueous media to the GI tract. To demonstrate the distinct advantages of the platform for in vivo intestinal delivery, we administered algae motor capsules orally, and their biodistribution and retention properties were compared with various controls. The algae motors displayed broader distribution and stronger retention in the GI tract compared with synthetic Mg motors. This was likely mediated by the prolonged motion of the live algae, because it was shown that static algae that were incapable of propulsion exhibited considerably less retention in the intestines. We also demonstrated that the ability of the algae motor capsule system could also be used for the delivery of a model anticancer drug to the GI tract. Moreover, the platform displayed a favorable biosafety profile after oral administration.

The characteristics of the algae motor in a capsule formulation, particularly its long-lasting self-propulsion, can be leveraged for microrobotic biomedical applications beyond the treatment of GI diseases and disorders, ranging from GI detoxication to imaging and sensing. There are several approaches in which algae motors can be improved to enhance their utility for GI delivery applications. For example, the incorporation of imaging agents could enable direct visualization of algae movement as they operate within the intestines. A recent report described a photoacoustic computed tomography-guided microrobotic system for realizing real-time navigation and monitoring of synthetic Mg motors in the intestines in vivo (53). In another example, positron emission tomography combined with computed tomography was used to evaluate the swarm behavior of enzyme-powered nanomotors in the bladder (17). By conjugating magnetic microparticles to the algae surface (32), an external magnetic navigation system could be used to precisely guide and track algae motors to target sites. The invention has further applications in clinically relevant diseases, such as those for bacterial GI infection, irritable bowel disease, or colon cancer. Microalgae can also be engineered to express biologic payloads that can be produced in situ after oral administration (54, 55). The properties of the capsules can be tuned to more precisely target specific regions of the GI tract (42). Overall, functionalized algae motors, loaded within a protective capsule, represent an attractive biohybrid motor system that can be applied across a wide range of biomedical applications.

Materials and Methods

Algae culture. The green algae *C. reinhardtii* (strain CC-125 wild-type mt+) were obtained from the *Chlamydomonas* Resource Center. The algae were transferred from the agar plate to TAP medium (Thermo Fisher Scientific) and cultured at room temperature under cycles of 12-hour sunlight and 12-hour dark.

Preparation of Mg micromotors. Mg micromotors were fabricated using 20±5-m commercial Mg microparticles (FMW20, Tangshan Weihao Magnesium Powder Co.) as the core. The Mg microparticles were washed two times with acetone and dried under an N2 current to remove impurities. Then, ~10 mg of Mg microparticles were dispersed onto glass slides, which were previously coated with 100 μl of 0.5% polyvinylpyrrolidone ethanolic solution (Spectrum Chemical). A coating of TiO2 was deposited onto the Mg microparticles by atomic layer deposition at 100° C. for 3000 cycles using a Beneq TFS 200 System, leaving a small opening at the contact point between the Mg particles and the glass slide. Last, the Mg micromotors were released by gentle scratching from the glass slide. For surface modification with a fluorescent dye, 0.5 mg of Mg micromotors were first mixed with 0.1% poly-L-lysine (Sigma-Aldrich) aqueous solution for 30 min. Then, 2 μg of 5/6-carboxyfluorescein succinimidyl ester (NHS-fluorescein; Thermo Fisher Scientific) was mixed with the motors in PBS buffer for 1 hour. The resulting fluorescein-labeled Mg micromotors were centrifuged at 3000 g for 3 min, washed with ultrapure water, and dried for further use.

Preparation of fluorescent dye-labeled algae. Green algae were washed three times with ultrapure water to remove TAP medium and then suspended in HEPES buffer (Thermo Fisher Scientific). Then, 2 μg of NHS-fluorescein was added to 1 ml of algae at 2×106 per ml and incubated for 1 hour at room temperature. After dye conjugation, the modified algae were washed three times with TAP medium to remove free dye, and then they were suspended in TAP medium for further use. Near-infrared dye-labeled algae were prepared with a similar method by replacing NHS-fluorescein with NHS-Cy7 (Lumiprobe).

Synthesis of Dox-loaded polymeric NPs. Dox-loaded polymeric NPs were synthesized following a published method with slight modification (49). First, 50 μl of 25 mg/ml Dox-HCl (Sigma-Aldrich) solution was emulsified in 500 μl of a chloroform solution containing PLGA (50 mg/ml; 50:50, 0.66 dl/g; LACTEL Absorbable Polymers) using a Fisher Scientific FB120 ultrasonic probe sonicator operating at a power of 10 W. The process lasted for 2 min with alternating cycles of 2-s power on and 2-s power off in an ice bath. Then, the emulsion was transferred to 5 ml of tris-HCl (Teknova) aqueous solution and sonicated for another 2 min. The emulsion was stirred for 3 hours to completely remove the chloroform. The NPs were centrifuged at 16,100 g for 5 min, washed three times with ultrapure water, and lyophilized for further use. NPs loaded with DiI (Thermo Fisher Scientific) were prepared using a similar procedure by replacing Dox with the dye.

Synthesis of cell membrane-coated NPs. RBC membrane-coated NPs were synthesized by a membrane cloaking technique (40). RBC membrane was mixed with PLGA cores at a 1:1 membrane protein to polymer weight ratio. The mixture was sonicated in a Fisher Scientific FS30D ultrasonic bath sonicator for 3 min. The NPs were isolated by centrifugation for 5 min at 16,100 g and washed three times with ultrapure water. To characterize NP morphology, we deposited samples onto a carbon-coated 400-mesh copper grid and stained them with 1 weight % of uranyl acetate (Electron Microscopy Sciences), followed by imaging on a JEOL 1200 EX II TEM.

Preparation of algae-NP motors. To attach NPs onto algae, we washed 1×107 green algae three times with ultrapure water and treated them with 20 μM dibenzocyclooctyne-(polyethylene glycol)4-N-hydroxysuccinimidyl ester (DB-COPEG4-NHS; Click Chemistry Tools) for 1 hour at room temperature. The NPs were incubated with 20 μM azide-PEG4-NHS for 1 hour at room temperature. Both the algae and NPs were washed five times with ultrapure water to remove the unreacted NHS ester. Then, the modified algae and NPs were mixed together and vortexed for 3 hours to complete the click chemistry reaction. After conjugation, the resulting algae-NP motors were separated by centrifugation for 3 min at 500 g, washed three times with TAP medium, and resuspended in TAP medium for further use. NP(Dox) conjugation onto the algae followed a similar method by replacing NPs with NP(Dox). To evaluate the NP(Dox) loading efficiency, we conjugated algae motors at $1×10^6$/ml to NP(Dox) with Dox content at different concentrations (6.25, 12.5, 25, and 50 μg/ml). After fabrication of the algae-NP(Dox) motor, Dox content in unbound NP(Dox) was quantified by measuring the absorbance at 480 nm using a ultraviolet-visible spectrometer. The Dox loading amount on the algae motor was calculated by subtracting the unbound Dox from the Dox input.

Phototaxis of algae-NP motors. Phototaxis studies were conducted in three-dimensional printed microfluidic channels with a 5-mm by 4-mm by 2-mm chamber. Before testing, the channel was prefilled with 50 μl of TAP medium. Then, the algae-NP motors were added to one side of the channel, whereas the other side was illuminated using a light emitting diode white light for 500 s. As a control, algae motors were added to one side without a light source on the other side. Time-lapse videos were recorded at 10 s per frame using an Invitrogen EVOS FL fluorescence microscope with a 2× objective.

Influence of Dox on algae viability. To evaluate the influence of free drug, we suspended algae motors at $1×10^6$/ml into solutions containing different concentrations (0, 5, 10, and 25 μg/ml) of Dox. After 24 hours of incubation, each sample was collected, washed three times with ultrapure water to remove free drug, and resuspended into ultrapure water. Next, the samples were stained in 5 μM SYTOX fluorescent probe (Thermo Fisher Scientific) to measure algae viability. A similar method was used to test the viability of algae after conjugation of NP(Dox).

In vitro anticancer activity of algae-NP(Dox) motors. B16-F10 mouse melanoma cell lines (CRL-6475, American Type Culture Collection) were seeded into a 96-well plate at $5×10^4$ per well and further incubated with free Dulbecco's modified Eagle's medium, free Dox, free algae, and algae- NP(Dox) motors for 24, 48, and 72 hours. All drug-containing wells used the same Dox concentration of 50 μg/ml. An MTS assay (Promega) was used to evaluate the cell viability per the manufacturer's protocol.

Algae motility analysis. To evaluate their motion, we suspended unmodified algae motors, fluorescein-conjugated algae motors, and algae-NP motors in SIF (RICCA Chemical). Then, the algae were observed at 0 min, 5 min, 15 min, 30 min, 4 hours, and 12 hours at room temperature (22° C.). In a separate experiment, algae were observed at 0 min, 5 min, 10 min, 15 min, 4 hours, and 12 hours at body temperature (37° C.). For Mg micromotor motion analysis, the motors were uniformly dispersed on a glass slide, followed by addition of SIF solution. Motion was evaluated at the same time points as above, and SIF was continuously supplemented to prevent the motors from drying. To test the influence of NP(Dox) on motility, we measured the motion of algae-NP(Dox) motors in SIF. To evaluate the operation of algae motors in a mucus-rich environment, we analyzed their motion behavior in a simulated porcine small intestinal mucus containing mucin (20 mg/ml; Alfa Aesar) (43). Brightfield movies were captured by a Nikon Eclipse Ti-S/L100 inverted optical microscope coupled with different objectives (10× and 20×) and a Hamamatsu digital camera C11440. Meanwhile, fluorescent movies were captured using a Sony RX100 V camera on an Invitrogen EVOS FL fluorescence microscope with different objectives (20× and 40×) in two fluorescence channels, green fluorescent protein (GFP) and red fluorescent protein, corresponding to fluorescein and DiI. An NIS Element tracking module was used to measure the speed of the motors in SIF.

Characterization of algae-NP motors. To confirm NP binding on the surface of the algae motors, we labeled the RBC membrane on the NPs beforehand with DiO (Thermo Fisher Scientific). Fluorescence microscopy images were captured by using an Invitrogen EVOS FL microscope in two fluorescence channels, Cy5 and GFP, corresponding to the autofluorescence of the algae and DiO. To further confirm the structure of algae-NP motors, we performed SEM to visualize their morphology. The algae-NP motors were first fixed with a 2.5% glutaraldehyde solution (Sigma-Aldrich) overnight at 4° C. and then washed three times with ultrapure water. The samples were sputtered with palladium for imaging on a Zeiss Sigma 500 SEM instrument using an acceleration voltage of 3 kV.

Fabrication of algae motor capsules. Mouse-specific size M gel capsules were supplied by Torpac. To perform the hydrophobic inner coating, we prepared 4% (w/w) of OTMS (Tokyo Chemical Industry) solution in pure ethanol and stirred it at room temperature for 2 hours. An insulin syringe was used to fill the capsule with ~4 μl of the OTMS solution, followed by a curing process at 120° C. for 1 hour to completely evaporate the solvent. This process was repeated for up to 10 times to add more coating layers, and the capsules were stored at room temperature. For algae motor encapsulation, 4 μl of algae at a concentration of $2.5 \times 10^5$ per μl in TAP medium was slowly injected into the capsule using a primed syringe pump. After algae encapsulation, the commercial enteric coating polymer Eudragit L100-55 (Evonik Industries) was selected to coat the capsule for protection from gastric acid. First, the enteric coating polymer was dissolved at 7% (w/v) in ethanol solution by stirring at room temperature overnight. The capsules were then immersed into the enteric coating solution with a dip-coating approach, followed by solvent evaporation for a total of three times. After enteric coating, the capsules were stored at room temperature. To evaluate the release of algae motors from the capsule formulation, we immersed the loaded capsules either into SGF at pH 1.5 comprising 0.2% (w/w) sodium chloride and 0.31% (w/w) hydrochloric acid or into SIF at pH 6.8 containing 0.68% (w/w) potassium dihydrogen phosphate and 0.15% (w/w) sodium hydroxide under stirring at 700 rpm. For biodistribution studies, the static algae control ($1 \times 10^6$), fluoresceinconjugated algae ($2 \times 10^6$), fluorescein-labeled Mg motors (0.5 mg), and algae-NP(Dox) motors (5 μg of Dox) were encapsulated by a similar process. To generate the static algae control, we rapidly treated live algae with 0.5 M acetic acid to remove their flagella. To quantify the autofluorescence of algae motor and static algae samples, we used a Tecan Infinite M200 plate reader.

Animal care. Mice were housed in an animal facility at the University of California San Diego (UCSD) under federal, state, local, and National Institutes of Health (NIH) guidelines. Six-week-old CD-1 male mice were purchased from Charles River Labs. Mice were maintained in standard housing with cycles of 12-hour light and 12-hour dark, ambient temperature, and normal humidity. All animal experiments were performed in accordance with NIH guidelines and approved by the Institutional Animal Care and Use Committee of UCSD.

Pharmacokinetics and biodistribution studies. To characterize the biodistribution of algae motors, we fed male CD-1 mice an alfalfa-free diet (LabDiet, St. Louis, MO, USA) starting 1 week before the experiments. To compare the biodistribution between fluorescein-labeled algae motors ($2 \times 10^6$) and Mg-based motors (0.5 mg), we administered mice with the corresponding capsules containing the motors labeled with equal amounts of dye. To evaluate the influence of active propulsion and capsule protection, we administered mice with encapsulated active algae ($1 \times 10^6$), encapsulated static algae ($1 \times 10^6$), unencapsulated active algae ($1 \times 10^6$), or PBS by oral gavage. The mice were euthanized at 5 hours after administration. The entire GI tracts were then collected, rinsed with PBS, and imaged using a Xenogen IVIS 200 system. For quantitative fluorescent measurements, the collected tissues were weighed and then homogenized in PBS. The fluorescent signals were quantified using a Tecan Infinite M200 plate reader. To evaluate drug retention, we administered male CD-1 mice with algae-NP(Dox) motor capsules (5 μg of Dox), NP(Dox) capsules (5 μg of Dox), and PBS via oral gavage. At 3, 6, and 9 hours after oral administration, the GI tracts were then collected, weighed, and then homogenized in PBS. The amount of Dox was quantified using a Tecan Infinite M200 plate reader based on absorbance readings at 480 nm.

In vivo safety studies. Mice were euthanized at 24 hours after oral administration of TAP medium or encapsulated algae motors (1×106). For the comprehensive metabolic panel, aliquots of blood were allowed to coagulate, and the serum was collected by centrifugation. To obtain blood cell counts, we collected whole blood into potassium EDTA collection tubes (Sarstedt). For long-term safety, mice were administered algae motors in a capsule on days 0, 2, 4, and 6, and they were euthanized for analysis on day 7. Laboratory tests were performed by the UCSD Animal Care Program Diagnostic Services Laboratory. To perform the histological analysis, we sectioned different parts of the GI tract and major organs and stained them with H&E (Leica Biosystems), followed by imaging using a Hamamatsu Nanozoomer 2.0-HT slide scanning system.

Statistical analysis. All experiments were repeated as independent experiments several times, as shown by the figure captions. The results are reported as means±SD. A two-tailed, Student's t test was used for testing the significance between two groups. A one-way analysis of variance (ANOVA) with Dunnett's test was performed to test the significance for multiple comparisons. Statistical significance is indicated as $*P<0.05$, $P<0.01$, $*P<0.001$, and $****P<0.0001$. No data were excluded from the analysis. Samples were randomly allocated to different experimental groups. Organisms were cultured and maintained in the same environment and randomly allocated to each group. Investigators were not blinded during data collection and analysis.

REFERENCES

1 J. Li, B. E.-F. de Ávila, W. Gao, L. Zhang, J. Wang, Micro/nanorobots for biomedicine: Delivery, surgery, sensing, and detoxification. Sci. Robot. 2, eaam6431 (2017).

2 S. Hua, Advances in oral drug delivery for regional targeting in the gastrointestinal tract—influence of physiological, pathophysiological and pharmaceutical factors. Front. Pharmacol. 11, 524 (2020).

3 L. M. Ensign, R. Cone, J. Hanes, Oral drug delivery with polymeric nanoparticles: The gastrointestinal mucus barriers. Adv. Drug Deliv. Rev. 64, 557-570 (2012).

4 A. Abramson, M. R. Frederiksen, A. Vegge, B. Jensen, M. Poulsen, B. Mouridsen, M. O. Jespersen, R. K. Kirk, J. Windum, F. Hubilek, J. J. Water, J. Fels, S. B. Gunnarsson, A. Bohr, E. M. Straarup, M. W. Hvitfeld Ley, X. Lu, J. Wainer, J. Collins, S. Tamang, K. Ishida, A. Hayward, P. Herskind, S. T. Buckley, N. Roxhed, R. Langer, U. Rahbek, G. Traverso, Oral delivery of systemic monoclonal antibodies, peptides and small molecules using gastric auto-injectors. Nat. Biotechnol. 40, 103-109 (2022).

5 A. Abramson, E. Caffarel-Salvador, V. Soares, D. Minahan, R. Y. Tian, X. Lu, D. Dellal, Y. Gao, S. Kim, J. Wainer, J. Collins, S. Tamang, A. Hayward, T. Yoshitake, H.-C. Lee, J. Fujimoto, J. Fels, M. R. Frederiksen, U. Rahbek, N. Roxhed, R. Langer, G. Traverso, A luminal unfolding microneedle injector for oral delivery of macromolecules. Nat. Med. 25, 1512-1518 (2019).

6 J. Wu, H. Yuk, T. L. Sarrafian, C. F. Guo, L. G. Griffiths, C. S. Nabzdyk, X. Zhao, An off-the-shelf bioadhesive patch for sutureless repair of gastrointestinal defects. Sci. Transl. Med. 14, eabh2857 (2022).

7 X. Liu, C. Steiger, S. Lin, G. A. Parada, J. Liu, H. F. Chan, H. Yuk, N. V. Phan, J. Collins, S. Tamang, G. Traverso, X. Zhao, Ingestible hydrogel device. Nat. Commun. 10, 493 (2019).

8 N. G. Lamson, A. Berger, K. C. Fein, K. A. Whitehead, Anionic nanoparticles enable the oral delivery of proteins by enhancing intestinal permeability. Nat. Biomed. Eng. 4, 84-96 (2020).

9 P. Angsantikul, K. Peng, A. M. Curreri, Y. Chua, K. Z. Chen, J. Ehondor, S. Mitraotri, Ionic liquids and deep eutectic solvents for enhanced delivery of antibodies in the gastrointestinal tract. Adv. Funct. Mater. 31, 2002912 (2020).

10 A. Ghosh, L. Li, R. P. Dash, N. Gupta, J. Lam, Q. Jin, V. Akshintala, G. Pahapale, W. Liu, A. Sarkar, R. Rais, D. H. Gracias, F. M. Selaru, Gastrointestinal-resident, shape-changing microdevices extend drug release in vivo. Sci. Adv. 6, eabb4133 (2020).

11 C. Gao, Y. Wang, Z. Ye, Z. Lin, X. Ma, Q. He, Biomedical micro-/nanomotors: From overcoming biological barriers to in vivo imaging. Adv. Mater. 33, 2000512 (2020).

12 C. K. Schmidt, M. Medina-Sánchez, R. J. Edmondson, O. G. Schmidt, Engineering microrobots for targeted cancer therapies from a medical perspective. Nat. Commun. 11, 5618 (2020).

13 Z. Wu, Y. Chen, D. Mukasa, O. S. Pak, W. Gao, Medical micro/nanorobots in complex media. Chem. Soc. Rev. 49, 8088-8112 (2020).

14 B. Wang, K. Kostarelos, B. J. Nelson, L. Zhang, Trends in micro-/nanorobotics: Materials development, actuation, localization, and system integration for biomedical applications. Adv. Mater. 33, 2002047 (2020).

15 B. Wang, K. F. Chan, K. Yuan, Q. Wang, X. Xia, L. Yang, H. Ko, Y.-X. J. Wang, J. J. Y Sung, P. W. Y. Chiu, L. Zhang, Endoscopy-assisted magnetic navigation of biohybrid soft microrobots with rapid endoluminal delivery and imaging. Sci. Robot. 6, eabd2813 (2021).

16 H. Zhang, Z. Li, C. Gao, X. Fan, Y. Pang, T. Li, Z. Wu, H. Xie, Q. He, Dual-responsive biohybrid neutrobots for active target delivery. Sci. Robot. 6, eaaz9519 (2021).

17 A. C. Hortelao, C. Simó, M. Guix, S. Guallar-Garrido, E. Julián, D. Vilela, L. Rejc, P. Ramos-Cabrer, U. Cossío, V. Gómez-Vallejo, T. Patiño, J. Llop, S. Sánchez, Swarming behavior and in vivo monitoring of enzymatic nanomotors within the bladder. Sci. Robot. 6, eabd2823 (2021).

18 Z. Wu, J. Troll, H.-H. Jeong, Q. Wei, M. Stang, F. Ziemssen, Z. Wang, M. Dong, S. Schnichels, T. Qiu, P. Fischer, A swarm of slippery micropropellers penetrates the vitreous body of the eye. Sci. Adv. 4, eaat4388 (2018).

19 B. E.-F. de Ávila, P. Angsantikul, J. Li, M. A. Lopez-Ramirez, D. E. Ramirez-Herrera, S. Thamphiwatana, C. Chen, J. Delezuk, R. Samakapiruk, V. Ramez, M. Obonyo, L. Zhang, J. Wang, Micromotor-enabled active drug delivery for in vivo treatment of stomach infection. Nat. Commun. 8, 272 (2017).

20 X. Wei, M. Beltrán-Gastélum, E. Karshalev, B. Esteban-Fernández de Ávila, J. Zhou, D. Ran, P. Angsantikul, R. H. Fang, J. Wang, L. Zhang, Biomimetic micromotor enables active delivery of antigens for oral vaccination. Nano Lett. 19, 1914-1921 (2019).

21 L. Cai, C. Zhao, H. Chen, L. Fan, Y. Zhao, X. Qian, R. Chai, Suction-cup-inspired adhesive micromotors for drug delivery. Adv. Sci. 9, 2103384 (2021).

22 E. Karshalev, Y. Zhang, B. Esteban-Fernández de Ávila, M. Beltrán-Gastélum, Y. Chen, R. Mundaca-Uribe, F. Zhang, B. Nguyen, Y. Tong, R. H. Fang, L. Zhang, J. Wang, Micromotors for active delivery of minerals toward the treatment of iron deficiency anemia. Nano Lett. 19, 7816-7826 (2019).

23 J. Wang, Nanomachines: Fundamentals and Applications (John Wiley & Sons, 2013).

24 Z. Hosseinidoust, B. Mostaghaci, O. Yasa, B.-W. Park, A. V. Singh, M. Sitti, Bioengineered and biohybrid bacteria-based systems for drug delivery. Adv. Drug Deliv. Rev. 106, 27-44 (2016).

25 L. Ricotti, B. Trimmer, A. W. Feinberg, R. Raman, K. K. Parker, R. Bashir, M. Sitti, S. Martel, P. Dario, A. Menciassi, Biohybrid actuators for robotics: A review of devices actuated by living cells. Sci. Robot. 2, eaaq0495 (2017).

26 V. Magdanz, S. Sanchez, O. G. Schmidt, Development of a sperm-flagella driven micro-biorobot. Adv. Mater. 25, 6581-6588 (2013).

27 F. Zhang, Z. Li, L. Yin, Q. Zhang, N. Askarinam, R. Mundaca-Uribe, F. Tehrani, E. Karshalev, W. Gao, L. Zhang, J. Wang, ACE2 receptor-modified algae-based microrobot for removal of SARS-CoV-2 in wastewater. J. Am. Chem. Soc. 143, 12194-12201 (2021).

28 O. Felfoul, M. Mohammadi, S. Taherkhani, D. De Lanauze, Y. Z. Xu, D. Loghin, S. Essa, S. Jancik, D. Houle, M. Lafleur, L. Gaboury, M. Tabrizian, N. Kaou, M. Atkin, T. Vuong, G. Batis N. Beauchemin, D. Radzioch, S. Martel, Magneto-aerotactic bacteria deliver drug-containing nanoliposomes to tumour hypoxic regions. Nat. Nanotechnol. 11, 941-947 (2016).

29 H. Xu, M. Medina-Sánchez, V. Magdanz, L. Schwarz, F. Hebenstreit, O. G. Schmidt, Spermhybrid micromotor for targeted drug delivery. ACS Nano 12, 327-337 (2018).

30 M. Medina-Sánchez, L. Schwarz, A. K. Meyer, F. Hebenstreit, O. G. Schmidt, Cellular cargo delivery: Toward assisted fertilization by sperm-carrying micromotors. Nano Lett. 16, 555-561 (2015).

31 S. Xie, L. Zhao, X. Song, M. Tang, C. Mo, X. Li, Doxorubicin-conjugated *Escherichia coli* Nissle 1917 swimmers to achieve tumor targeting and responsive drug release. J. Control. Release 268, 390-399 (2017).

32 O. Yasa, P. Erkoc, Y. Alapan, M. Sitti, Microalga-powered microswimmers toward active cargo delivery. Adv. Mater. 30, 1804130 (2018).

33 M. B. Akolpoglu, N. O. Dogan, U. Bozuyuk, H. Ceylan, S. Kizilel, M. Sitti, High-yield production of biohybrid microalgae for on-demand cargo delivery. Adv. Sci. 7, 2001256 (2020).

34 I. P. Kerschgens, K. Gademann, Antibiotic algae by chemical surface engineering. Chembiochem 19, 439-443 (2018).

35 T. J. Böddeker, S. Karpitschka, C. T. Kreis, Q. Magdelaine, O. Bäumchen, Dynamic force measurements on swimming *Chlamydomonas* cells using micropipette force sensors. J. R. Soc. Interface 17, 20190580 (2020).

36 D. B. Weibel, P. Garstecki, D. Ryan, W. R. DiLuzio, M. Mayer, J. E. Seto, G. M. Whitesides, Microooxen: Microorganisms to move microscale loads. Proc. Natl. Acad. Sci. U.S.A. 102, 11963-11967 (2005).

37 B. P.-H. Huang, *Chlamydomonas reinhardtii*: A model system for the genetic analysis of flagellar structure and motility. Int. Rev. Cytol. 99, 181-215 (1986).

38 K. Y. Wan, R. E. Goldstein, Coordinated beating of algal flagella is mediated by basal coupling. Proc. Natl. Acad. Sci. U.S.A. 113, E2784-E2793 (2016).

39 S. Kalkhof, A. Sinz, Chances and pitfalls of chemical cross-linking with amine-reactive Nhydroxysuccinimide esters. Anal. Bioanal. Chem. 392, 305-312 (2008).

40 C.-M. J. Hu, L. Zhang, S. Aryal, C. Cheung, R. H. Fang, L. Zhang, Erythrocyte membrane-camouflaged polymeric nanoparticles as a biomimetic delivery platform. Proc. Natl. Acad. Sci. U.S.A. 108, 10980-10985 (2011).

41 J. D. Cox, M. S. Curry, S. K. Skirboll, P. L. Gourley, D. Y. Sasaki, Surface passivation of a microfluidic device to glial cell adhesion: A comparison of hydrophobic and hydrophilic SAM coatings. Biomaterials 23, 929-935 (2002).

42 J. Li, S. Thamphiwatana, W. Liu, B. Esteban-Fernández de Ávila, P. Angsantikul, E. Sandraz, J. Wang, T. Xu, F. Soto, V. Ramez, X. Wang, W. Gao, L. Zhang, J. Wang, Enteric micromotor can selectively position and spontaneously propel in the gastrointestinal tract. ACS Nano 10, 9536-9542 (2016).

43 M. Boegh, H. M. Nielsen, Mucus as a barrier to drug delivery—Understanding and mimicking the barrier properties. Basic Clin. Pharmacol. Toxicol. 116, 179-186 (2015).

44 F. Zhang, R. Mundaca-Uribe, H. Gong, B. Esteban-Fernández de Ávila, M. Beltrán-Gastélum, E. Karshalev, A. Nourhani, Y. Tong, B. Nguyen, M. Gallot, Y. Zhang, L.

Zhang, J. Wang, A macrophage-magnesium hybrid biomotor: Fabrication and characterization. Adv. Mater. 31, 1901828 (2019).

45 D. Zhong, D. Zhang, W. Chen, J. He, C. Ren, X. Zhang, N. Kong, W. Tao, M. Zhou, Orally deliverable strategy based on microalgal biomass for intestinal disease treatment. Sci. Adv. 7, eabi9265 (2021).

46 Y. Inoue, K. Izawa, S. Kiryu, A. Tojo, K. Ohtomo, Diet and abdominal autofluorescence detected by in vivo fluorescence imaging of living mice. Mol. Imaging 7, 21-27 (2008).

47 O. Tacar, P. Sriamornsak, C. R. Dass, Doxorubicin: An update on anticancer molecular action, toxicity and novel drug delivery systems. J. Pharm. Pharmacol. 65, 157-170 (2013).

48 R. H. Fang, A. V. Kroll, W. Gao, L. Zhang, Cell membrane coating nanotechnology. Adv. Mater. 30, 1706759 (2018).

49 N. Yang, Y. Ding, Y. Zhang, B. Wang, X. Zhao, K. Cheng, Y. Huang, M. Taleb, J. Zhao, W.-F. Dong, Surface functionalization of polymeric nanoparticles with umbilical cord-derived mesenchymal stem cell membrane for tumor-targeted therapy. ACS Appl. Mater. Interfaces 10, 22963-22973 (2018).

50 X. Yan, Q. Zhou, M. Vincent, Y. Deng, J. Yu, J. Xu, T. Xu, T. Tang, L. Bian, Y.-X. J. Wang, K. Kostarelos, L. Zhang, Multifunctional biohybrid magnetite microrobots for imaging-guided therapy. Sci. Robot. 2, eaaq1155 (2017).

51 H.-M. D. Wang, X.-C. Li, D.-J. Lee, J.-S. Chang, Potential biomedical applications of marine algae. Bioresour. Technol. 244, 1407-1415 (2017).

52 Y. Qiao, F. Yang, T. Xie, Z. Du, D. Zhong, Y. Qi, Y. Li, W. Li, Z. Lu, J. Rao, Y. Sun, M. Zhou, Engineered algae: A novel oxygen-generating system for effective treatment of hypoxic cancer. Sci. Adv. 6, eaba5996 (2020).

53 Z. Wu, L. Li, Y. Yang, P. Hu, Y. Li, S.-Y. Yang, L. V. Wang, W. Gao, A microrobotic system guided by photoacoustic computed tomography for targeted navigation in intestines in vivo. Sci. Robot. 4, eaax0613 (2019).

54 B. W. Jester, H. Zhao, M. Gewe, T. Adame, L. Perruzza, D. T. Bolick, J. Agosti, N. Khuong, R. Kuestner, C. Gamble, K. Cruickshank, J. Ferrara, R. Lim, T. Paddock, C. Brady, S. Ertel, M. Zhang, A. Pollock, J. Lee, J. Xiong, M. Tasch, T. Saveria, D. Doughty, J. Marshall, D. Carrieri, L. Goetsch, J. Dang, N. Sanjaya, D. Fletcher, A. Martinez, B. Kadis, K. Sigmar, E. Afreen, T. Nguyen, A. Randolph, A. Taber, A. Krzeszowski, B. Robinett, D. B. Volkin, F. Grassi, R. Guerrant, R. Takeuchi, B. Finrow, C. Behnke, J. Roberts, Development of *spirulina* for the manufacture and oral delivery of protein therapeutics. Nat. Biotechnol. 40, 974 (2022).

55 M. A. Scranton, J. T. Ostrand, F. J. Fields, S. P. Mayfield, *Chlamydomonas* as a model for biofuels and bio-products production. Plant J. 82, 523-531 (2015).

Example 3: Biohybrid Microrobots Locally and Actively Deliver Drug-Loaded Nanoparticles to Inhibit the Progression of Lung Metastasis Lung metastasis poses a formidable challenge in the realm of cancer treatment, with conventional chemotherapy often falling short due to limited targeting and low accumulation in the lungs. Here, we show a microrobot approach utilizing motile algae for localized delivery of drug-loaded nanoparticles to address lung metastasis challenges. The biohybrid microrobot (denoted "algae-NP(DOX)-robot") combines green microalgae with red blood cell membrane-coated nanoparticles containing doxorubicin, a representative chemotherapeutic drug. Microalgae provide autonomous propulsion in the lungs, leveraging controlled drug release and enhanced drug dispersion to exert anti-metastatic effects. Upon intratracheal administration, algae-NP(DOX)-robots efficiently transport their drug payload deep into the lungs while maintaining continuous motility. This strategy leads to rapid drug distribution, improved tissue accumulation, and prolonged retention compared to passive drug-loaded nanoparticles and free drug controls. In a melanoma lung metastasis model, algae-NP(DOX)-robots exhibit substantial improvement in therapeutic efficacy, reducing metastatic burden and extending survival compared to control groups. Overall, this microrobot-based active delivery system opens up exciting possibilities for precision medicine in the management of lung metastasis.

The lungs represent the most prominent target organ for cancer metastasis[1], occurring in 20% to 54% of patients diagnosed with malignant tumors that have metastasized[2]. Systemic chemotherapy is a common approach for treating lung metastases[4]; however, its effectiveness has been suboptimal due to poor lung accumulation and targeting issues[5]. Currently, there is no specific treatment tailored for lung metastasis[3]. Recently, nanotechnology has emerged as a promising approach for improving the therapeutic outcomes of advanced metastatic malignancies[6]. Nevertheless, the systemic administration of nanoparticles faces challenges from various biological barriers, often leading to the inefficiency of conventional nanoformulations in accumulating at metastatic sites[7-9].

The unique features and microenvironment of the lungs make them an attractive target for local drug delivery[10]. For example, the large surface area of the alveoli is beneficial for rapid drug absorption[11] and prolonged drug deposition into the lungs[12]. Extracellular enzyme levels for metabolic breakdown are minimal in the respiratory tract, thus enabling delivered payloads to avoid the first-pass metabolism that is characteristic of oral or intravenous administration routes[13]. For the treatment of lung conditions, site-specific delivery enables high local concentrations to be achieved while reducing side effects on normal tissues caused by systemic exposure[14]. While pulmonary delivery via inhalation or dry powder formulations has shown promise for treating pulmonary diseases[15-18], the rapid elimination of inhaled medications and limited delivery efficiency have constrained their therapeutic impact[7, 19]. Consequently, developing highly efficient alternative pulmonary delivery platforms is crucial to surpass current inhalation treatments and achieve more effective lung cancer treatment.

In recent years, extensive research efforts have been dedicated to leveraging microrobots for disease treatment[20-29]. The active movement of drug-loaded microrobots holds the potential to enhance drug delivery efficiency and improve therapeutic efficacy. Compared to traditional passive drug delivery systems, microrobot-based active delivery exhibits appealing in vivo capabilities, such as transporting therapeutic payloads to target sites[30-32], penetrating tissue for enhanced retention, selectively positioning in the gastrointestinal tract[33-35], and accumulating and penetrating tumors[24, 26, 36]. Special emphasis has been placed on the development of biohybrid microrobots, achieved by functionalizing unicellular microorganisms like algae, bacteria, sperm, etc., with synthetic components[24, 35, 37-39]. Among these microorganisms, algae have demonstrated considerable promise as motile biomotors in various biomedical and environmental applications[40]. Microalgae-based robotic systems possess distinct advantages, including sustained autonomous motility in localized environments, phototaxis, autofluorescence for imaging, and adaptability to different surroundings[35, 37, 41-45]. Notably, algae-based microrobots offer significant benefits for the treatment of pulmonary diseases, including rapid distribution throughout the lungs, prolonged retention, active drug delivery, and controlled drug release. These advantages have recently demonstrated remarkable antibacterial efficacy in combating pneumonia[29].

In this work, algae-based biohybrid microrobots were design for the active local delivery of chemotherapeutic drugs to combat melanoma lung metastasis (FIG. 13a). The microrobot platform (denoted "algae-NP(DOX)-robot") consists of natural green algae functionalized with red blood cell membrane-coated doxorubicin (DOX)-loaded polymeric poly(lactic-co-glycolic acid) (PLGA) nanoparticles for enhanced drug delivery to treat lung cancer. The prolonged swimming of microalgae facilitates the efficient distribution of chemotherapeutics throughout the lungs, providing an effective strategy for addressing lung metastasis. Biodegradable PLGA nanoparticles play a crucial role in encapsulating anticancer drugs for controlled release, while the cell membrane coating imparts biomimetic properties that shield the therapeutic payload from the biological environment. These biohybrid microrobots, featuring functionalized microalgae, retain their attractive intrinsic motion capabilities even under physiological conditions, persisting seamlessly even after drug loading. Through intratracheal administration of algae-NP(DOX)-robots into the lungs of mice, their enhanced distribution and prolonged presence was demonstrated, resulting in a more effective accumulation of the loaded drugs. These findings align with the slow uptake of biohybrid robots by alveolar macrophages, which is likely a consequence of the unique motion capabilities of the microalgae carriers. Overall, there is a substantial improvement in therapeutic efficacy against melanoma lung metastasis, as evidenced by the reduced lung metastatic burden and substantially improved median survival time compared to passive drug-loaded nanoparticles and free drug controls.

Preparation of algae-NP(DOX)-robot. We first followed a well-established nanoprecipitation method to prepare DOX-loaded PLGA nanoparticles (denoted "PLGA(DOX)")[46]. A cell membrane coating was used to further shield the therapeutic agents. Red blood cells (RBCs) were chosen as the cell source for membrane coating due to their biocompatibility and ease of collection for scalable manufacturing[47]. To create RBC membrane-coated drug-loaded nanoparticles (denoted "NP(DOX)"), RBC membrane-derived vesicles were prepared and coated onto PLGA(DOX) through a sonication-based method[47]. Transmission electron microscopy (TEM) analysis confirmed the presence of a core-shell structure in NP(DOX) after the cell membrane coating (FIG. 13b). The final cell membrane-coated nanoparticles were relatively monodisperse, as illustrated by scanning electron microscopy (SEM). Coating with the cell membrane increased the hydrodynamic diameter from 89.7±1.3 nm to 108.1±6.0 nm (FIG. 13c). Additionally, the zeta potential of NP(DOX) was found to be −3 mV, in contrast to the +35 mV of PLGA(DOX), indicating that the cell membrane coating shielded the positively charged surface of PLGA(DOX) (FIG. 13d). A drug loading yield (DOX weight/PLGA weight) of 6.2 wt % was determined for PLGA(DOX), corresponding to a 24.8% encapsulation efficiency (DOX loading/DOX input); the loading yield of NP(DOX) decreased slightly to 5.6 wt %, indicating that that the cell membrane coating had a minor impact on drug loading (FIG. 13e, 13f).

Figure 13H:
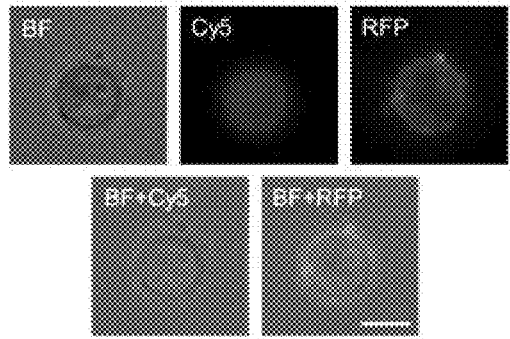
Figure 13I:
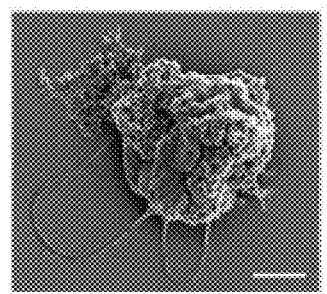
Figure 13J:
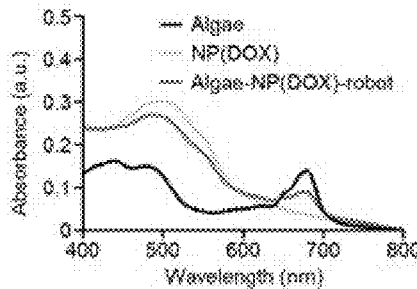
Figure 13K:
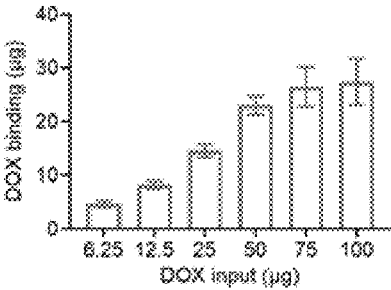
Figure 13L:
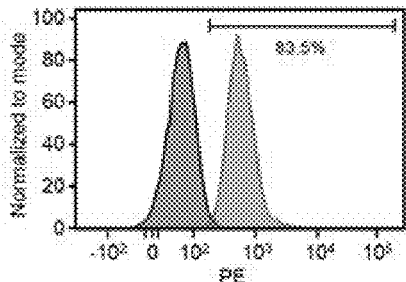

To prepare algae-NP(DOX)-robots, we further conjugated NP(DOX) onto the surface of microalgae. We selected green algae, *Chlamydomonas reinhardtii*, to actuate our microrobot formulation due to its many attractive properties including effective and extended self-propulsion in biological media[29], versatile surface chemical groups (e.g. —COOH, —NH$_2$) for cargo conjugation[41,45], biocompatibility[48], autofluorescence for tracking and imaging[29], and recognition as safe for use by the United States FDA (GRAS Notice, no. 773). To attach NP(DOX) to the algae surface, we employed a straightforward click chemistry approach, involving bridging dibenzocyclooctyne (DBCO)-modified microalgae with azido-functionalized NP(DOX) (FIG. 13g). The binding of NP(DOX) was visually confirmed using fluorescence imaging. Enlarged images showed individual algae, with their chloroplast autofluorescence, surrounded by punctate signal originating from NP(DOX) (FIG. 13h). Binding of NP(DOX) to microalgae was further confirmed by scanning electron microscopy (SEM), which also revealed negligible damage caused by the binding process with the microalgae retaining their two flagella (FIG. 13i). The optical absorption spectrum of algae-NP(DOX)-robots exhibited absorption peaks at wavelengths of 480 nm and 680 nm, corresponding to the absorption of DOX and algae chlorophyll a, respectively[49] (FIG. 13j). The loading of DOX onto the microalgae could be controlled by varying the initial input DOX concentration (FIG. 13k). A DOX loading capacity as high as 27 μg per 1×10$^6$ microalgae was obtained upon increasing the drug input concentration. In particular, a saturation level was achieved at approximately 50 μg of drug input, corresponding to a binding efficiency of 46%. The binding efficiency dropped dramatically upon increasing the drug input concentration, ranging from 73 wt % at the lowest measured input of 6.25 μg down to 27.4 wt % at the highest input of 100 μg. Flow cytometry studies were conducted to quantify the percentage of the algae population that could be bound with NP(DOX). It was discovered that when 1×10$^6$ algae were mixed with 25 g of DOX in NP(DOX), 83.9% of them were positive for nanoparticle signal; this percentage rose to 96.3% upon raising the NP(DOX) input to 100 μg (FIG. 13l).

Motion behavior and in vitro characterizations of algae-NP(DOX)-robot. Microalgae exhibit various autonomous functions, such as self-propulsion and phototaxis, allowing them to respond to the environment[37]. These characteristics can be harnessed for designated tasks to support the operation of biohybrid microrobots. We therefore investigated the impact of drug loading on the functional properties of microalgae. The speed and percentage of motile biohybrid microrobots with different drug inputs were first measured in water at 22° C. (FIG. 14a, 14b). Algae-NP(DOX)-robot maintained a steady speed of ~100 m s$^{-1}$ and a high motility ratio at DOX inputs of 6.25 and 25 g, respectively. However, when the DOX input was increased to 100 μg, only 52% of algae-robots remained motile, with the average speed being reduced to 82.9 m s$^{-1}$. Consequently, a DOX input of 25 ag, was selected for subsequent in vitro and in vivo studies. Representative characteristic fluorescence motion tracking trajectories of a single algae-NP(DOX)-robot over a 2-second period are displayed in FIG. 14c. These illustrate that the moving microrobots could be tracked continuously via fluorescence imaging without further modifications. To mimic conditions in pulmonary delivery, the motion features of the microrobots were examined also in simulated lung fluid (SLF) at 37° C. (FIG. 14d, 14e). After 2 h of incubation, the speed of the algae-NP(DOX)-robots decreased from 100.3 μm s$^{-1}$ to 46.7 μm s$^{-1}$, showing a similar trend to the algae without NP(DOX) conjugation. The corresponding motility ratio of microrobots decreased from 92.5% to 52.8% after 2 h, which was also comparable to the change for the bare algae group. The alterations in speed and reduced motility are attributed to the effect of the higher temperature on the synthesis and function of the dynein protein, which in turn affects the beating of flagella[50]. To further evaluate the impact of the NP(DOX) conjugation on the algae motility, the mean speed distribution of the algae-NP(DOX)-robots after 2 h of operation at 37° C. was also analyzed (FIG. 14f). We observed the speed of 100 algae for both algae-NP(DOX)-robots and bare algae and found that the speed of algae-NP(DOX)-robots decreased slightly, with 80% of them moving within the range of 35-75 μm s$^{-1}$, whereas 80% of bare algae retained speeds in the range of 40-80 μm s$^{-1}$. The movement patterns of biohybrid microrobots in the SLF at 37° C. was also evaluated. Algae-NP(DOX)-robot exhibited a smooth and random motion, similar to the typical movement path of bare algae, suggesting that the binding of NP(DOX) onto the algae body didn't affect the flagella beating (FIG. 14g). It should be noted that 98% of algae-NP(DOX)-robots retained their viability even after a 16-h incubation in SLF, demonstrating their impressive adaptability and ability to operate under conditions mimicking the lung environment.

For biomedical applications, it is imperative that microrobots exhibit minimal cytotoxicity. To test the cytotoxicity of the biohybrid microrobots, NP-functionalized algae that were not loaded with DOX were incubated with both immune cells (J774 macrophage cells) and cancer cells (B16-F10 melanoma cells). Using an MTS assay to measure the viability of cells treated with varying algae-to-cell ratios, no significant differences compared with the untreated control group were observed (FIG. 14h, 14i). The drug release profiles of both NP(DOX) and algae-NP(DOX)-robot in SLF at 37° C. (FIG. 14j) were evaluated. It was shown that the cumulative drug release characteristics of NP(DOX) remained unaffected when bound to the algae microrobots. To assess the in vitro anticancer efficiency of algae-NP (DOX)-robots, we subsequently explored their effects on B16-F10 melanoma cells in comparison with NP(DOX) (FIG. 14k). The dose-responsive curves indicate that the microrobot group was more effective in killing the cancer cells when compared to the NP(DOX) group. It is noteworthy to emphasize that the anticancer effects are attributed solely to the functionality of DOX, as the NP-functionalized algae (without DOX) had no impact on the proliferation of B16-F10 cells as shown in FIG. 14i. These findings suggest that the algae-NP(DOX)-robot exhibits potent effectiveness in inhibiting the growth and proliferation of cancer cells, thus holding promise as a platform for cancer treatment.

In vivo biodistribution and drug retention of algae-NP (DOX)-robot. We next evaluated whether the biohybrid microrobots could be used to deliver anticancer drugs to the lungs and improve the drug retention. A DOX dose of 75 μg per mouse was intratracheally administered to test the delivery efficiency. Following intratracheal administration, the lungs were collected to examine the distribution of both the drug and the microalgae carriers at various timepoints. Ex vivo fluorescence imaging revealed that DOX was detectable in both the algae-NP(DOX)-robot and NP(DOX) groups (FIG. 15a), whereas only the algae-NP(DOX)-robot group exhibited a robust signal corresponding to chloroplast autofluorescence (FIG. 15b). To accurately quantify drug retention in the lungs, a highly sensitive liquid chromatography-mass spectroscopy (LC-MS) technique was employed. At 0 h, both groups contained approximately 70 ag of DOX, which was comparable to the 75-μg dose that was administered, suggesting that most of the drug was successfully delivered to the lung (FIG. 15c). At later timepoints (4 h and 24 h), the remaining drug in the algae-NP(DOX)-robot group was 2.5-fold and 4.4-fold higher, respectively, compared to the NP(DOX) group (FIG. 15d, 15e). When normalized to the input, 62.7% and 9.4% of the drug in the algae-NP(DOX)-robot group was retained at 4 h and 24 h, respectively; in contrast, only 25.5% and 2.1% of the drug remained after NP(DOX) administration at the same timepoints. Furthermore, the histological distribution of the algae-NP(DOX)-robot within the lungs at 24 h after administration (FIG. 15f) was evaluated. Stronger DOX fluorescence was observed in lung sections treated with algae-NP(DOX)-robot compared to those treated with NP(DOX), consistent with the quantitative retention data. The algae autofluorescence colocalized well with DOX in the bronchioles, indicating the stability of the chemically bonded NP(DOX) after delivery. In addition, the algae-NP(DOX)-robot delivered DOX deep into the tissue, whereas little DOX was found in the same regions for the NP(DOX) group. Quantification of the fluorescence in the lung sections revealed a 5.5-fold higher level of DOX for mice receiving algae-NP(DOX)-robots (FIG. 15g).

To better understand the enhanced drug distribution and retention of the algae-NP(DOX)-robots compared to NP(DOX), a potential clearance mechanism from the lungs was investigated. Alveolar macrophages, which are lung-resident immune cells that express specific surface markers such as Siglec-F and CD11c, and play a crucial role in surfactant clearance and immune surveillance. Flow cytometry analysis was conducted to assess the interaction between alveolar macrophages and algae-NP(DOX)-robots at various timepoints following intratracheal administration (FIG. 15h, 15i). When looking at the CD11c+Siglec-F+ population in the bronchoalveolar lavage fluid (BALF), minimal DOX uptake was observed over the initial 4 h in the case of algae-NP(DOX)-robot, with increased uptake occurring after at 8 h; in contrast, alveolar macrophages in the NP(DOX) group exhibited elevated uptake after only 1 h (FIG. 15h). The delayed uptake of DOX in algae-NP(DOX)-robot was consistent with the uptake profile of the algal component over the same time period (FIG. 15i) and thought to be attributed to the motility of microalgae, which allows them to evade macrophage uptake.

In vivo anticancer therapeutic efficacy of algae-NP(DOX)-robot. We further established a B16-F10-Luc2 melanoma lung metastasis model to evaluate the anti-metastatic efficacy of the algae-NP(DOX)-robot platform (FIG. 16a). This model was established by intravenously injecting $1 \times 10^5$ B16-F10-Luc2 cells through the tail vein of C57BL/6 mice. The treatment regimen consisted of four 75-μg DOX doses given every other day, with the first dose administered one day after the tumor challenge. The progression of lung metastasis was evaluated by measuring bioluminescence intensity in the lungs, and significantly better inhibition of lung metastasis progression was observed for the algae-NP(DOX)-robot group as compared to the free drug or NP(DOX) control groups (FIG. 16b, 16c). We also quantified the overall lung metastasis burden based on the bioluminescence intensity in the lungs (FIG. 16d). During the first 20 days after tumor inoculation, lung metastasis was nearly completely suppressed in mice treated with algae-NP(DOX)-robot. In particular, the total bioluminescence intensity for the algae-NP(DOX)-robot group was 88.7-fold lower compared with the blank control. On day 24, treatment using algae-NP(DOX)-robots led to a 19.6-fold and 38.2-fold lower total bioluminescence intensity compared to free DOX and NP(DOX), respectively (FIG. 16e). Survival analysis further validated the significantly improved therapeutic benefit of the algae-NP(DOX)-robots (FIG. 16f). Whereas free drug and NP(DOX) control treatments did not enhance survival, with a median survival time of 27 days, the group treated with algae-NP(DOX)-robots experienced a 40% increase in median survival time, extending it to 37 days. Additionally, we monitored for changes in body weight during the entire treatment period (FIG. 16g). No significant body weight loss was observed in the algae-NP (DOX) and NP(DOX) treatment groups. However, a pronounced decline in body weight was evident during the first 7 days of free DOX treatment, indicating the presence of some toxicity.

In vivo toxicity assessment of algae-NP(DOX)-robot. Finally, the toxicity profile of the algae-NP(DOX)-robot was assessed. Healthy mice were subjected to intratracheal administration using one of three different treatments: algae-NP(DOX)-robot, free DOX, and NP(DOX). Each mouse received a total of four 75-μg DOX doses given every other day. A blood count and a comprehensive metabolic panel were performed one day after the final injection to assess the effects of these treatments. The levels of several biomarkers commonly associated with liver and kidney functions, including albumin (ALB), alkaline phosphatase (ALP), alanine transaminase (ALT), blood urea nitrogen (BUN), total bilirubin (TBIL), and creatinine (CRE), and found no abnormalities (FIG. 17a) were examined. Other biomarkers such as calcium (CA), glucose (GLU), phosphorus (PHOS), potassium (K+), sodium (Na+), and total protein (TP) were also found to be within their normal ranges. Furthermore, the absence of any significant hematologic abnormalities resulting from algae-NP(DOX)-robot treatment was confirmed, as the levels of white blood cells, red blood cells, and platelets all remained within the normal limits (FIG. 17b). Notably, the free drug group displayed elevated platelet levels, again indicating a certain degree of toxicity. Histological examination of tissue sections, including the heart, liver, spleen, lungs, and kidneys, revealed no observable damage (FIG. 17c).

In summary, this example demonstrated an attractive approach to engineering living microalgae as a biohybrid microrobotic vehicle to deliver nanotherapeutics into deep lung tissues for the treatment of lung metastasis. Synthetic cell membrane-coated anticancer drug-loaded nanoparticles were bound to the microalgae surface via click chemistry. The linking of the nanoparticles had no effect on either the intrinsic motility of the microalgae or the anticancer activity of the drug payload. Compared with free drug and drug-loaded nanoparticles, the biohybrid microrobots exhibited enhanced tissue accumulation and extended retention in the deep lungs. The prolonged drug retention could be attributed to the unique motion capability of the microalgae, which enables them to evade phagocytosis by alveolar macrophages. Using a mouse model of lung metastasis, the effectiveness of our biohybrid microrobot formulation in delivering DOX to diseased lung tissues was demonstrated, which significantly improved therapeutic outcomes by reducing lung metastasis burden and extending median survival time. Overall, the combination of motile living microalgae and cell membrane-coated drug-loaded nanoparticles presents a novel and powerful approach to pulmonary drug delivery and lays the foundation for engineered biohybrid microrobots in lung metastasis therapy.

Methods

Green algae culture. Chlamydomonas reinhardtii (CC-125 wild-type mt+) was sourced from the Chlamydomonas Resource Center. The strain was cultivated in Tris-acetate-phosphate (TAP) medium (Thermo Fisher Scientific) at room temperature (approximately 22° C.) with alternating cycles of 12 h of exposure to sunlight and 12 h of darkness.

Preparation of PLGA(DOX) and NP(DOX). Doxorubicin (DOX)-loaded PLGA nanoparticles ("PLGA(DOX)") were prepared following a previously reported method[46]. First, the nanoparticle cores were synthesized by a nano-precipitation technique. Briefly, 20 mg of poly(lactic-co-glycolic acid) (PLGA, 50:50, 0.67 dl/g, Lactel Absorbable Polymers) was dissolved in 1 ml of acetone. Subsequently, 5 mg of DOX (Sigma-Aldrich) was dissolved in 500 μl of methanol containing 5 μl of triethylamine. After thoroughly mixing the DOX solution with the PLGA solution, the combined mixture was added dropwise into 10 ml of 1% polyvinyl alcohol solution under 700 rpm stirring. The organic solvent was then evaporated through overnight stirring. To determine the amount of drug loaded into the PLGA nanoparticles, 1 ml of PLGA(DOX) solution was centrifuged for 5 min at 16,100 g, and the supernatant was discarded. The pellet was subsequently dissolved in dimethyl sulfoxide (Sigma-Aldrich) and vortexed at 700 rpm for 15 min to fully release the DOX from the PLGA core. The concentration of DOX was measured using a Tecan Infinite M200 plate reader (excitation/emission=480/590 nm).

RBC membrane-coated DOX-loaded nanoparticles ("NP(DOX)") were synthesized using a previously established membrane coating technique[47]. RBC membrane that was derived from mouse RBC (Bioreclamation) was combined with PLGA(DOX) cores at a 1:2 membrane protein-to-polymer weight ratio. The resulting mixture was then subjected to sonication for 3 min using a Fisherbrand 11201 series bath sonicator. Subsequently, the NP(DOX) were isolated by centrifugation for 5 min at 16,100 g and washed three times with ultrapure water.

The hydrodynamic size and zeta potential of the PLGA (DOX) and NP(DOX) were assessed both before and after the cell membrane coating by dynamic light scattering using a Malvern ZEN 3600 Zetasizer. An FEI Sphera transmission electron microscope operating at 200 kV was used for visualizing the morphology of the NP(DOX) stained with 0.2 wt % uranyl acetate. For SEM characterization, NP(DOX) were sputtered with palladium for imaging on a Zeiss Sigma 500 scanning electron microscope at an acceleration voltage of 3 kV.

Preparation of algae-NP(DOX)-robot. Cultured algae were washed five times using ultrapure water by centrifuging at 500 g for 3 min. The concentration of the algae was then adjusted to $1 \times 10^7$ cells ml$^{-1}$. Next, 1 ml of algae solution was incubated with 4 μl of 10 mM azido-PEG$_4$-NHS ester (Click Chemistry Tools) for 1 h at room temperature (22° C.). Concurrently, 1 ml of 1 mg ml$^{-1}$ NP(DOX) in ultrapure water was combined with 4 μl of 10 mM DBCO-PEG$_4$-NHS ester (Click Chemistry Tools) for 1 h at room temperature (22° C.). After the incubations, both the azido-labeled algae and DBCO-labeled NP(DOX) were washed four times with ultrapure water by centrifuging at 500 g for 2 min for the algae and at 16,100 g for 3 min for NP(DOX). The conjugation was executed by mixing $1 \times 10^6$ azido-labeled algae with varying amounts of DBCO-labeled NP(DOX) (6.25 μg, 12.5 μg, 25 μg, 50 μg, 75 μg, and 100 μg) for 1 h at room temperature (22° C.). Following conjugation, the samples were washed three times with ultrapure water to remove free NP(DOX) by centrifuging at 500 g for 2 min. Finally, the resulting algae-NP(DOX)-robot were stored in ultrapure water for further use.

Characterization of algae-NP(DOX)-robot. To prepare algae-NP(DOX)-robot for SEM imaging, fixation was performed by combining it with a 5% glutaraldehyde solution (Sigma-Aldrich) in a 1:1 volume ratio. The fixed samples were then stored overnight at 4° C. Afterwards, the samples were washed three times with ultrapure water by centrifuging at 100 g for 2 min, after which they were left to dry overnight. Subsequently, the samples were coated with iridium and imaged used using a Zeiss Sigma 500 scanning electron microscope at an acceleration voltage of 3 kV. Fluorescent microscopy (Evos FL) was utilized to examine the autofluorescence of the algae and DOX loaded in the PLGA cores under the Cy5 and RFP channels, respectively. To determine the percentage of algae bound with NP(DOX), various quantities of NP(DOX) were co-incubated with the algae and then washed three times by centrifuging at 500 g for 2 min to remove unbound NP(DOX). These algae-NP (DOX)-robot samples were then resuspended in deionized water for flow cytometry analysis. The data was collected using a Becton Dickinson LSR II flow cytometer and analyzed with FlowJo v10.4 software.

Motion analysis. Bare algae and algae-NP(DOX)-robots with various NP(DOX) inputs (6.25 μg, 25 μg, and 100 μg) were suspended in simulated lung fluid (SLF) at room temperature (22° C.) to measure their speed and motility ratio. The SLF was prepared based on the previous reference[29]. Algae-NP(DOX)-robot with a 25-μg NP(DOX) input were subjected to further analysis at body temperature (37° C.) in SLF at 0 h and 2 h. Furthermore, to visualize the trajectory of algae-NP(DOX)-robots, motion tracking lines were recorded over 2 s in the bright-field (BF), Cy5, and RFP channels. All motion videos were taken by a Nikon Eclipse Ti-S/L100 inverted optical microscope equipped with a Hamamatsu C11440 digital camera under a Nikon 10× objective lens. The speed of the bare algae and algae-NP(DOX)-robot under various conditions was analyzed using the NIS-elements tracking module.

In vitro cytotoxicity of NP-functionalized algae without DOX. To assess the cytotoxicity of NP-functionalized algae without DOX, co-incubation experiments were conducted in Dulbecco's modified Eagle medium (DMEM, Thermo Fisher Scientific). J774 macrophage cells (ATCC TIB-67) and B16-F10 (ATCC CRL-6475) cancer cells were seeded into 96-well plates at $1 \times 10^5$ per well. Varying concentrations of NP-functionalized algae without DOX were added to the cells, followed by incubation for 24 h at 37° C. To test for any cytotoxicity, an MTS assay (Abcam) was subsequently incubated with the cells at 37° C. for 45 min. Results were determined by measuring the absorbance at a wavelength of 490 nm using a BioTek Synergy Mx microplate reader.

In vitro DOX release from algae-NP(DOX)-robot. DOX release was evaluated by analyzing the supernatant from algae-NP(DOX)-robots and NP(DOX) at multiple time points, ranging from 0 h to 48 h. The concentration of DOX in the supernatant was quantified using a Tecan Infinite M200 plate reader (excitation/emission=480/590 nm).

In vitro anticancer effects of algae-NP(DOX)-robot. To investigate the in vitro anticancer effects of algae-NP (DOX)-robots, B16-F10 cells were seeded into 96-well plates at a density of $1 \times 10^6$ per well in 100 μl of DMEM medium. After 24 h, different amounts of algae-NP(DOX)-robots or NP(DOX) containing 0.005 μg ml$^{-1}$, 0.05 μg ml$^{-1}$, 0.5 μg ml$^{-1}$, 2.5 μg ml$^{-1}$, 5 μg ml$^{-1}$, 25 μg ml$^{-1}$, and 75 μg ml$^{-1}$ of DOX were added to the wells. Cell viability was assessed after 24 h using an MTS assay as described above.

Animal care. Six-week-old female C57BL/6 mice were purchased from Envigo and housed in an animal facility at the University of California San Diego (UCSD). All animal experiments were approved by the Institutional Animal Care and Use Committee of UCSD and performed under federal, state, local and National Institutes of Health guidelines.

In vivo retention and lung distribution. Female C57BL/6 mice were anesthetized with a ketamine (Dechra) and xylazine (VetOne) cocktail and were then intratracheally administered with either algae-NP(DOX)-robot or NP(DOX), both containing a DOX dose of 75 g. The same dosage was applied for all subsequent in vivo experiments. The mice that received no treatment served as controls. After various time intervals (0, 4 and 24 h), groups of mice were euthanized, and their lungs were excised for analysis. The fluorescence of the lungs was imaged and quantified using a PerkinElmer Xenogen IVIS 200 system. To measure the remaining amount of DOX, lung tissues were homogenized using a BioSpec Mini-BeadBeater-16. The quantity of DOX was measured using liquid chromatography-mass spectrometry (LC-MS), which was performed in the Molecular Mass Spectrometry Facility at UCSD.

To study drug distribution in the lungs, algae-NP(DOX)-robot and NP(DOX) were intratracheally administered to female C57BL/6 mice. At 24 h after treatment, the lungs were collected and snap-frozen at −80° C. in Tissue-Tek O.C.T. compound (Sakura). Cryosections were prepared by the Moores Cancer Center Tissue Technology Shared Resource (Cancer Center Support Grant P30CA23100). To visualize the distribution within the lung tissue, the sections were stained with 10 μg ml$^{-1}$ Hoechst 33342 (Thermo Scientific) at room temperature for 20 min. They were then mounted with Fluoromount-G mounting medium (Invitrogen) and imaged on a Leica SP8 confocal microscope (NINDS P30NS047101).

In vivo macrophage clearance. After intratracheal injection with algae-NP(DOX)-robot or NP(DOX), bronchoalveolar lavage fluid (BALF) was collected at different time points (1, 4, 8, 24 h) following a previously established protocol[29]. In brief, mice were euthanized by $CO_2$ inhalation, and the trachea was exposed. An incision was made in the trachea, followed by the insertion of a catheter. BALF was obtained through triplicate washes with 0.5 ml of 0.5% (v/v) fetal bovine serum (Gibco) and 2 mM Ethylene diamine tetraacetic acid (EDTA, Thermo Fisher Scientific) in PBS, and the collected samples were stored on ice. The BALF was then centrifuged at 700 g for 5 min and treated with RBC lysis buffer (BioLegend) per the manufacturer's instructions. Afterwards, the cells were blocked with 1% fetal bovine serum (Gibco) in PBS on ice for 30 min and stained with FITC anti-mouse Siglec-F (S17007L, BioLegend) and Pacific Blue anti-mouse CD11c (N418, BioLegend). After washing with PBS to remove unbound antibodies, cells were resuspended in PBS for flow cytometry analysis. Data was collected using a Becton Dickinson LSR II flow cytometer and analyzed using FlowJo v10.4 software.

In vivo efficacy in a lung metastasis model. To establish an experimental lung metastasis model, $1\times10^5$ B16-F10-Luc2 cells (ATCC CRL-6475-LUC2) were injected intravenously into the tail vein of female C57BL/6 mice. The mice received treatment with free DOX, NP(DOX) and algae-NP (DOX)-robot through intratracheal instillation on days 1, 3, 5 and 7 after tumor cell inoculation. Mice without treatment were used as controls. To monitor tumor growth, on days 12, 16, 20, 24 and 28 after tumor cell inoculation, the mice were intraperitoneally administered 200 μl of 5 mg ml$^{-1}$ D-luciferin (Syd Labs) in DPBS (Gibco). Bioluminescence signals were detected using a PerkinElmer Xenogen IVIS 200 system. The body weight and survival of each mouse were also monitored throughout the study.

In vivo safety evaluation. Healthy female C57BL/6 mice were intratracheally administered with free DOX, NP(DOX) and algae-NP(DOX)-robot every other day for a total of four injections. Mice without treatment were used as controls. At 24 h following the last treatment, blood samples were collected via submandibular puncture into Microvette 100 EDTA K3E tubes (Sarstedt) for blood cell quantification. To collect serum for comprehensive blood chemistry analysis, blood samples were obtained without any anticoagulant, placed at room temperature for 30 min, and centrifuged at 3000 g for 10 min. Both the blood cell quantification and blood chemistry analyses were performed by the Animal Care Program Diagnostic Services Laboratory at UCSD. For histological analysis, the heart, liver, spleen, lungs and kidneys were excised and fixed in phosphate-buffered 10% formalin (Fisher Chemical), followed by sectioning and hematoxylin and eosin staining. These histological procedures were conducted by the Moores Cancer Center Tissue Technology Shared Resource.

REFERENCES

ADDIN EN.REFLIST 1. Nguyen, D. X.; Bos, P. D.; Massagué, J., Metastasis: from dissemination to organ-specific colonization. Nat. Rev. Cancer 9, 274 (2009).
2. Mohammed, T.-L. H.; Chowdhry, A.; Reddy, G. P.; Amorosa, J. K.; Brown, K.; Dyer, D. S.; Ginsburg, M. E.; Heitkamp, D. E.; Jeudy, J.; Kirsch, J., ACR Appropriateness Criteria® screening for pulmonary metastases. J. Thorac. Imaging 26, Wi (2011).
3. Altorki, N. K.; Markowitz, G. J.; Gao, D.; Port, J. L.; Saxena, A.; Stiles, B.; McGraw, T.; Mittal, V., The lung microenvironment: an important regulator of tumour growth and metastasis. Nat. Rev. Cancer 19, 9 (2019).
4. Chabner, B. A.; Roberts Jr, T. G., Chemotherapy and the war on cancer. Nat. Rev. Cancer 5, 65 (2005).
5. Azarmi, S.; Roa, W. H.; Löbenberg, R., Targeted delivery of nanoparticles for the treatment of lung diseases. Adv. Drug Deliv. Rev. 60, 863 (2008).
6. Schroeder, A.; Heller, D. A.; Winslow, M. M.; Dahlman, J. E.; Pratt, G. W.; Langer, R.; Jacks, T.; Anderson, D. G., Treating metastatic cancer with nanotechnology. Nat. Rev. Cancer 12, 39 (2012).
7. Mitragotri, S.; Burke, P. A.; Langer, R., Overcoming the challenges in administering biopharmaceuticals: formulation and delivery strategies. Nat. Rev. Drug Discov. 13, 655 (2014).
8. Sindhwani, S.; Syed, A. M.; Ngai, J.; Kingston, B. R.; Maiorino, L.; Rothschild, J.; MacMillan, P.; Zhang, Y.; Rajesh, N. U.; Hoang, T.; Wu. J. L. Y.; Wilhelm, S.; Zilman, A.; Gadde, S.; Sulaiman, A.; Ougyang, B.; Lin, Z.; Wang, L.; Egeblad, M.; Chan, W. C. W., The entry of nanoparticles into solid tumours. Nat. Mater. 19, 566 (2020).
9. Blanco, E.; Shen, H.; Ferrari, M., Principles of nanoparticle design for overcoming biological barriers to drug delivery. Nat. Biotechnol. 33, 941 (2015).
10. Patton, J. S.; Byron, P. R., Inhaling medicines: delivering drugs to the body through the lungs. Nat. Rev. Drug Discov. 6, 67 (2007).
11. Choi, H. S.; Ashitate, Y.; Lee, J. H.; Kim, S. H.; Matsui, A.; Insin, N.; Bawendi, M. G.; Semmler-Behnke, M.; Frangioni, J. V.; Tsuda, A., Rapid translocation of nanoparticles from the lung airspaces to the body. Nat. Biotechnol. 28, 1300 (2010).

12. Patton, J. S., Mechanisms of macromolecule absorption by the lungs. *Adv. Drug Deliv. Rev.* 19, 3 (1996).

13. Merkel, O. M.; Zheng, M.; Debus, H.; Kissel, T., Pulmonary gene delivery using polymeric nonviral vectors. *Bioconjug. Chem.* 23, 3 (2012).

14. Loira-Pastoriza, C.; Todoroff, J.; Vanbever, R., Delivery strategies for sustained drug release in the lungs. *Adv. Drug Deliv. Rev.* 75, 81 (2014).

15. Rotolo, L.; Vanover, D.; Bruno, N. C.; Peck, H. E.; Zurla, C.; Murray, J.; Noel, R. K.; O'Farrell, L.; Araínga, M.; Orr-Burks, N.; Joo, J. Y.; Chaves, L. C. S.; Jung, Y.; Beyersdorf, J.; Gumber, S.; Guerrero-Ferreira, R.; Cornejo, S.; Thoresen, M.; Olivier, A. K.; Kuo, K. M.; Gumbart, J. C.; Woolums, A. R.; Villinger, F.; Lafontaine, E. R.; Hogan, R. J.; Finn, M. G.; Santangelo, P. J., Species-agnostic polymeric formulations for inhalable messenger RNA delivery to the lung. *Nat. Mater.* 22, 369 (2023).

16. Wang, Z.; Popowski, K. D.; Zhu, D.; de Juan Abad, B. L.; Wang, X.; Liu, M.; Lutz, H.; De Naeyer, N.; DeMarco, C. T.; Denny, T. N.; Dinh, P-U. C.; Li, Z.; Cheng, K., Exosomes decorated with a recombinant SARS-CoV-2 receptor-binding domain as an inhalable COVID-19 vaccine. *Nat. Biomed. Eng.* 6, 791 (2022).

17. Dinh, P.-U. C.; Paudel, D.; Brochu, H.; Popowski, K. D.; Gracieux, M. C.; Cores, J.; Huang, K.; Hensley, M. T.; Harrell, E.; Vandergriff, A. C., Inhalation of lung spheroid cell secretome and exosomes promotes lung repair in pulmonary fibrosis. *Nat. Commun.* 11, 1064 (2020).

18. Liu, Y.; Crowe, W. N.; Wang, L.; Lu, Y.; Petty, W. J.; Habib, A. A.; Zhao, D., An inhalable nanoparticulate STING agonist synergizes with radiotherapy to confer long-term control of lung metastases. *Nat. Commun.* 10, 5108 (2019).

19. Geiser, M.; Kreyling, W. G., Deposition and biokinetics of inhaled nanoparticles. *Part. Fibre Toxicol.* 7, 1 (2010).

20. Li, J.; Esteban-Fernández de Ávila, B.; Gao, W.; Zhang, L.; Wang, J., Micro/nanorobots for biomedicine: Delivery, surgery, sensing, and detoxification. *Sci. Robot.* 2, eaam6431 (2017).

21. de Ávila, B. E.-F.; Angsantikul, P.; Li, J.; Lopez-Ramirez, M. A.; Ramírez-Herrera, D. E.; Thamphiwatana, S.; Chen, C.; Delezuk, J.; Samakapiruk, R.; Ramez, V.; Obonyo, M.; Zhang, L.; Wang, J., Micromotor-enabled active drug delivery for in vivo treatment of stomach infection. *Nat. Commun.* 8, 272 (2017).

22. Zhang, H.; Li, Z.; Gao, C.; Fan, X.; Pang, Y.; Li, T.; Wu, Z.; Xie, H.; He, Q., Dual-responsive biohybrid neutrobots for active target delivery. *Sci Robot.* 6, aaz9519 (2021).

23. Wan, M.; Wang, Q.; Wang, R.; Wu, R.; Li, T.; Fang, D.; Huang, Y.; Yu, Y.; Fang, L.; Wang, X.; Zhang, Y.; Miao, Z.; Zhao, B.; Wang, F.; Mao, C.; Jiang, Q.; Xu, X.; Shi, D., Platelet-derived porous nanomotor for thrombus therapy. *Sci. Adv.* 6, eaaz9014 (2020).

24. Felfoul, O.; Mohammadi, M.; Taherkhani, S.; De Lanauze, D.; Xu, Y. Z.; Loghin, D.; Essa, S.; Jancik, S.; Houle, D.; Lafleur, M.; Gaboury, L.; Tabrizian, M.; Kaou, N.; Atkin, M.; Vuong, T.; Batist, G.; Beauchemin, N.; Radzioch, D.; Martel, S., Magneto-aerotactic bacteria deliver drug-containing nanoliposomes to tumour hypoxic regions. *Nat. Nanotechnol.* 11, 941 (2016).

25. Zhang, Y.; Zhang, L.; Yang, L.; Vong, C. I.; Chan, K. F.; Wu, W. K.; Kwong, T. N.; Lo, N. W.; Ip, M.; Wong, S. H.; Sung, J. J. Y.; Chiu, P. W. Y.; Zhang, L., Real-time tracking of fluorescent magnetic spore-based microrobots for remote detection of C. diff toxins. *Sci. Adv.* 5, eaau9650 (2019).

26. Cong, Z.; Tang, S.; Xie, L.; Yang, M.; Li, Y.; Lu, D.; Li, J.; Yang, Q.; Chen, Q.; Zhang, Z.; Zhang, X.; Wu, S., Magnetic-Powered Janus Cell Robots Loaded with Oncolytic Adenovirus for Active and Targeted Virotherapy of Bladder Cancer. *Adv. Mater.* 34, 2201042 (2022).

27. Draz, M. S.; Kochehbyoki, K. M.; Vasan, A.; Battalapalli, D.; Sreeram, A.; Kanakasabapathy, M. K.; Kallakuri, S.; Tsibris, A.; Kuritzkes, D. R.; Shafiee, H., DNA engineered micromotors powered by metal nanoparticles for motion based cellphone diagnostics. *Nat. Commun.* 9, 4282 (2018).

28. Schmidt, C. K.; Medina-Sánchez, M.; Edmondson, R. J.; Schmidt, O. G., Engineering microrobots for targeted cancer therapies from a medical perspective. *Nat. Commun.* 11, 5618 (2020).

29. Zhang, F.; Zhuang, J.; Li, Z.; Gong, H.; de Ávila, B. E.-F.; Duan, Y.; Zhang, Q.; Zhou, J.; Yin, L.; Karshalev, E.; Gao, W.; Nizet, V.; Fang, R. H.; Zhang, L.; Wang, J., Nanoparticle-modified microrobots for in vivo antibiotic delivery to treat acute bacterial pneumonia. *Nat. Mater.* 21, 1324 (2022).

30. Wang, B.; Chan, K. F.; Yuan, K.; Wang, Q.; Xia, X.; Yang, L.; Ko, H.; Wang, Y.-X. J.; Sung, J. J. Y.; Chiu, P. W. Y.; Zhang, L., Endoscopy-assisted magnetic navigation of biohybrid soft microrobots with rapid endoluminal delivery and imaging. *Sci. Robot.* 6, eabd2813 (2021).

31. Wrede, P.; Degtyaruk, O.; Kalva, S. K.; Deán-Ben, X. L.; Bozuyuk, U.; Aghakhani, A.; Akolpoglu, B.; Sitti, M.; Razansky, D., Real-time 3D optoacoustic tracking of cell-sized magnetic microrobots circulating in the mouse brain vasculature. *Sci. Adv.* 8, eabm9132 (2022).

32. Wu, Z.; Li, L.; Yang, Y.; Hu, P.; Li, Y.; Yang, S.-Y.; Wang, L. V.; Gao, W., A microrobotic system guided by photoacoustic computed tomography for targeted navigation in intestines in vivo. *Sci. Robot.* 4, eaax0613 (2019).

33. Karshalev, E.; Esteban-Fernández de Ávila, B.; Beltrán-Gastélum, M.; Angsantikul, P.; Tang, S.; Mundaca-Uribe, R.; Zhang, F.; Zhao, J.; Zhang, L.; Wang, J., Micromotor Pills as a Dynamic Oral Delivery Platform. *ACS Nano* 12, 8397 (2018).

34. Li, J.; Thamphiwatana, S.; Liu, W.; Esteban-Fernández de Ávila, B.; Angsantikul, P.; Sandraz, E.; Wang, J.; Xu, T.; Soto, F.; Ramez, V.; Wang, X.; Gao, W.; Zhang, L.; Wang, J., Enteric micromotor can selectively position and spontaneously propel in the gastrointestinal tract. *ACS Nano* 10, 9536 (2016).

35. Zhang, F.; Li, Z.; Duan, Y.; Luan, H.; Yin, L.; Guo, Z.; Chen, C.; Xu, M.; Gao, W.; Fang, R. H.; Zhang, L.; Wang, J., Extremophile-based biohybrid micromotors for biomedical operations in harsh acidic environments. *Sci. Adv.* 8, eade6455 (2022).

36. Gwisai, T.; Mirkhani, N.; Christiansen, M. G.; Nguyen, T. T.; Ling, V.; Schuerle, S., Magnetic torque-driven living microrobots for increased tumor infiltration. *Sci. Robot.* 7, eabo0665 (2022).

37. Weibel, D. B.; Garstecki, P.; Ryan, D.; DiLuzio, W. R.; Mayer, M.; Seto, J. E.; Whitesides, G. M., Microoxen: Microorganisms to move microscale loads. *Proc. Natl. Acad. Sci. U.S.A.* 102, 11963 (2005).

38. Xu, H.; Medina-Sánchez, M.; Magdanz, V.; Schwarz, L.; Hebenstreit, F.; Schmidt, O. G., Sperm-hybrid micromotor for targeted drug delivery. *ACS Nano* 12, 327 (2017).

39. Akolpoglu, M. B.; Alapan, Y.; Dogan, N. O.; Baltaci, S. F.; Yasa, O.; Aybar Tural, G.; Sitti, M., Magnetically steerable bacterial microrobots moving in 3D biological matrices for stimuli-responsive cargo delivery. *Sci. Adv.* 8, eabo6163 (2022).

40. Zhang, F.; Li, Z.; Chen, C.; Luan, H.; Fang, R. H.; Zhang, L.; Wang, J., Biohybrid microalgae robots: design, fabrication, materials and applications. *Adv. Mater.* 2303714 (2023).

41. Akolpoglu, M. B.; Dogan, N. O.; Bozuyuk, U.; Ceylan, H.; Kizilel, S.; Sitti, M., High-Yield Production of Biohybrid Microalgae for On-Demand Cargo Delivery. *Adv. Sci.* 16, 2001256 (2020).

42. Shchelik, I. S.; Molino, J. V.; Gademann, K., Biohybrid microswimmers against bacterial infections. *Acta Biomater.* 136, 99 (2021).

43. Zhang, F.; Li, Z.; Duan, Y.; Abbas, A.; Mundaca-Uribe, R.; Yin, L.; Luan, H.; Gao, W.; Fang, R. H.; Zhang, L., Gastrointestinal tract drug delivery using algae motors embedded in a degradable capsule. *Sci. Robot.* 7, eabo4160 (2022).

44. Wang, J.; Soto, F.; Liu, S.; Yin, Q.; Purcell, E.; Zeng, Y.; Hsu, E. C.; Akin, D.; Sinclair, B.; Stoyanova, T., Volbots: Volvox Microalgae-Based Robots for Multimode Precision Imaging and Therapy. *Adv. Funct. Mater.* 32, 2201800 (2022).

45. Zhang, F.; Li, Z.; Yin, L.; Zhang, Q.; Askarinam, N.; Mundaca-Uribe, R.; Tehrani, F.; Karshalev, E.; Gao, W.; Zhang, L., ACE2 Receptor-Modified Algae-Based Microrobot for Removal of SARS-CoV-2 in Wastewater. *J. Am. Chem. Soc.* 143, 12194 (2021).

46. Zhao, Z.; Ukidve, A.; Gao, Y.; Kim, J.; Mitragotri, S., Erythrocyte leveraged chemotherapy (ELeCt): Nanoparticle assembly on erythrocyte surface to combat lung metastasis. *Sci. Adv.* 5, eaax9250 (2019).

47. Fang, R. H.; Kroll, A. V.; Gao, W.; Zhang, L., Cell membrane coating nanotechnology. *Adv. Mater.* 30, 1706759 (2018).

48. Schenck, T. L.; Hopfner, U.; Chivez, M. N.; Machens, H.-G.; Somlai-Schweiger, I.; Giunta, R. E.; Bohne, A. V.; Nickelsen, J.; Allende, M. L.; Egana, J. T., Photosynthetic biomaterials: a pathway towards autotrophic tissue engineering. *Acta Biomater.* 15, 39 (2015).

49. Ueno, Y.; Aikawa, S.; Kondo, A.; Akimoto, S., Adaptation of light-harvesting functions of unicellular green algae to different light qualities. *Photosynth. Res.* 139, 145 (2019).

50. Hunter, E. L.; Penny, G. M.; Dutcher, S. K., Algal Ciliary Motility. *eLS* 2, 1 (2021).

What is claimed is:

1. A hybrid microrobot comprising motile algae conjugated with a therapeutic agent-loaded cellular membrane-coated polymeric nanoparticle.

2. The hybrid microrobot of claim 1, wherein the cellular membrane is a neutrophil membrane or red blood cell membrane.

3. The hybrid microrobot of claim 1, wherein the therapeutic agent is an antibiotic, antiviral or anti-cancer agent.

4. The hybrid microrobot of claim 1, wherein the therapeutic agent is ciprofloxacin or doxorubicin.

5. The hybrid microrobot of claim 1, wherein the algae is *Chlamydomonas reinhardtii*.

6. The hybrid microrobot of claim 1, wherein the algae has a surface modified with azido-PEG4-N-hydroxysuccinimide (NHS) ester, and is conjugated with dibenzocyclooctyne (DBCO)-PEG$_4$-NHS ester modified membrane-coated polymeric nanoparticles.

7. The hybrid microrobot of claim 1, wherein the polymeric nanoparticle comprises poly(lactic-co-glycolic acid) (PLGA).

8. The hybrid microrobot of claim 1, wherein the hybrid microrobot is embedded inside a pH-sensitive capsule for gastrointestinal delivery.

9. The hybrid microrobot of claim 1, wherein the hybrid microrobot has locomotive ability of at least 110 $\mu$m s$^{-1}$ in the lungs in vivo.

10. The hybrid microrobot of claim 1, wherein the hybrid microrobot has a tissue retention time of at least 2 days.

11. A pharmaceutical composition comprising the hybrid microrobot of claim 1, and a pharmaceutically acceptable carrier.

12. A method of treating a pulmonary disease or condition comprising administering to a subject in need an effective amount of a hybrid microrobot of claim 1.

13. The method of claim 12, wherein the pulmonary disease is due to an infection by a virus or bacteria.

14. The method of claim 12, the disease is caused by a bacterial pneumonia.

15. The method of claim 14, the bacteria is *Pseudomonas aeruginosa*.

16. The method of claim 12, the disease is caused by a viral pneumonia.

17. The method of claim 12, the disease is caused by a cancer.

18. The method of claim 12, the administration is to the lungs of the subject.

19. The method of claim 18, the administration is intratracheal.

20. The method of claim 12, the administration is to the gastrointestinal tract of the subject.

21. The method of claim 20, the administration is intraesophageal or endogastric.

* * * * *